US011685777B2

(12) United States Patent
Attar et al.

(10) Patent No.: US 11,685,777 B2
(45) Date of Patent: Jun. 27, 2023

(54) ANTI-GPRC5D ANTIBODIES, BISPECIFIC ANTIGEN BINDING MOLECULES THAT BIND GPRC5D AND CD3, AND USES THEREOF

(71) Applicant: Janssen Pharmaceutica NV, Beerse (BE)

(72) Inventors: Ricardo Attar, Lawrenceville, NJ (US); Francois Gaudet, Spring House, PA (US); Mark Tornetta, Collegeville, PA (US); Alexey Teplyakov, Phoenixville, PA (US); Mark Mendonca, Philadelphia, PA (US); Suzanne Edavettal, San Diego, CA (US); Kodandaram Pillarisetti, Spring House, PA (US); Nathan Majewski, Warrington, PA (US); Yingzhe Li, Dresher, PA (US); Leopoldo L. Luistro, III, Lansdale, PA (US); Diana Chin, Norwood, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/779,713

(22) Filed: Feb. 3, 2020

(65) Prior Publication Data
US 2023/0084967 A1    Mar. 16, 2023

Related U.S. Application Data

(62) Division of application No. 15/655,086, filed on Jul. 20, 2017, now Pat. No. 10,562,968.

(60) Provisional application No. 62/364,811, filed on Jul. 20, 2016.

(51) Int. Cl.
C07K 16/00    (2006.01)
C07K 16/28    (2006.01)
A61K 39/00    (2006.01)

(52) U.S. Cl.
CPC .......... *C07K 16/28* (2013.01); *A61K 39/0011* (2013.01); *C07K 16/2809* (2013.01); *A61K 2039/505* (2013.01); *C07K 2317/21* (2013.01); *C07K 2317/31* (2013.01); *C07K 2317/33* (2013.01); *C07K 2317/565* (2013.01); *C07K 2317/732* (2013.01); *C07K 2317/734* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 6,737,056 B1 | 5/2004 | Presta |
| 8,236,308 B2 | 8/2012 | Kischel et al. |
| 10,562,968 B2 | 2/2020 | Attar et al. |
| 2002/0198362 A1 | 12/2002 | Gaiger et al. |
| 2005/0019320 A1 | 1/2005 | Sugaru et al. |
| 2009/0182127 A1 | 7/2009 | Kjaergaard et al. |
| 2010/0015133 A1 | 1/2010 | Igawa et al. |
| 2010/0028637 A1 | 2/2010 | Tavsanli et al. |
| 2011/0123532 A1 | 5/2011 | Gurney et al. |
| 2011/0206660 A1 | 8/2011 | Blanchetot et al. |
| 2012/0149876 A1 | 6/2012 | Von Kreudenstein et al. |
| 2013/0195849 A1 | 8/2013 | Von Kreudenstein et al. |
| 2022/0177584 A1 | 6/2022 | Girgis et al. |
| 2022/0373550 A1 | 11/2022 | Pillarisetti et al. |

FOREIGN PATENT DOCUMENTS

| | | |
|---|---|---|
| EP | 1468694 A1 | 10/2004 |
| FR | 2994803 B1 | 2/2016 |
| NC | 20190009680 | 9/2019 |
| WO | 2000041474 A2 | 7/2000 |
| WO | 2005086568 A2 | 9/2005 |
| WO | 2006028936 A2 | 3/2006 |
| WO | 2007059782 A1 | 5/2007 |
| WO | 2008119565 A2 | 10/2008 |
| WO | 2008119566 A2 | 10/2008 |

(Continued)

OTHER PUBLICATIONS

Almagro et al., "Humanization of Antibodies," Frontiers in Bioscience (2008) vol. 13, pp. 1619-1633.
Non-Final Office Action for U.S. Appl. No. 15/655,086 dated Feb. 19, 2019.
Notice of Allowance for U.S. Appl. No. 15/655,086 dated Sep. 23, 2019.
Restriction Requirement for U.S. Appl. No. 15/655,086 dated Jan. 11, 2018.
U.S. Appl. No. 18/157,800, filed Jan. 20, 2023, which is accessible to the USPTO via the Image File Wrapper (IFW) System.
U.S. Appl. No. 18/052,172, filed Nov. 2, 2022, which is accessible to the USPTO via the mage File Wrapper (IFW) System.

(Continued)

*Primary Examiner* — Meera Natarajan
(74) *Attorney, Agent, or Firm* — Troutman Pepper Hamilton Sanders LLP

(57) ABSTRACT

Provided herein are antibodies that specifically bind to GPRC5D. Also described are related polynucleotides capable of encoding the provided GPRC5D-specific antibodies or antigen-binding fragments, cells expressing the provided antibodies or antigen-binding fragments, as well as associated vectors and detectably labeled antibodies or antigen-binding fragments. In addition, methods of using the provided antibodies are described. For example, the provided antibodies may be used to diagnose, treat, or monitor GPRC5D-expressing cancer progression, regression, or stability; to determine whether or not a patient should be treated for cancer; or to determine whether or not a subject is afflicted with GPRC5D-expressing cancer and thus may be amenable to treatment with a GPRC5D-specific anti-cancer therapeutic, such as the multispecific antibodies against GPRC5D and CD3 described herein.

9 Claims, 22 Drawing Sheets

Specification includes a Sequence Listing.

(56) References Cited

FOREIGN PATENT DOCUMENTS

| WO | 2008119567 A2 | 10/2008 |
|---|---|---|
| WO | 2009085462 A1 | 7/2009 |
| WO | 2010037836 A2 | 4/2010 |
| WO | 2010037837 A2 | 4/2010 |
| WO | 2010037838 A2 | 4/2010 |
| WO | 2010051274 A2 | 5/2010 |
| WO | 2010093627 A2 | 8/2010 |
| WO | 2011131746 A2 | 10/2011 |
| WO | 2012158818 A2 | 11/2012 |
| WO | 2014131712 A1 | 9/2014 |
| WO | 2015149077 A1 | 10/2015 |
| WO | 2016/036937 A1 | 3/2016 |
| WO | 2016036937 A1 | 3/2016 |
| WO | 2016040294 A2 | 3/2016 |
| WO | 2016/090329 A2 | 6/2016 |
| WO | 2016090034 A2 | 6/2016 |
| WO | 2016090329 A2 | 6/2016 |
| WO | WO/2016/090329 * | 6/2016 |
| WO | 2016209921 A1 | 12/2016 |
| WO | 2017031104 A1 | 2/2017 |
| WO | 2017079121 A2 | 5/2017 |
| WO | 2017189959 A1 | 11/2017 |
| WO | 2019094626 A1 | 5/2019 |
| WO | 2018147245 A1 | 9/2019 |

OTHER PUBLICATIONS

Abhinandan et al., "Analysis and Improvements to Kabat and Structurally Correct Numbering of Antibody Variable Domains", Molecular Immunology (2008) vol. 45, pp. 3832-3839.

Chames et al., "Bispecific Antibodies for Cancer Therapy," Current Opinion in Drug Discovery & Development (2009) vol. 12(2), pp. 276-283.

Cline, "Perspectives for Gene Therapy: Inserting New Genetic Information into Mammalian Cells by Physical Techniques and Viral Vectors," Pharmac. Ther. (1985) vol. 29, pp. 69-92.

Holt et al., "Domain Antibodies: Proteins for Therapy," Trends in Biotechnology (Nov. 2003) vol. 21, No. 11, pp. 484-490.

Okayama et al., "A cDNA Cloning Vector that Permits Expression of cDNA Inserts in Mammalian Cells," Molecular and Cellular Biology (Feb. 1983) vol. 3, No. 2, pp. 280-289.

Revets et al., "Nanobodies as Novel Agents for Cancer Therapy," Expert Opin. Biol. Ther. (2005) vol. 5, No. 1, pp. 111-124.

Shi et al., "De Novo Selection of High-Affinity Antibodies from Synthetic Fab Libraries Displayed on Phage as pIX Fusion Proteins," J. Mol. Biol. (2010) vol. 397, pp. 385-396.

Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry (2002) vol. 278, No. 5, pp. 3466-3473.

Yang et al., "A Common Pathway for T Lymphocyte Activation Involving Both the CD3-Ti Complex and CD2 Sheep Erythrocyte Receptor Determinants," The Journal of Immunology (1986) vol. 137, No. 4, pp. 1097-1100.

Anasetti et al., "Treatment of Acute Graft-Versus-Host Disease With a Nonmitogenic Anti-CD3 Monoclonal Antibody," Transplantation (Nov. 1992) vol. 54(5), pp. 844-851.

Anonymous, "Human GPRC5D APC-Conjugated Antibody," (Oct. 12, 2015) URL: https://resources.mdsystems.com/pdfs/datasheets/fab6300a.pdf, abstract, XP055408560.

Atamaniuk et al., "Overexpression of G Protein-Coupled Receptor 5D in the Bone Marrow is Associated with Poor Prognosis in Patients with Multiple Myeloma," Eur J Clin Invest (Sep. 2012) vol. 42(9), pp. 953-960.

Brauner-Osborne et al., "Cloning and Characterization of a Human Orphan Family C G-protein Coupled Receptor GPRC5D," Biochimeca et Biophysica Acta (2001) vol. 1518, pp. 237-248.

Chothia et al., "Canonical Structures for the Hypervariable Regions of Immunoglobulins," J. Mol. Biol. (1987) vol. 196, pp. 901-917.

Chothia et al., "Conformations of Immunoglobulin Hypervariable Regions," Nature (1989) vol. 342, pp. 877-883.

Cohen et al., "GPRC5D is a Promising Marker for Monitoring the Tumor Load and to Target Multiple Myeloma Cells," Hematology (Nov. 2013) vol. 18(6), pp. 347-350.

Drach et al., "Presence of a p53 Gene Deletion in Patients with Multiple Myeloma Predicts for Short Survival After Conventional-Dose Chemotherapy," Blood (1998) vol. 92(3), pp. 802-809.

Facon et al., "Chromosome 13 Abnormalities Identified by FISH Analysis and Serum β2-microglobulin Produce a Powerful Myeloma Staging System for Patients Receiving High-Dose Therapy," Blood (Mar. 15, 2001) vol. 97(6), pp. 1566-1571.

Ferrara et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-mannosidase II," Biotechnology and Bioengineering (Apr. 5, 2006) vol. 93, No. 5, pp. 851-861.

Ferrara et al., "The Carbohydrate at FcγRIIIa Asn-162: An Element Required for High Affinity Binding to Non-Fuscosylated IgG Glycoforms," The Journal of Biological Chemistry (Feb. 24, 2006) vol. 281, No. 8, pp. 5032-5036.

Gadi et al., "In Vivo Sensitization of Ovarian Tumors to Chemotherapy by Expression of E. Coli Purine Nucleoside Phosphorylase in a Small Fraction of Cells," Gene Therapy (2000) vol. 7, pp. 1738-1743.

Gertz et al., "Clinical Implications of t(11;14)(q13;q32), t(4;14)(p16.3;q32), and 17p13 in Myeloma Patients Treated with High-Dose Therapy," Blood (2005) vol. 106(8), pp. 2837-2840.

Hayano et al., "Proteomic Analysis of Human Nop56p-associated Pre-Ribosomal Ribonucleoprotein Complexes," J. Biol. Chem. (2003) vol. 278(36), pp. 34309-34319.

Holliger et al., "Diabodies: Small Bivalent and Bispecific Antibody Fragments," Proc. Natl. Acad. Sci. USA (Jul. 1993) vol. 90, pp. 6444-6448.

International Search Report and Written Opinion for International PCT Application No. PCT/US2017/042982 dated Feb. 2, 2018.

Konno et al., "Fucose Content of Monoclonal Antibodies can be Controlled by Culture Medium Osmolality for High Antibody-Dependent Cellular Cytotoxicity," Cytotechnology (2012) vol. 64, pp. 249-265.

MacCallum et al., "Antibody-Antigen Interactions: Contact Analysis and Binding Site Topography," J. Mol. Biol. (1996) vol. 262, pp. 732-745.

Martin et al., "Structural Families in Loops of Homologous Proteins: Automatic Classification, Modelling and Application to Antibodies," J. Mol. Biol. (1996) vol. 263, pp. 800-815.

Mori et al., "Engineering Chinese Hamster Ovary Cells to Maximize Effector Function of Produced Antibodies Using FUT8 siRNA," Biotechnology and Bioengineering (Dec. 30, 2004) vol. 88, No. 7, pp. 901-908.

Myers et al., "Optimal Alignments in Linear Space," Cabios (1988) vol. 4, No. 1, pp. 11-17.

Needleman et al., "A General Method Applicable to the Search for Similarities in the Amino Acid Sequence of Two Proteins," J. Mol. Biol. (1970) vol. 48, pp. 443-453.

Olivier et al., "EB66 Cell Line, a Duck Embryonic Stem Cell-Derived Substrate for the Industrial Production of Therapeutic Monoclonal Antibodies with Enhanced ADCC Activity," mAbs (2010) vol. 2, No. 4, pp. 405-415.

Rudikoff et al., "Single Amino Acid Substitution Altering Antigen-Binding Specificity," Proc. Natl. Acad. Sci. USA (Mar. 1, 1982) vol. 79, No. 6, pp. 1979-1983.

Salmeron et al., "A Conformational Epitope Expressed upon Association of CD3-Epsilon with Either CD3-delta or CD3-gamma is the Main Target for Recognition by Anti-CD3 Monoclonal Antibodies," The Journal of Immunology (1991) vol. 147, No. 9, pp. 3047-3052.

Shields et al., "Lack of Fucose on Human IgG1 N-Linked Oligosaccharide Improves Binding to Human FcγRIII and Antibody-Dependent Cellular Toxicity," The Journal of Biological Chemistry (2002) vol. 227, No. 30, pp. 26733-26740.

(56) References Cited

OTHER PUBLICATIONS

Ward et al., "Binding Activities of a Repertoire of Single Immunoglobulin Variable Domains Secreted from *Escherichia Coli*," Nature (1989) vol. 341, pp. 544-546.

Zhou et al., "Development of A Simple and Rapid Method for Producing Non-Fucosylated Oligomannose Containing Antibodies With Increased Effector Function," Biotechnology and Bioengineering (2008) vol. 99, No. 3, pp. 652-665.

* cited by examiner

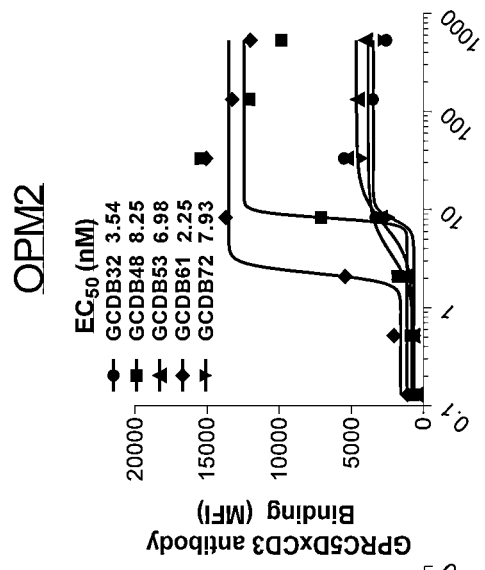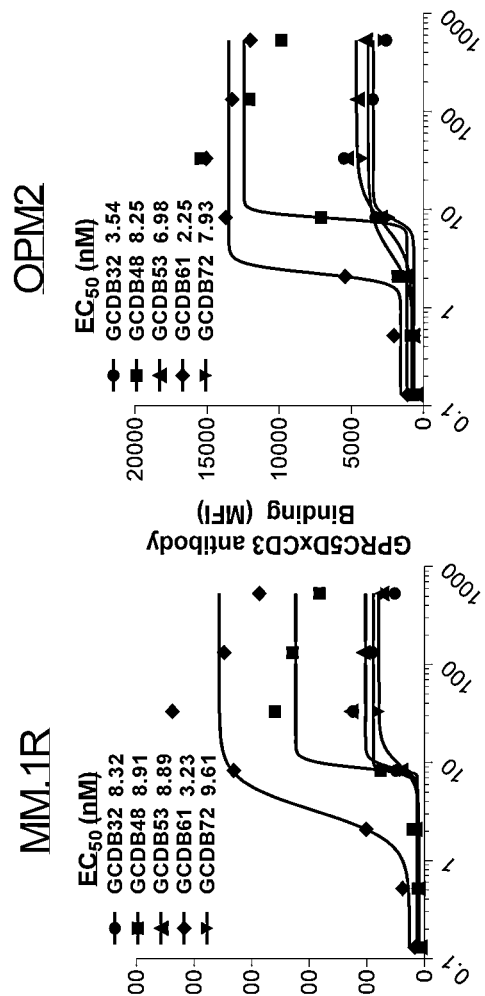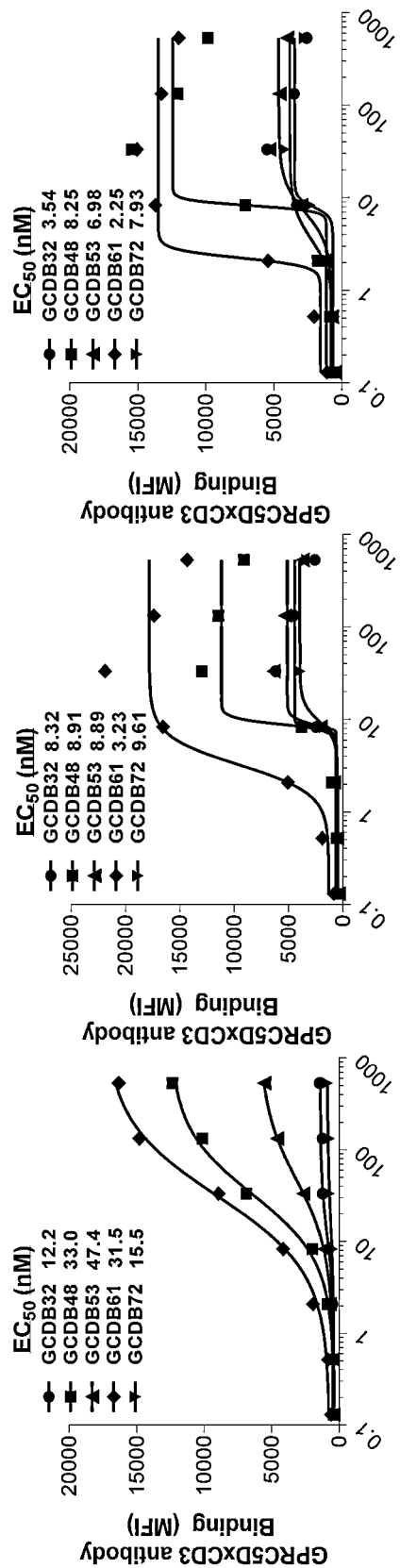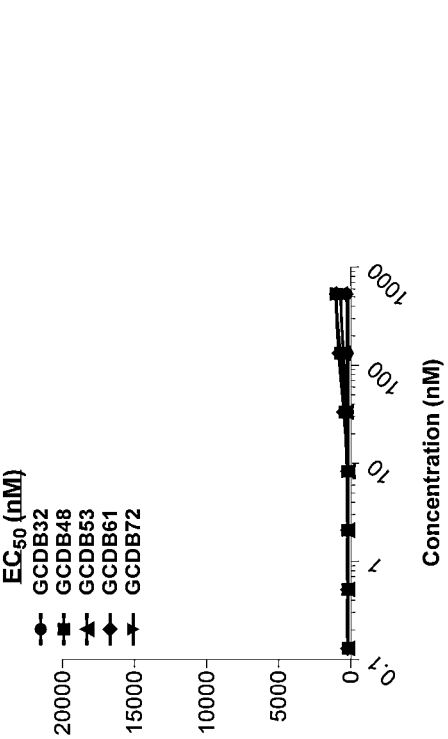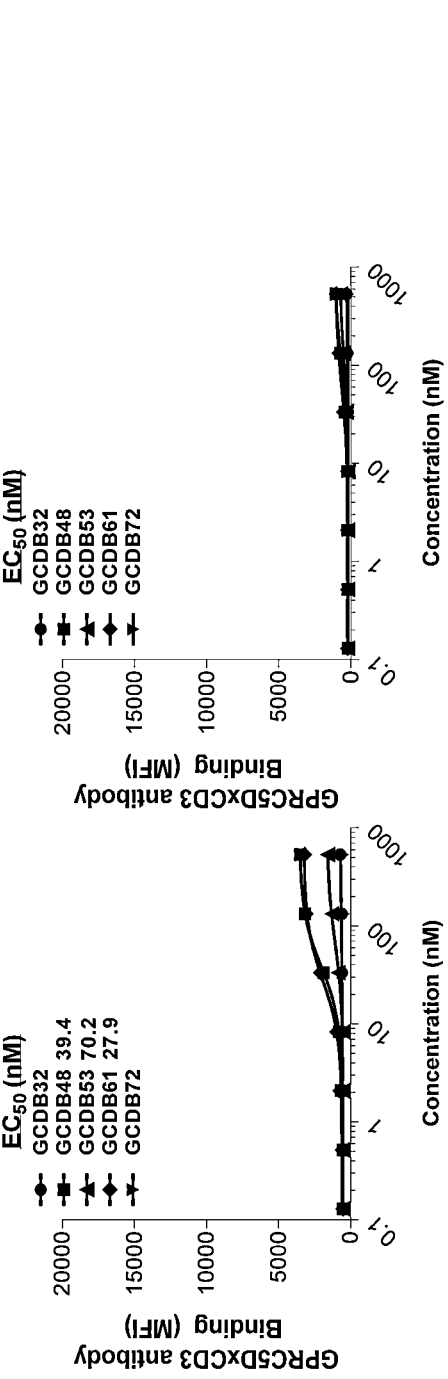
Figure 11A H929
Figure 11B MM.1R
Figure 11C OPM2
Figure 11D LP1
Figure 11E NALM6

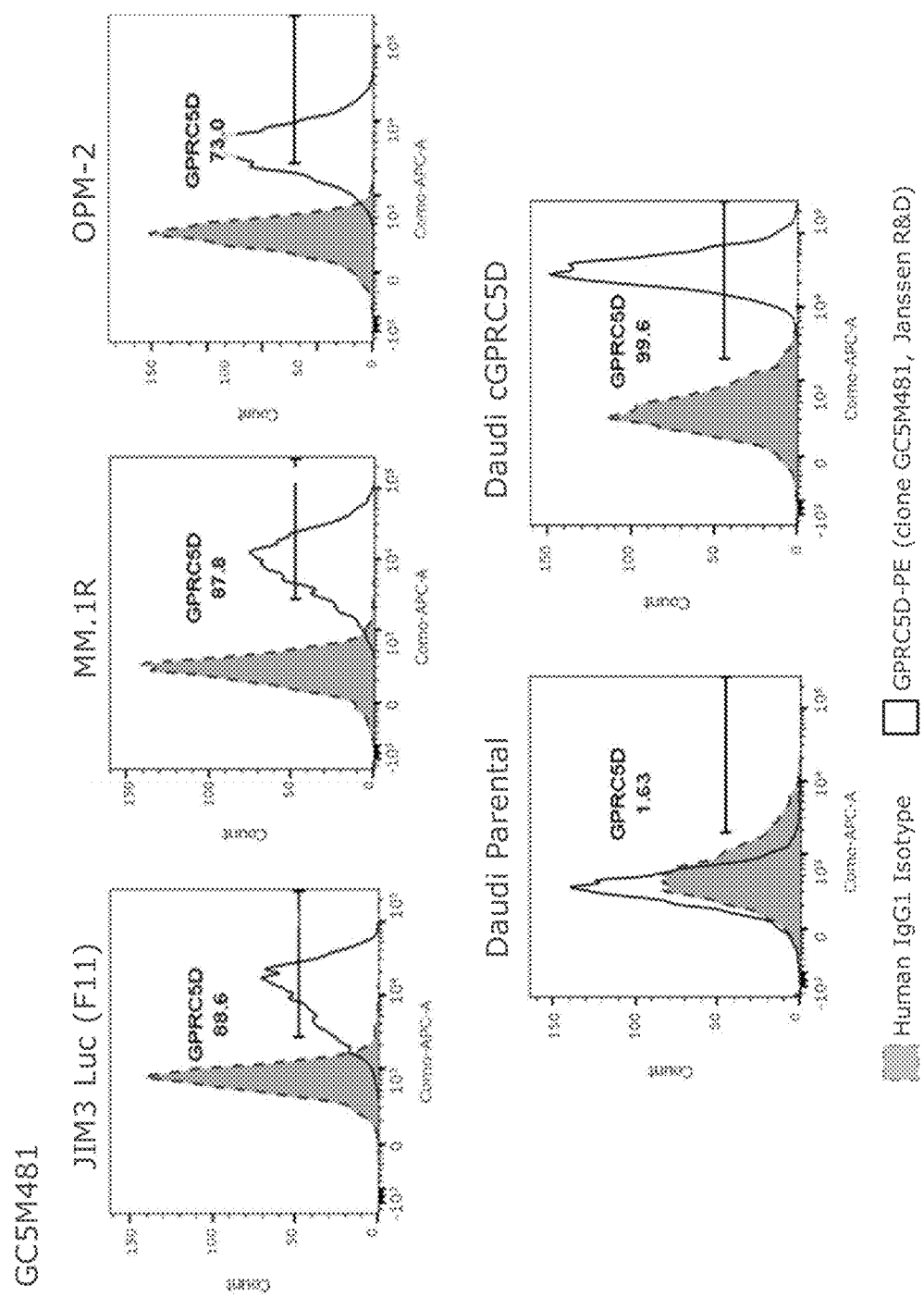
Figure 14A (Contd.)

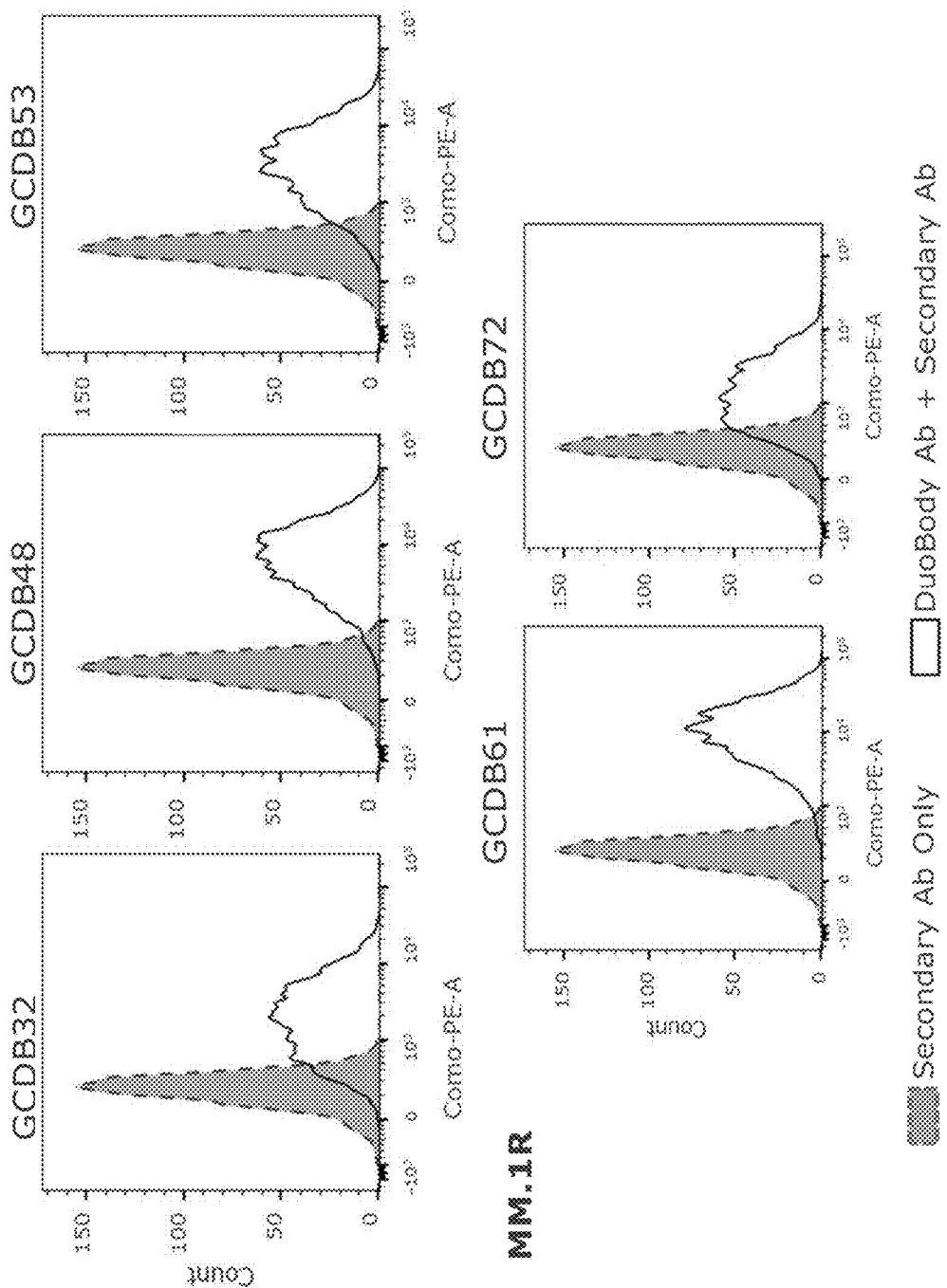
Figure 14B (Contd.)

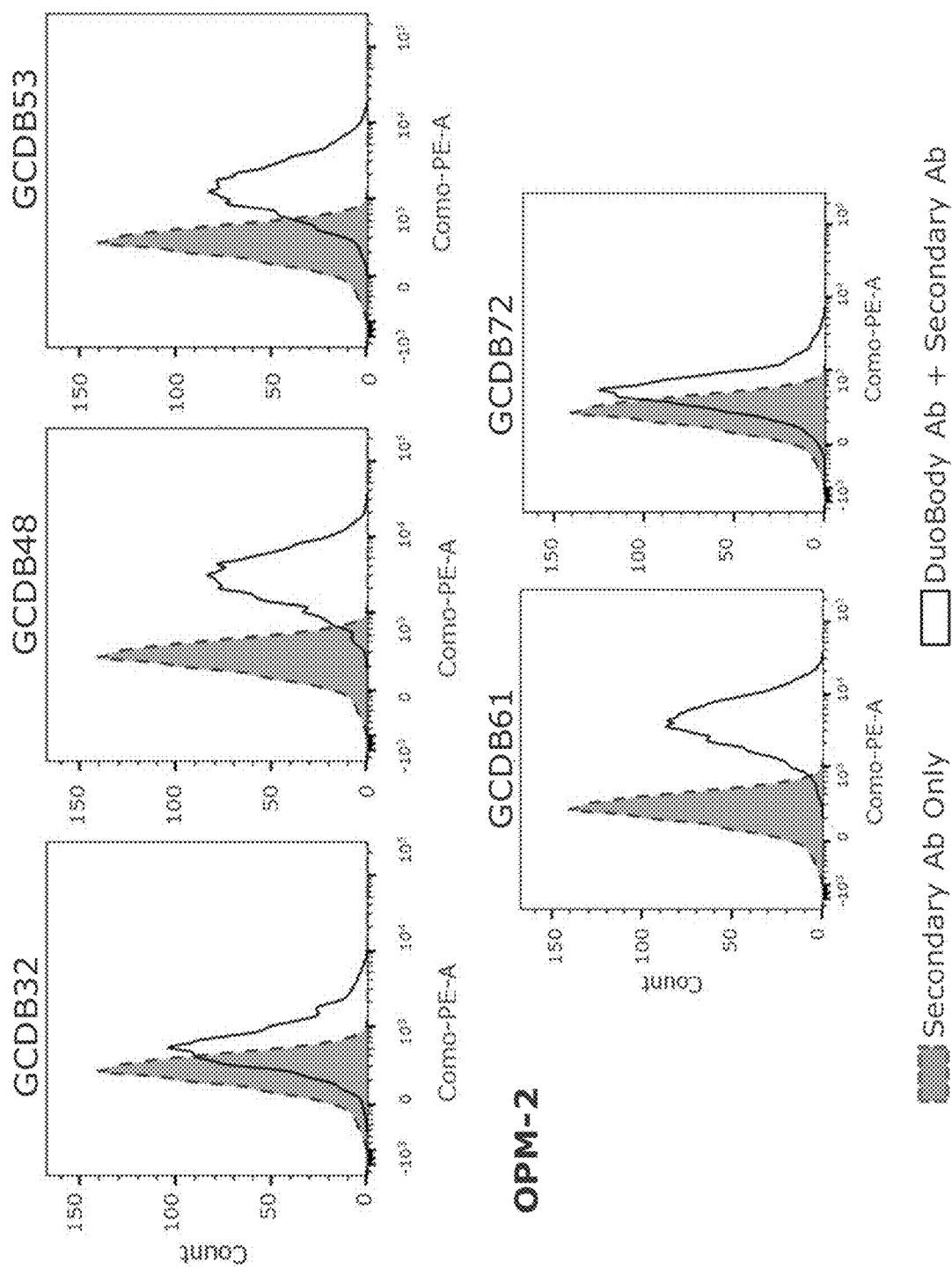
Figure 14B (Contd.)

SEQUENCE LISTING

<160> NUMBER OF SEQ ID NOS: 100

<210> SEQ ID NO 1
<211> LENGTH: 5
<212> TYPE: PRT
<213> ORGANISM: Homo sapiens

<400> SEQUENCE: 1

Ser Tyr Ala Ile Ser
1               5

<210> SEQ ID NO 2
<211> LENGTH: 5
<212> TYPE: PRT
<213> ORGANISM: Homo sapiens

<400> SEQUENCE: 2

Asn Tyr Trp Met Ser
1               5

<210> SEQ ID NO 3
<211> LENGTH: 5
<212> TYPE: PRT
<213> ORGANISM: Homo sapiens

<400> SEQUENCE: 3

Ser Tyr Phe Ile Gly
1               5

<210> SEQ ID NO 4
<211> LENGTH: 5
<212> TYPE: PRT

```
<213> ORGANISM: Homo sapiens

<400> SEQUENCE: 4

Gly Tyr Thr Met Asn
1               5

<210> SEQ ID NO 5
<211> LENGTH: 17
<212> TYPE: PRT
<213> ORGANISM: Homo sapiens

<400> SEQUENCE: 5

Gly Ile Ile Pro Ile Phe Gly Thr Ala Asn Tyr Ala Gln Lys Phe Gln
1               5                   10                  15

Gly

<210> SEQ ID NO 6
<211> LENGTH: 17
<212> TYPE: PRT
<213> ORGANISM: Homo sapiens

<400> SEQUENCE: 6

Gly Ile Ser Tyr Ser Gly Gly Ser Lys Tyr Tyr Ala Ser Ser Val Lys
1               5                   10                  15

Gly

<210> SEQ ID NO 7
<211> LENGTH: 17
<212> TYPE: PRT
<213> ORGANISM: Homo sapiens

<400> SEQUENCE: 7

Ile Ile Tyr Pro Gly Lys Ser Asp Thr Arg Tyr Ser Pro Ser Phe Gln
1               5                   10                  15

Gly

<210> SEQ ID NO 8
<211> LENGTH: 17
<212> TYPE: PRT
<213> ORGANISM: Homo sapiens

<400> SEQUENCE: 8

Leu Ile Asn Pro Tyr Asn Ser Asp Thr Asn Tyr Ala Gln Lys Leu Gln
1               5                   10                  15

Gly

<210> SEQ ID NO 9
<211> LENGTH: 10
<212> TYPE: PRT
<213> ORGANISM: Homo sapiens

<400> SEQUENCE: 9

Glu Ser Arg Trp Arg Gly Tyr Lys Leu Asp
1               5                   10

<210> SEQ ID NO 10
<211> LENGTH: 13
<212> TYPE: PRT
<213> ORGANISM: Homo sapiens

<400> SEQUENCE: 10

Ala Ala Phe Asp Phe Gly Arg Arg Ala Val Arg Leu Asp
```

```
1               5                   10
```

<210> SEQ ID NO 11
<211> LENGTH: 14
<212> TYPE: PRT
<213> ORGANISM: Homo sapiens

<400> SEQUENCE: 11

```
Val Tyr Ser Phe Gly Gly Arg His Lys Ala Leu Phe Asp Tyr
1               5                   10
```

<210> SEQ ID NO 12
<211> LENGTH: 9
<212> TYPE: PRT
<213> ORGANISM: Homo sapiens

<400> SEQUENCE: 12

```
Val Ala Leu Arg Val Ala Leu Asp Tyr
1               5
```

<210> SEQ ID NO 13
<211> LENGTH: 11
<212> TYPE: PRT
<213> ORGANISM: Homo sapiens

<400> SEQUENCE: 13

```
Arg Ala Ser Gln Ser Ile Ser Ser Tyr Leu Asn
1               5                   10
```

<210> SEQ ID NO 14
<211> LENGTH: 11
<212> TYPE: PRT
<213> ORGANISM: Homo sapiens

<400> SEQUENCE: 14

```
Arg Ala Ser Gln Ser Val Ser Ser Tyr Leu Ala
1               5                   10
```

<210> SEQ ID NO 15
<211> LENGTH: 11
<212> TYPE: PRT
<213> ORGANISM: Homo sapiens

<400> SEQUENCE: 15

```
Lys Ala Ser Gln Asn Val Ala Thr His Val Gly
1               5                   10
```

<210> SEQ ID NO 16
<211> LENGTH: 7
<212> TYPE: PRT
<213> ORGANISM: Homo sapiens

<400> SEQUENCE: 16

```
Ala Ala Ser Ser Leu Gln Ser
1               5
```

<210> SEQ ID NO 17
<211> LENGTH: 7
<212> TYPE: PRT
<213> ORGANISM: Homo sapiens

<400> SEQUENCE: 17

```
Asp Ala Ser Asn Arg Ala Thr
1               5
```

<210> SEQ ID NO 18
<211> LENGTH: 7
<212> TYPE: PRT
<213> ORGANISM: Homo sapiens

<400> SEQUENCE: 18

Ser Ala Ser Tyr Arg Tyr Ser
1               5

<210> SEQ ID NO 19
<211> LENGTH: 9
<212> TYPE: PRT
<213> ORGANISM: Homo sapiens

<400> SEQUENCE: 19

Gln Gln Ser Tyr Ser Thr Pro Leu Thr
1               5

<210> SEQ ID NO 20
<211> LENGTH: 9
<212> TYPE: PRT
<213> ORGANISM: Homo sapiens

<400> SEQUENCE: 20

Gln Gln Arg Ser Asn Trp Pro Leu Thr
1               5

<210> SEQ ID NO 21
<211> LENGTH: 9
<212> TYPE: PRT
<213> ORGANISM: Homo sapiens

<400> SEQUENCE: 21

Gln Gln Tyr Asn Arg Tyr Pro Tyr Thr
1               5

<210> SEQ ID NO 22
<211> LENGTH: 345
<212> TYPE: PRT
<213> ORGANISM: Homo sapiens

<400> SEQUENCE: 22

Met Tyr Lys Asp Cys Ile Glu Ser Thr Gly Asp Tyr Phe Leu Leu Cys
1               5                   10                  15

Asp Ala Glu Gly Pro Trp Gly Ile Ile Leu Glu Ser Leu Ala Ile Leu
                20                  25                  30

Gly Ile Val Val Thr Ile Leu Leu Leu Ala Phe Leu Phe Leu Met
            35                  40                  45

Arg Lys Ile Gln Asp Cys Ser Gln Trp Asn Val Leu Pro Thr Gln Leu
    50                  55                  60

Leu Phe Leu Leu Ser Val Leu Gly Leu Phe Gly Leu Ala Phe Ala Phe
65                  70                  75                  80

Ile Ile Glu Leu Asn Gln Gln Thr Ala Pro Val Arg Tyr Phe Leu Phe
                85                  90                  95

Gly Val Leu Phe Ala Leu Cys Phe Ser Cys Leu Leu Ala His Ala Ser
                100                 105                 110

Asn Leu Val Lys Leu Val Arg Gly Cys Val Ser Phe Ser Trp Thr Thr
            115                 120                 125

Ile Leu Cys Ile Ala Ile Gly Cys Ser Leu Leu Gln Ile Ile Ala
            130                 135                 140

Thr Glu Tyr Val Thr Leu Ile Met Thr Arg Gly Met Met Phe Val Asn
145                 150                 155                 160

Met Thr Pro Cys Gln Leu Asn Val Asp Phe Val Val Leu Leu Val Tyr
                165                 170                 175

Val Leu Phe Leu Met Ala Leu Thr Phe Phe Val Ser Lys Ala Thr Phe
            180                 185                 190

Cys Gly Pro Cys Glu Asn Trp Lys Gln His Gly Arg Leu Ile Phe Ile
        195                 200                 205

Thr Val Leu Phe Ser Ile Ile Ile Trp Val Val Trp Ile Ser Met Leu
210                 215                 220

Leu Arg Gly Asn Pro Gln Phe Gln Arg Gln Pro Gln Trp Asp Asp Pro
225                 230                 235                 240

Val Val Cys Ile Ala Leu Val Thr Asn Ala Trp Val Phe Leu Leu Leu
                245                 250                 255

Tyr Ile Val Pro Glu Leu Cys Ile Leu Tyr Arg Ser Cys Arg Gln Glu
            260                 265                 270

Cys Pro Leu Gln Gly Asn Ala Cys Pro Val Thr Ala Tyr Gln His Ser
        275                 280                 285

Phe Gln Val Glu Asn Gln Glu Leu Ser Arg Ala Arg Asp Ser Asp Gly
290                 295                 300

Ala Glu Glu Asp Val Ala Leu Thr Ser Tyr Gly Thr Pro Ile Gln Pro
305                 310                 315                 320

Gln Thr Val Asp Pro Thr Gln Glu Cys Phe Ile Pro Gln Ala Lys Leu
                325                 330                 335

Ser Pro Gln Gln Asp Ala Gly Gly Val
            340                 345

<210> SEQ ID NO 23
<211> LENGTH: 344
<212> TYPE: PRT
<213> ORGANISM: Macaca fascicularis

<400> SEQUENCE: 23

Met Tyr Lys Asp Cys Ile Glu Ser Thr Gly Asp Tyr Phe Leu Pro Cys
1               5                   10                  15

Asp Ser Glu Gly Pro Trp Gly Ile Val Leu Glu Ser Leu Ala Ile Leu
            20                  25                  30

Gly Ile Val Val Thr Ile Leu Leu Leu Ala Phe Leu Phe Leu Met
        35                  40                  45

Arg Lys Ile Gln Asp Cys Ser Gln Trp Asn Val Leu Pro Thr Gln Leu
50                  55                  60

Leu Phe Leu Leu Ser Val Leu Gly Leu Phe Gly Leu Ala Phe Ala Phe
65                  70                  75                  80

Ile Ile Gln Leu Asn Gln Thr Ala Pro Val Arg Tyr Phe Leu Phe
                85                  90                  95

Gly Val Leu Phe Ala Leu Cys Phe Ser Cys Leu Leu Ala His Ala Ser
            100                 105                 110

Asn Leu Val Lys Leu Val Arg Gly Arg Val Ser Phe Ser Trp Thr Thr
        115                 120                 125

Ile Leu Cys Ile Ala Ile Gly Cys Ser Leu Leu Gln Val Ile Ile Ala
130                 135                 140

Ile Glu Tyr Val Thr Leu Ile Met Thr Arg Gly Met Met Phe Val His
145                 150                 155                 160

Met Thr Pro Tyr Gln Leu Asn Val Asp Phe Val Val Leu Leu Val Tyr
                165                 170                 175

```
Val Leu Phe Leu Met Ala Leu Thr Phe Phe Val Ser Lys Ala Thr Phe
            180                 185                 190

Cys Gly Pro Cys Glu Asn Trp Lys Gln His Gly Arg Leu Ile Phe Ile
            195                 200                 205

Thr Val Leu Phe Ser Ile Ile Ile Trp Val Val Trp Ile Ser Met Leu
    210                 215                 220

Leu Arg Gly Asn Pro Gln Phe Gln Arg Gln Pro Gln Trp Asp Asp Pro
225                 230                 235                 240

Val Val Cys Ile Ala Leu Val Thr Asn Ala Trp Val Phe Leu Leu Leu
                245                 250                 255

Tyr Ile Val Pro Glu Leu Cys Ile Leu Tyr Arg Ser Cys Arg Gln Glu
                260                 265                 270

Cys Pro Ser Gln Gly His Ala Cys Pro Val Thr Ala Tyr Gln Arg Ser
            275                 280                 285

Phe Gln Val Glu Asn Gln Glu Leu Ser Arg Ala Arg Asp Ser Asp Gly
    290                 295                 300

Ala Glu Glu Asp Val Ala Leu Thr Ser Phe Gly Thr Pro Ile Gln Pro
305                 310                 315                 320

Gln Thr Val Asp Pro Thr Gln Glu Cys Phe Ile Pro Arg Ala Lys Leu
                325                 330                 335

Ser Pro Gln Gln Asp Ala Gly Val
            340

<210> SEQ ID NO 24
<211> LENGTH: 344
<212> TYPE: PRT
<213> ORGANISM: Mus sp.

<400> SEQUENCE: 24

Met Tyr Glu Asp Cys Val Lys Ser Thr Glu Asp Tyr Tyr Leu Phe Cys
1               5                   10                  15

Asp Asn Glu Gly Pro Trp Ala Ile Val Leu Glu Ser Leu Ala Val Ile
            20                  25                  30

Gly Ile Val Val Thr Ile Leu Leu Leu Ala Phe Leu Phe Leu Met
            35                  40                  45

Arg Lys Val Gln Asp Cys Ser Gln Trp Asn Val Leu Pro Thr Gln Phe
    50                  55                  60

Leu Phe Leu Leu Ala Val Leu Gly Leu Phe Gly Leu Thr Phe Ala Phe
65                  70                  75                  80

Ile Ile Gln Leu Asn His Gln Thr Ala Pro Val Arg Tyr Phe Leu Phe
                85                  90                  95

Gly Val Leu Phe Ala Ile Cys Phe Ser Cys Leu Leu Ala His Ala Ser
            100                 105                 110

Asn Leu Val Lys Leu Val Arg Gly Arg Val Ser Phe Cys Trp Thr Thr
        115                 120                 125

Ile Leu Phe Ile Ala Ile Gly Val Ser Leu Leu Gln Thr Ile Ile Ala
    130                 135                 140

Ile Glu Tyr Val Thr Leu Ile Met Thr Arg Gly Leu Met Phe Glu His
145                 150                 155                 160

Met Thr Pro Tyr Gln Leu Asn Val Asp Phe Val Cys Leu Leu Ile Tyr
                165                 170                 175

Val Leu Phe Leu Met Ala Leu Thr Phe Phe Val Ser Lys Ala Thr Phe
            180                 185                 190

Cys Gly Pro Cys Glu Asn Trp Lys Gln His Gly Arg Leu Ile Phe Ala
```

```
                195                 200                 205
Thr Val Leu Val Ser Ile Ile Ile Trp Val Trp Ile Ser Met Leu
210                 215                 220

Leu Arg Gly Asn Pro Gln Leu Arg Gln Pro His Trp Asp Asp Ala
225                 230                 235                 240

Val Ile Cys Ile Gly Leu Val Thr Asn Ala Trp Val Phe Leu Leu Ile
                245                 250                 255

Tyr Ile Ile Pro Glu Leu Ser Ile Leu Tyr Arg Ser Cys Arg Gln Glu
                260                 265                 270

Cys Pro Thr Gln Gly Asn Val Cys Gln Val Pro Val Tyr Gln Arg Ser
                275                 280                 285

Phe Arg Met Asp Thr Gln Glu Pro Thr Arg Ala Arg Asp Ser Asp Gly
290                 295                 300

Ala Gln Glu Asp Val Ala Leu Thr Ala Tyr Gly Thr Pro Ile Gln Leu
305                 310                 315                 320

Gln Ser Ala Asp Pro Ser Arg Glu Tyr Leu Ile Pro Ser Ala Thr Leu
                325                 330                 335

Ser Pro Gln Gln Asp Ala Gly Leu
                340

<210> SEQ ID NO 25
<211> LENGTH: 125
<212> TYPE: PRT
<213> ORGANISM: Homo sapiens

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Ala
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 26
<211> LENGTH: 109
<212> TYPE: PRT
<213> ORGANISM: Homo sapiens

<400> SEQUENCE: 26

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Gly Thr Pro Ala Arg Phe
```

```
                    50                  55                  60
Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu
            100                 105
```

<210> SEQ ID NO 27
<211> LENGTH: 5
<212> TYPE: PRT
<213> ORGANISM: Homo sapiens

<400> SEQUENCE: 27

```
Ser Tyr Trp Ile Gly
 1               5
```

<210> SEQ ID NO 28
<211> LENGTH: 17
<212> TYPE: PRT
<213> ORGANISM: Homo sapiens

<400> SEQUENCE: 28

```
Gly Ile Ser Tyr Ser Gly Gly Ser Lys Tyr Tyr Ala Asp Ser Val Lys
 1               5                  10                  15

Gly
```

<210> SEQ ID NO 29
<211> LENGTH: 17
<212> TYPE: PRT
<213> ORGANISM: Homo sapiens

<400> SEQUENCE: 29

```
Ile Ile Tyr Pro Gly Asp Ser Asp Thr Arg Tyr Ser Pro Ser Phe Gln
 1               5                  10                  15

Gly
```

<210> SEQ ID NO 30
<211> LENGTH: 14
<212> TYPE: PRT
<213> ORGANISM: Homo sapiens

<400> SEQUENCE: 30

```
Ala Ala Trp Asp Phe Gly Arg Arg Ala Val Arg Leu Asp Tyr
 1               5                  10
```

<210> SEQ ID NO 31
<211> LENGTH: 11
<212> TYPE: PRT
<213> ORGANISM: Homo sapiens

<400> SEQUENCE: 31

```
Glu Ser Arg Tyr Arg Gly Tyr Lys Leu Asp Tyr
 1               5                  10
```

<210> SEQ ID NO 32
<211> LENGTH: 11
<212> TYPE: PRT
<213> ORGANISM: Homo sapiens

<400> SEQUENCE: 32

```
Glu Ser Arg Val Arg Gly Tyr Lys Leu Asp Tyr
```

<210> SEQ ID NO 33
<211> LENGTH: 11
<212> TYPE: PRT
<213> ORGANISM: Homo sapiens

<400> SEQUENCE: 33

Glu Ser Arg Gly Arg Gly Tyr Lys Leu Asp Tyr
1               5                   10

<210> SEQ ID NO 34
<211> LENGTH: 11
<212> TYPE: PRT
<213> ORGANISM: Homo sapiens

<400> SEQUENCE: 34

Glu Ser Arg Ala Arg Gly Tyr Lys Leu Asp Tyr
1               5                   10

<210> SEQ ID NO 35
<211> LENGTH: 11
<212> TYPE: PRT
<213> ORGANISM: Homo sapiens

<400> SEQUENCE: 35

Glu Ser Arg Phe Arg Gly Tyr Lys Leu Asp Tyr
1               5                   10

<210> SEQ ID NO 36
<211> LENGTH: 5
<212> TYPE: PRT
<213> ORGANISM: Homo sapiens

<400> SEQUENCE: 36

Ser Tyr Tyr Ile Gly
1               5

<210> SEQ ID NO 37
<211> LENGTH: 5
<212> TYPE: PRT
<213> ORGANISM: Homo sapiens

<400> SEQUENCE: 37

Ser Tyr Val Ile Gly
1               5

<210> SEQ ID NO 38
<211> LENGTH: 5
<212> TYPE: PRT
<213> ORGANISM: Homo sapiens

<400> SEQUENCE: 38

Ser Tyr Gly Ile Gly
1               5

<210> SEQ ID NO 39
<211> LENGTH: 5
<212> TYPE: PRT
<213> ORGANISM: Homo sapiens

<400> SEQUENCE: 39

Ser Tyr Ala Ile Gly
1               5

<210> SEQ ID NO 40
<211> LENGTH: 17
<212> TYPE: PRT
<213> ORGANISM: Homo sapiens

<400> SEQUENCE: 40

Ile Ile Tyr Pro Gly Ala Ser Asp Thr Arg Tyr Ser Pro Ser Phe Gln
1               5                   10                  15
Gly

<210> SEQ ID NO 41
<211> LENGTH: 17
<212> TYPE: PRT
<213> ORGANISM: Homo sapiens

<400> SEQUENCE: 41

Ile Ile Tyr Pro Gly Ser Ser Asp Thr Arg Tyr Ser Pro Ser Phe Gln
1               5                   10                  15
Gly

<210> SEQ ID NO 42
<211> LENGTH: 17
<212> TYPE: PRT
<213> ORGANISM: Homo sapiens

<400> SEQUENCE: 42

Ile Ile Tyr Pro Gly Glu Ser Asp Thr Arg Tyr Ser Pro Ser Phe Gln
1               5                   10                  15
Gly

<210> SEQ ID NO 43
<211> LENGTH: 17
<212> TYPE: PRT
<213> ORGANISM: Homo sapiens

<400> SEQUENCE: 43

Ile Ile Tyr Pro Gly Tyr Ser Asp Thr Arg Tyr Ser Pro Ser Phe Gln
1               5                   10                  15
Gly

<210> SEQ ID NO 44
<211> LENGTH: 17
<212> TYPE: PRT
<213> ORGANISM: Homo sapiens

<400> SEQUENCE: 44

Gly Ile Ser Tyr Ser Gly Gly Ser Lys Tyr Tyr Ala Ala Ser Val Lys
1               5                   10                  15
Gly

<210> SEQ ID NO 45
<211> LENGTH: 17
<212> TYPE: PRT
<213> ORGANISM: Homo sapiens

<400> SEQUENCE: 45

Gly Ile Ser Tyr Ser Gly Gly Ser Lys Tyr Tyr Ala Lys Ser Val Lys
1               5                   10                  15
Gly

-continued

```
<210> SEQ ID NO 46
<211> LENGTH: 17
<212> TYPE: PRT
<213> ORGANISM: Homo sapiens

<400> SEQUENCE: 46

Gly Ile Ser Tyr Ser Gly Gly Ser Lys Tyr Tyr Ala Glu Ser Val Lys
1               5                   10                  15

Gly

<210> SEQ ID NO 47
<211> LENGTH: 17
<212> TYPE: PRT
<213> ORGANISM: Homo sapiens

<400> SEQUENCE: 47

Gly Ile Ser Tyr Ser Gly Gly Ser Lys Tyr Tyr Ala Tyr Ser Val Lys
1               5                   10                  15

Gly

<210> SEQ ID NO 48
<211> LENGTH: 14
<212> TYPE: PRT
<213> ORGANISM: Homo sapiens

<400> SEQUENCE: 48

Ala Ala Tyr Asp Phe Gly Arg Arg Ala Val Arg Leu Asp Tyr
1               5                   10

<210> SEQ ID NO 49
<211> LENGTH: 14
<212> TYPE: PRT
<213> ORGANISM: Homo sapiens

<400> SEQUENCE: 49

Ala Ala Val Asp Phe Gly Arg Arg Ala Val Arg Leu Asp Tyr
1               5                   10

<210> SEQ ID NO 50
<211> LENGTH: 14
<212> TYPE: PRT
<213> ORGANISM: Homo sapiens

<400> SEQUENCE: 50

Ala Ala Gly Asp Phe Gly Arg Arg Ala Val Arg Leu Asp Tyr
1               5                   10

<210> SEQ ID NO 51
<211> LENGTH: 14
<212> TYPE: PRT
<213> ORGANISM: Homo sapiens

<400> SEQUENCE: 51

Ala Ala Ala Asp Phe Gly Arg Arg Ala Val Arg Leu Asp Tyr
1               5                   10

<210> SEQ ID NO 52
<211> LENGTH: 120
<212> TYPE: PRT
<213> ORGANISM: Homo sapiens

<400> SEQUENCE: 52

Gln Val Gln Leu Val Gln Ser Gly Ala Glu Val Lys Lys Pro Gly Ser
1               5                   10                  15
```

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Arg Trp Arg Gly Tyr Lys Leu Asp Tyr Trp Gly Gln
            100                 105                 110

Gly Thr Leu Val Thr Val Ser Ser
            115                 120

<210> SEQ ID NO 53
<211> LENGTH: 123
<212> TYPE: PRT
<213> ORGANISM: Homo sapiens

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ser Gly Ile Ser Tyr Ser Gly Ser Lys Tyr Tyr Ala Ser Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ala Phe Asp Phe Gly Arg Arg Ala Val Arg Leu Asp Tyr
            100                 105                 110

Trp Gly Gln Gly Thr Leu Val Thr Val Ser Ser
            115                 120

<210> SEQ ID NO 54
<211> LENGTH: 123
<212> TYPE: PRT
<213> ORGANISM: Homo sapiens

<400> SEQUENCE: 54

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Phe Ile Gly Trp Val Arg Gln Met Pro Gly Lys Gly Leu Glu Trp Met
        35                  40                  45

Gly Ile Ile Tyr Pro Gly Lys Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Tyr Ser Phe Gly Gly Arg His Lys Ala Leu Phe Asp Tyr
            100                 105                 110

Trp Gly Gln Gly Thr Leu Val Thr Val Ser Ser
            115                 120

<210> SEQ ID NO 55
<211> LENGTH: 118
<212> TYPE: PRT
<213> ORGANISM: Homo sapiens

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Thr Met Asn Trp Val Arg Gln Ala Pro Gly Gln Gly Leu Glu Trp Met
            35                  40                  45

Gly Leu Ile Asn Pro Tyr Asn Ser Asp Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Leu Arg Val Ala Leu Asp Tyr Trp Gly Gln Gly Thr
            100                 105                 110

Leu Val Thr Val Ser Ser
        115

<210> SEQ ID NO 56
<211> LENGTH: 107
<212> TYPE: PRT
<213> ORGANISM: Homo sapiens

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 57
<211> LENGTH: 107
<212> TYPE: PRT
<213> ORGANISM: Homo sapiens

<400> SEQUENCE: 57

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr
                20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 58
<211> LENGTH: 107
<212> TYPE: PRT
<213> ORGANISM: Homo sapiens

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Ala Thr His
                20                  25                  30

Val Gly Trp Tyr Gln Gln Lys Pro Gly Lys Ala Pro Lys Arg Leu Ile
            35                  40                  45

Tyr Ser Ala Ser Tyr Arg Tyr Ser Gly Val Pro Ser Arg Phe Ser Gly
50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Tyr Asn Arg Tyr Pro Tyr
                85                  90                  95

Thr Phe Gly Gln Gly Thr Lys Leu Glu Ile Lys
            100                 105

<210> SEQ ID NO 59
<211> LENGTH: 327
<212> TYPE: PRT
<213> ORGANISM: Homo sapiens

<400> SEQUENCE: 59

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 60
<211> LENGTH: 330
<212> TYPE: PRT
<213> ORGANISM: Homo sapiens

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 61
<211> LENGTH: 5
<212> TYPE: PRT
<213> ORGANISM: Homo sapiens

<400> SEQUENCE: 61

Asp Tyr Gly Met His
1               5

<210> SEQ ID NO 62
<211> LENGTH: 5
<212> TYPE: PRT
<213> ORGANISM: Homo sapiens

<400> SEQUENCE: 62

Gly Tyr Ala Met Ser
1               5

<210> SEQ ID NO 63
<211> LENGTH: 5
<212> TYPE: PRT
<213> ORGANISM: Homo sapiens

<400> SEQUENCE: 63

Ser Tyr Gly Ile Ser
1               5

<210> SEQ ID NO 64
<211> LENGTH: 10
<212> TYPE: PRT
<213> ORGANISM: Homo sapiens

<400> SEQUENCE: 64

Gly Tyr Ser Phe Thr Gly Tyr Thr Met Asn
1               5                   10

<210> SEQ ID NO 65
<211> LENGTH: 5
<212> TYPE: PRT

<213> ORGANISM: Homo sapiens

<400> SEQUENCE: 65

Ser Tyr Ala Met Ser
1               5

<210> SEQ ID NO 66
<211> LENGTH: 10
<212> TYPE: PRT
<213> ORGANISM: Homo sapiens

<400> SEQUENCE: 66

Gly Phe Ser Leu Thr Ser Tyr Asn Val His
1               5                   10

<210> SEQ ID NO 67
<211> LENGTH: 17
<212> TYPE: PRT
<213> ORGANISM: Homo sapiens

<400> SEQUENCE: 67

Ala Ile Lys Tyr Ser Gly Gly Ser Thr Tyr Tyr Ala Asp Ser Val Lys
1               5                   10                  15

Gly

<210> SEQ ID NO 68
<211> LENGTH: 17
<212> TYPE: PRT
<213> ORGANISM: Homo sapiens

<400> SEQUENCE: 68

Ala Ile Ser Gly Ser Gly Gly Ser Thr Tyr Tyr Ala Asp Ser Val Lys
1               5                   10                  15

Gly

<210> SEQ ID NO 69
<211> LENGTH: 17
<212> TYPE: PRT
<213> ORGANISM: Homo sapiens

<400> SEQUENCE: 69

Gly Ile Ile Pro Ile Phe Gly Asn Ile Asn Tyr Ala Gln Lys Phe Gln
1               5                   10                  15

Gly

<210> SEQ ID NO 70
<211> LENGTH: 10
<212> TYPE: PRT
<213> ORGANISM: Homo sapiens

<400> SEQUENCE: 70

Leu Ile Asn Pro Tyr Asn Gly Asp Thr Asn
1               5                   10

<210> SEQ ID NO 71
<211> LENGTH: 16
<212> TYPE: PRT
<213> ORGANISM: Homo sapiens

<400> SEQUENCE: 71

Val Ile Trp Ala Gly Gly Ser Thr Asn Tyr Asn Ser Ala Leu Met Ser
1               5                   10                  15

<210> SEQ ID NO 72
<211> LENGTH: 10
<212> TYPE: PRT
<213> ORGANISM: Homo sapiens

<400> SEQUENCE: 72

Arg Ala Glu Ser Gly Pro Gly Leu Asp Tyr
1               5                   10

<210> SEQ ID NO 73
<211> LENGTH: 13
<212> TYPE: PRT
<213> ORGANISM: Homo sapiens

<400> SEQUENCE: 73

Ile Gly Phe Tyr Gly Arg Ser Phe Arg Ile Phe Asp Tyr
1               5                   10

<210> SEQ ID NO 74
<211> LENGTH: 14
<212> TYPE: PRT
<213> ORGANISM: Homo sapiens

<400> SEQUENCE: 74

Val Asp Arg Ser Phe Gly Arg Ser Arg Tyr Thr Leu Asp Tyr
1               5                   10

<210> SEQ ID NO 75
<211> LENGTH: 14
<212> TYPE: PRT
<213> ORGANISM: Homo sapiens

<400> SEQUENCE: 75

Val Ser Arg Arg Phe Lys Arg Phe Ala Tyr Tyr Phe Asp Tyr
1               5                   10

<210> SEQ ID NO 76
<211> LENGTH: 10
<212> TYPE: PRT
<213> ORGANISM: Homo sapiens

<400> SEQUENCE: 76

Ser Asn Phe Leu Pro Val Val Phe Asp Tyr
1               5                   10

<210> SEQ ID NO 77
<211> LENGTH: 9
<212> TYPE: PRT
<213> ORGANISM: Homo sapiens

<400> SEQUENCE: 77

Asp Gly Ile Arg Leu Arg Phe Ala Tyr
1               5

<210> SEQ ID NO 78
<211> LENGTH: 7
<212> TYPE: PRT
<213> ORGANISM: Homo sapiens

<400> SEQUENCE: 78

Trp Ala Ser Thr Arg Glu Ser
1               5

<210> SEQ ID NO 79

```
<211> LENGTH: 7
<212> TYPE: PRT
<213> ORGANISM: Homo sapiens

<400> SEQUENCE: 79

Thr Ala Ser Asn Arg Ala Thr
1               5

<210> SEQ ID NO 80
<211> LENGTH: 9
<212> TYPE: PRT
<213> ORGANISM: Homo sapiens

<400> SEQUENCE: 80

Gln Gln Tyr Tyr Ser Thr Pro Leu Thr
1               5

<210> SEQ ID NO 81
<211> LENGTH: 9
<212> TYPE: PRT
<213> ORGANISM: Homo sapiens

<400> SEQUENCE: 81

Gln Gln Tyr Phe Arg Ala Pro Ile Thr
1               5

<210> SEQ ID NO 82
<211> LENGTH: 119
<212> TYPE: PRT
<213> ORGANISM: Homo sapiens

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ser Ala Ile Lys Tyr Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ala Glu Ser Gly Pro Gly Leu Asp Tyr Trp Gly Gln Gly
            100                 105                 110

Thr Leu Val Thr Val Ser Ser
        115

<210> SEQ ID NO 83
<211> LENGTH: 123
<212> TYPE: PRT
<213> ORGANISM: Homo sapiens

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45
```

```
Ser Gly Ile Ser Tyr Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ala Trp Asp Phe Gly Arg Arg Ala Val Arg Leu Asp Tyr
            100                 105                 110

Trp Gly Gln Gly Thr Leu Val Thr Val Ser Ser
            115                 120
```

<210> SEQ ID NO 84
<211> LENGTH: 122
<212> TYPE: PRT
<213> ORGANISM: Homo sapiens

<400> SEQUENCE: 84

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ile Gly Phe Tyr Gly Arg Ser Phe Arg Ile Phe Asp Tyr Trp
            100                 105                 110

Gly Gln Gly Thr Leu Val Thr Val Ser Ser
            115                 120
```

<210> SEQ ID NO 85
<211> LENGTH: 123
<212> TYPE: PRT
<213> ORGANISM: Homo sapiens

<400> SEQUENCE: 85

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Tyr Ser Phe Gly Gly Arg His Lys Ala Leu Phe Asp Tyr
            100                 105                 110

Trp Gly Gln Gly Thr Leu Val Thr Val Ser Ser
            115                 120
```

<210> SEQ ID NO 86
<211> LENGTH: 123
<212> TYPE: PRT
<213> ORGANISM: Homo sapiens

<400> SEQUENCE: 86

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Asp Arg Ser Phe Gly Arg Ser Tyr Thr Leu Asp Tyr
            100                 105                 110

Trp Gly Gln Gly Thr Leu Val Thr Val Ser Ser
            115                 120
```

<210> SEQ ID NO 87
<211> LENGTH: 123
<212> TYPE: PRT
<213> ORGANISM: Homo sapiens

<400> SEQUENCE: 87

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Asn Ile Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ser Arg Arg Phe Lys Arg Phe Ala Tyr Tyr Phe Asp Tyr
            100                 105                 110

Trp Gly Gln Gly Thr Leu Val Thr Val Ser Ser
            115                 120
```

<210> SEQ ID NO 88
<211> LENGTH: 118
<212> TYPE: PRT
<213> ORGANISM: Homo sapiens

<400> SEQUENCE: 88

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30
```

Thr Met Asn Trp Val Arg Gln Ala Pro Gly Gln Gly Leu Glu Trp Met
        35                  40                  45

Gly Leu Ile Asn Pro Tyr Asn Gly Asp Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Val Ala Leu Arg Val Ala Leu Asp Tyr Trp Gly Gln Gly Thr
                100                 105                 110

Leu Val Thr Val Ser Ser
        115

<210> SEQ ID NO 89
<211> LENGTH: 119
<212> TYPE: PRT
<213> ORGANISM: Homo sapiens

<400> SEQUENCE: 89

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ser Asn Phe Leu Pro Val Val Phe Asp Tyr Trp Gly Gln Gly
                100                 105                 110

Thr Leu Val Thr Val Ser Ser
        115

<210> SEQ ID NO 90
<211> LENGTH: 705
<212> TYPE: DNA
<213> ORGANISM: Homo sapiens

<400> SEQUENCE: 90
atgcgggtgc tggcccagct gctgggactg ctgctgctgt gcttccctgg cgccagatgc      60
gacatccaga tgacccagag ccccagcagc ctgagcgcca gcgtgggcga ccgggtgacc     120
atcacctgca aggccagcca gaacgtggcc acccacgtgg ctggtacca gcagaagccc     180 ggcaaggccc ccaagcggct gatctacagc gccagctacc ggtacagcgg cgtgcccagc     240
cggttcagcg gcagcggcag cggcaccgag ttcaccctga ccatcagcaa cctgcagccc     300
gaggacttcg ccacctacta ctgccagcag tacaaccggt accctacac cttcggccag     360 ggcaccaagc tggagatcaa gcgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg    600 ctgagcaaag cagactacga gaaacacaaa gtctacgcct gcgaagtcac ccatcagggc     660
ctgagctcgc ccgtcacaaa gagcttcaac agggagagt gttga                                     705

<210> SEQ ID NO 91
<211> LENGTH: 117
<212> TYPE: PRT
<213> ORGANISM: Homo sapiens

<400> SEQUENCE: 91

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Tyr
            20                  25                  30

Asn Val His Trp Ile Arg Gln Pro Pro Gly Lys Ala Leu Glu Trp Leu
        35                  40                  45

Ala Val Ile Trp Ala Gly Gly Ser Thr Asn Tyr Asn Ser Ala Leu Met
    50                  55                  60

Ser Arg Leu Thr Ile Ser Lys Asp Thr Ser Lys Ser Gln Val Val Leu
65                  70                  75                  80

Thr Met Thr Asn Met Arg Ala Glu Asp Thr Ala Thr Tyr Tyr Cys Ala
                85                  90                  95

Arg Asp Gly Ile Arg Leu Arg Phe Ala Tyr Trp Gly Gln Gly Thr Leu
            100                 105                 110

Val Thr Val Ser Ser
        115

<210> SEQ ID NO 92
<211> LENGTH: 113
<212> TYPE: PRT
<213> ORGANISM: Homo sapiens

<400> SEQUENCE: 92

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 93
<211> LENGTH: 108
<212> TYPE: PRT
<213> ORGANISM: Homo sapiens

<400> SEQUENCE: 93

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Lys Ser
            20                  25                  30

Leu Ala Trp Tyr Gln Gln Lys Pro Gly Gln Ala Pro Arg Leu Leu Ile
        35                  40                  45

Tyr Thr Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Phe Arg Ala Pro Ile
                85                  90                  95

Thr Phe Gly Gln Gly Thr Lys Val Glu Ile Lys Lys
            100                 105

<210> SEQ ID NO 94
<211> LENGTH: 107
<212> TYPE: PRT
<213> ORGANISM: Homo sapiens

<400> SEQUENCE: 94

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Ala Thr His
            20                  25                  30

Val Gly Trp Tyr Gln Gln Lys Pro Gly Gln Ala Pro Arg Leu Leu Ile
        35                  40                  45

Tyr Ser Ala Ser Tyr Arg Tyr Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Arg Tyr Pro Tyr
                85                  90                  95

Thr Phe Gly Gln Gly Thr Lys Leu Glu Ile Lys
            100                 105

<210> SEQ ID NO 95
<211> LENGTH: 11
<212> TYPE: PRT
<213> ORGANISM: Homo sapiens

<400> SEQUENCE: 95

Arg Ala Ser Gln Ser Val Arg Lys Ser Leu Ala
1               5                   10

<210> SEQ ID NO 96
<211> LENGTH: 1395
<212> TYPE: DNA
<213> ORGANISM: Homo sapiens

<400> SEQUENCE: 96
atggcctggg tctggaccct gctgttcctg atggccgctg cccagagcat ccaggcccag     60
gtgcagctgg tgcagagcgg cgccgaggtg aagaagcccg cgccagcgt gaaggtgagc    120 tgcaaggcca gcggctacag cttcaccggc tacaccatga actgggtgcg gcaggcccc    180 ggccagggcc tggagtggat gggcctgatc aaccctaca acagcgacac caactacgcc    240
cagaagctgc agggccgggt gaccatgacc accgacacca gcaccagcac cgcctacatg    300
gagctgcgga gcctgcggag cgacgacacc gccgtgtact actgcgcccg ggtggccctg    360
cgggtggccc tggactactg gggccagggc accctggtga ccgtgagcag cgcctccacc    420
aagggcccat ccgtcttccc cctggcgccc tgctccagga gcacctccga gagcacagcc    480

```
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacgaaaac ctacacctgc    660
aacgtagatc acaagcccag caacaccaag gtggacaaga gagttgagtc caaatatggt    720
cccccatgcc caccatgccc agcacctgag gccgccgggg gaccatcagt cttcctgttc    780
cccccaaaac ccaaggacac tctcatgatc tcccggaccc ctgaggtcac gtgcgtggtg    840
gtggacgtga gccaggaaga ccccgaggtc cagttcaact ggtacgtgga tggcgtggag    900
gtgcataatg ccaagacaaa gccgcgggag gagcagttca acagcacgta ccgtgtggtc    960
agcgtcctca ccgtcctgca ccaggactgg ctgaacggca aggagtacaa gtgcaaggtc   1020
tccaacaaag gcctcccgtc ctccatcgag aaaaccatct ccaaagccaa agggcagccc   1080
cgagagccac aggtgtacac cctgccccca tcccaggagg agatgaccaa gaaccaggtc   1140
agcctgacct gcctggtcaa aggcttctac cccagcgaca tcgccgtgga gtgggagagc   1200
aatgggcagc cggagaacaa ctacaagacc acgcctcccg tgctggactc cgacggctcc   1260
ttcttcctct acagcaggct aaccgtggac aagagcaggt ggcaggaggg gaatgtcttc   1320
tcatgctccg tgatgcatga ggctctgcac aaccactaca cacagaagag cctctccctg   1380
tctctgggta aatga                                                    1395
```

<210> SEQ ID NO 97
<211> LENGTH: 14
<212> TYPE: PRT
<213> ORGANISM: Homo sapiens

<400> SEQUENCE: 97

Ala Ala Phe Asp Phe Gly Arg Arg Ala Val Arg Leu Asp Tyr
1               5                   10

<210> SEQ ID NO 98
<211> LENGTH: 17
<212> TYPE: PRT
<213> ORGANISM: Homo sapiens

<400> SEQUENCE: 98

Lys Ser Ser Gln Ser Val Leu Tyr Ser Ser Asn Asn Lys Asn Tyr Leu
1               5                   10                  15

Ala

<210> SEQ ID NO 99
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Cys Ser Arg Ser Thr Ser
            130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
450

<210> SEQ ID NO 100
<211> LENGTH: 215

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
            195                 200                 205

Val Ala Pro Thr Glu Cys Ser
    210                 215
```

ANTI-GPRC5D ANTIBODIES, BISPECIFIC ANTIGEN BINDING MOLECULES THAT BIND GPRC5D AND CD3, AND USES THEREOF

CROSS REFERENCE TO RELATED APPLICATIONS

This application is a divisional of U.S. patent application Ser. No. 15/655,086, filed Jul. 20, 2017, which is a U.S. Non-Provisional Patent Application and claims the benefit of U.S. Provisional Patent Application Ser. No. 62/364,811, filed Jul. 20, 2016, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 28, 2017, is named PRD3422USNP_SL.txt and is 57,673 bytes in size.

TECHNICAL FIELD

The disclosure provided herein relates to monoclonal antibodies that specifically bind G protein-coupled receptor class C group 5 member D (GPRC5D), multispecific antibodies specifically bind GPRC5D and cluster determinant 3 (CD3), and methods of producing and using the described antibodies.

BACKGROUND

Multiple myeloma (MM) is the second most common hematological malignancy and constitutes 2% of all cancer deaths. MM is a heterogenous disease and caused by mostly by chromosome translocations inter alia t(11; 14),t(4; 14),t(8;14),del(13),del(17) (Drach et al., (1998) Blood 92(3): 802-809; Gertz et al., (2005) Blood 106(8):2837-2840; Facon et al., (2001) Blood 97(6): 1566-1571). MM-affected patients may experience a variety of disease-related symptoms due to, bone marrow infiltration, bone destruction, renal failure, immunodeficiency, and the psychosocial burden of a cancer diagnosis. As of 2006, the 5-year relative survival rate for MM was approximately 34% highlighting that MM is a difficult-to-treat disease where there are currently no curative options.

G-protein coupled receptor, class C, group 5, member D (GPRC5D) is an orphan, atypical, class C GPCR first identified in 2001 (Branner-Osborne et al. Biochim Biophys Acta. 1518(3):237-248, 2001). GPRC5D and other group 5 GPCRs have unusually short amino-terminal domains for class C receptors, and are therefore, predicted to be conformationally similar to class A receptors. In this regard they are unique, with sequence homology to class C GPCRs and predicted structural topology comparable to class A receptors. Functional consequence of GPRC5D activation has not been described and the ligand remains unknown. The gene has three exons and is located on chromosome 12p13.3 in humans. GPRC5D receptor is highly conserved among various species and shares 92% identity with cynomolgus monkey GPRC5D.

GPRC5D mRNA is predominantly expressed in all malignant plasma cells from MM patients (Atamaniuk JA et al. Eur J Clin Invest 42(9) 953-960; 2012; Frigyesi-blood and Cohen, et al. Hematology 18(6): 348-35; 2013). GPRC5D expression is variable among the patients and correlate well with plasma cell burden and genetic aberrations such as Rb-1 deletion (Atamaniuk JA et al. Eur J Clin Invest 42(9) 953-960; 2012).

This exclusive expression of GPRC5D on the plasma-cell lineage designates it as an ideal target for antimyeloma antibodies.

SUMMARY

Provided herein are antibodies that specifically bind to GPRC5D and antigen-binding fragments thereof. Also described are related polynucleotides capable of encoding the provided GPRC5D-specific antibodies and antigen-binding fragments, cells expressing the provided antibodies and antigen-binding fragments, as well as associated vectors and detectably labeled antibodies and antigen-binding fragments. In addition, methods of using the provided antibodies and antigen-binding fragments are described. For example, the GPRC5D-specific antibodies and antigen-binding fragments may be used to diagnose or monitor GPRC5D-expressing cancer progression, regression, or stability; to determine whether or not a patient should be treated for cancer; or to determine whether or not a subject is afflicted with GPRC5D-expressing cancer and thus may be amenable to treatment with a GPRC5D-specific anti-cancer therapeutic, such as the multispecific antibodies against GPRC5D and CD3 described herein.

Further provided herein are multispecific antibodies that immunospecifically bind to GPRC5D and CD3 and multispecific antigen-binding fragments thereof. Also described are related polynucleotides capable of encoding the provided GPRC5D x CD3-multispecific antibodies, cells expressing the provided antibodies, as well as associated vectors and detectably labeled multispecific antibodies. In addition, methods of using the provided multispecific antibodies are described. For example, the GPRC5D x CD3-multispecific antibodies may be used to diagnose or monitor GPRC5D-expressing cancer progression, regression, or stability; to determine whether or not a patient should be treated for cancer; or to determine whether or not a subject is afflicted with GPRC5D-expressing cancer and thus may be amenable to treatment with a GPRC5D-specific anti-cancer therapeutic, such as the GPRC5D x CD3-multispecific antibodies described herein.

GPRC5D-Specific Antibodies

Described herein are isolated antibodies and antigen-binding fragments specific for GPRC5D. In some embodiments, the GPRC5D-specific antibodies and antigen-binding fragments bind human GPRC5D. In some embodiments, the GPRC5D-specific antibodies and antigen-binding fragments bind human GPRC5D and cynomolgus monkey GPRC5D. In some embodiments, the GPRC5D-specific antibodies and antigen-binding fragments bind to one or more residues of a polypeptide having the amino acid sequence of SEQ ID NO. 22. This GPRC5D-specific antibody or antigen-binding fragment may induce ADCC in vitro with an $EC_{50}$ of 28 nM or less.

Table 1 provides a summary of examples of some GPRC5D-specific antibodies described herein:

TABLE 1

CDR sequences of mAbs generated against human GPRC5D

| ID | HC-CDR1 | HC-CDR2 | HC-CDR3 | LC-CDR1 | LC-CDR2 | LC-CDR3 |
|---|---|---|---|---|---|---|
| GC5B81 | SYAIS (SEQ ID NO 1) | GIIPIFGTANYAQKFQG (SEQ ID NO 5) | ESRWRGYKLD (SEQ ID NO 9) | RASQSISSYLN (SEQ ID NO 13) | AASSLQS (SEQ ID NO 16) | QQSYSTPLT (SEQ ID NO 19) |
| GC5B465 GC5B597 | NYWMS (SEQ ID NO 2) | GISYSGGSKYYASSVKG (SEQ ID NO 6) | AAFDFGRRAVRLD (SEQ ID NO 10) | RASQSISSYLN (SEQ ID NO 13) | AASSLQS (SEQ ID NO 16) | QQSYSTPLT (SEQ ID NO 19) |
| GC5B483 GC5B599 | SYFIG (SEQ ID NO 3) | IIYPGKSDTRYSPSFQG (SEQ ID NO 7) | VYSFGGRHKALFDY (SEQ ID NO 11) | RASQSVSSYLA (SEQ ID NO 14) | DASNRAT (SEQ ID NO 17) | QQRSNWPLT (SEQ ID NO 20) |
| GC5B596 | GYTMN (SEQ ID NO 4) | LINPYNSDTNYAQKLQG (SEQ ID NO 8) | VALRVALDY (SEQ ID NO 12) | KASQNVATHVG (SEQ ID NO 15) | SASYRYS (SEQ ID NO 18) | QQYNRYPYT (SEQ ID NO 21) |
| GC5B382 | DYGMH (SEQ ID NO 61) | AIKYSGGSTYYADSVKG (SEQ ID NO 67) | RAESGPGLDY (SEQ ID NO 72) | KSSQSVLYSSNNKNYLA (SEQ ID NO 98) | WASTRES (SEQ ID NO 78) | QQYYSTPLT (SEQ ID NO 80) |
| GC5B379 | NYWMS (SEQ ID NO 2) | GISYSGGSKYYADSVKG (SEQ ID NO 28) | AAWDFGRRAVRLDY (SEQ ID NO 30) | RASQSISSYLN (SEQ ID NO 13) | AASSLQS (SEQ ID NO 16) | QQSYSTPLT (SEQ ID NO 19) |
| GC5B373 | SYWIG (SEQ ID NO 27) | IIYPGDSDTRYSPSFQG (SEQ ID NO 29) | IGFYGRSFRIFDY (SEQ ID NO 73) | RASQSVSSYLA (SEQ ID NO 14) | DASNRAT (SEQ ID NO 17) | QQRSNWPLT (SEQ ID NO 20) |
| GC5B376 | SYWIG (SEQ ID NO 27) | IIYPGDSDTRYSPSFQG (SEQ ID NO 29) | VYSFGGRHKALFDY (SEQ ID NO 11) | RASQSVSSYLA (SEQ ID NO 14) | DASNRAT (SEQ ID NO 17) | QQRSNWPLT (SEQ ID NO 20) |
| GC5B385 | GYAMS (SEQ ID NO 62) | AISGSGGSTYYADSVKG (SEQ ID NO 68) | VDRSFGRSRYTLDY (SEQ ID NO 74) | RASQSVSSYLA (SEQ ID NO 14) | DASNRAT (SEQ ID NO 17) | QQRSNWPLT (SEQ ID NO 20) |
| GC5B370 GC5B598 | SYGIS (SEQ ID NO 63) | GIIPIFGNINYAQKFQG (SEQ ID NO 69) | VSRRFKRFAYYFDY (SEQ ID NO 75) | KSSQSVLYSSNNKNYLA (SEQ ID NO 98) | WASTRES (SEQ ID NO 78) | QQYYSTPLT (SEQ ID NO 80) |
| GC5B602 | GYSFTGYTMN (SEQ ID NO 64) | LINPYNGDTN (SEQ ID NO 70) | VALRVALDY (SEQ ID NO 12) | KASQNVATHVG (SEQ ID NO 15) | SASYRYS (SEQ ID NO 18) | QQYNRYPYT (SEQ ID NO 21) |
| GC5B603 | SYAMS (SEQ ID NO 65) | AISGSGGSTYYADSVKG (SEQ ID NO 68) | SNFLPVVFDY (SEQ ID NO 76) | RASQSVRKSLA (SEQ ID NO 95) | TASNRAT (SEQ ID NO 79) | QQYFRAPIT (SEQ ID NO 81) |
| GC5B601 | GFSLTSYNVH (SEQ ID NO 66) | VIWAGGSTNYNSALMS (SEQ ID NO 71) | DGIRLRFAY (SEQ ID NO 77) | KASQNVATHVG (SEQ ID NO 15) | SASYRYS (SEQ ID NO 18) | QQYNRYPYT (SEQ ID NO 21) |

In some embodiments are provided a GPRC5D-specific antibody, or an antigen-binding fragment thereof, comprising a heavy chain comprising a CDR1, a CDR2, and a CDR3 of any one of the antibodies described in Table 1. In some embodiments are provided a GPRC5D-specific antibody, or an antigen-binding fragment thereof, comprising a heavy chain comprising a CDR1, a CDR2, and a CDR3 of any one of the antibodies described in Table 1 and a light chain comprising a CDR1, a CDR2, and a CDR3 of any one of the antibodies described in Table 1. In some embodiments described herein, the GPRC5D-specific antibody or antigen-binding fragment thereof competes for binding to GPRC5D with an antibody or antigen-binding comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcgRs) on the surface of immune effector cells such as natural killers and macrophages, leading to the phagocytosis or lysis of the targeted cells. In CDC, the antibodies kill the targeted cells by triggering the complement cascade at the cell surface. The antibodies described herein include antibodies with the described features of the variable domains in combination with any of the IgG isotypes, including modified versions in which the Fc sequence has been modified to effect different effector functions.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcgRs or the complement factors. The binding of IgG to the activating (FcgRI, FcgRIIa, FcgRIIIa and FcgRIIIb) and inhibitory (FcgRIIb) FcgRs or the first component of complement (C1q) depends on residues located in the hinge region and the CH2 domain. Mutations have been introduced in IgG1, IgG2 and IgG4 to reduce or silence Fc functionalities. The antibodies described herein may include these modifications.

In one embodiment, the antibody comprises an Fc region with one or more of the following properties: (a) reduced effector function when compared to the parent Fc; (b) reduced affinity to Fcg RI, Fcg RIIa, Fcg RIIb, Fcg RIIIb and/or Fcg RIIIa, (c) reduced affinity to FcgRI (d) reduced affinity to FcgRIIa (e) reduced affinity to FcgRIIb, (f) reduced affinity to Fcg RIIIb or (g) reduced affinity to FcgRIIIa.

In some embodiments, the antibodies or antigen-binding fragments are IgG, or derivatives thereof, e.g., IgG1, IgG2, IgG3, and IgG4 isotypes. In some embodiments wherein the antibody has an IgG1 isotype, the antibody contains L234A, L235A, and/or K409R substitution(s) in its Fc region. In some embodiments wherein the antibody has an IgG4 isotype, the antibody contains S228P, L234A, and L235A substitutions in its Fc region. The antibodies described herein may include these modifications.

In addition to the described GPRC5D-specific antibodies and antigen-binding fragments, also provided are polynucleotide sequences capable of encoding the described antibodies and antigen-binding fragments. Vectors comprising the described polynucleotides are also provided, as are cells expressing the GPRC5D-specific antibodies or antigen-binding fragments provided herein. Also described are cells capable of expressing the disclosed vectors. These cells may be mammalian cells (such as 293F cells, CHO cells), insect cells (such as Sf7 cells), yeast cells, plant cells, or bacteria cells (such as *E. coli*). The described antibodies may also be produced by hybridoma cells.

Methods of using GPRC5D-Specific Antibodies

Methods of using the described GPRC5D-specific antibodies or antigen-binding fragments are also disclosed. Particular antibodies for use in the methods discussed in this section include those with the set of CDRs described for antibodies in Table 1. For example, these antibodies or antigen-binding fragments may be useful in treating cancer, by interfering with GPRC5D-receptor interactions or where the antibody is conjugated to a toxin, so targeting the toxin to the GPRC5D-expressing cancer. Further, these antibodies or antigen-binding fragments may be useful for detecting the presence of GPRC5D in a biological sample, such as blood or serum; for quantifying the amount of GPRC5D in a biological sample, such as blood or serum; for diagnosing GPRC5D-expressing cancer; determining a method of treating a subject afflicted with cancer; or monitoring the progression of GPRC5D-expressing cancer in a subject. In some embodiments, GPRC5D-expressing cancer may be a lymphoma, such as multiple myeloma (MM). The described methods may be carried out before the subject receives treatment for GPRC5D-expressing cancer, such as treatment with a multispecific antibody against GPRC5D and CD3. Furthermore, the described methods may be carried out after the subject receives treatment for GPRC5D-expressing cancer, such as treatment with a multispecific antibody against GPRC5D and CD3 described herein.

The described methods of detecting GPRC5D in a biological sample include exposing the biological sample to one or more of the GPRC5D-specific antibodies or antigen-binding fragments described herein.

The described methods of diagnosing GPRC5D-expressing cancer in a subject also involve exposing the biological sample to one or more of the GPRC5D-specific antibodies or antigen-binding fragments described herein; however, the methods also include quantifying the amount of GPRC5D present in the sample; comparing the amount of GPRC5D present in the sample to a known standard or reference sample; and determining whether the subject's GPRC5D levels fall within the levels of GPRC5D associated with cancer.

Also described herein are methods of monitoring GPRC5D-expressing cancer in a subject. The described methods include exposing the biological sample to one or more of the GPRC5D-specific antibodies or antigen-binding fragments described herein; quantifying the amount of GPRC5D present in the sample that is bound by the antibody, or antigen-binding fragment thereof; comparing the amount of GPRC5D present in the sample to either a known standard or reference sample or the amount of GPRC5D in a similar sample previously obtained from the subject; and determining whether the subject's GPRC5D levels are indicative of cancer progression, regression or stable disease based on the difference in the amount of GPRC5D in the compared samples.

The samples obtained, or derived from, subjects are biological samples such as urine, blood, serum, plasma, saliva, ascites, circulating cells, circulating tumor cells, cells that are not tissue associated, tissues, surgically resected tumor tissue, biopsies, fine needle aspiration samples, or histological preparations.

The described GPRC5D-specific antibodies or antigen-binding fragments may be labeled for use with the described methods, or other methods known to those skilled in the art. For example, the antibodies described herein, or antigen-binding fragments thereof, may be labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art.

GPRC5D-Specific Antibody Kits

Described herein are kits including the disclosed GPRC5D-specific antibodies or antigen-binding fragments thereof. The described kits may be used to carry out the methods of using the GPRC5D-specific antibodies or antigen-binding fragments provided herein, or other methods known to those skilled in the art. In some embodiments the described kits may include the antibodies or antigen-binding fragments described herein and reagents for use in detecting the presence of GPRC5D in a biological sample. Accordingly, the described kits may include one or more of the antibodies, or an antigen-binding fragment(s) thereof, described herein and a vessel for containing the antibody or fragment when not in use, instructions for use of the antibody or fragment, the antibody or fragment affixed to a solid support, and/or detectably labeled forms of the antibody or fragment, as described herein.

GPRC5D x CD3-Multispecific Antibodies

The redirection of T-lymphocytes to MM cells expressing GPRC5D via the TCR/CD3 complex represents an attractive alternative approach. The TCR/CD3 complex of T-lymphocytes consists of either a TCR alpha ($\alpha$)/beta (($\beta$) or TCR gamma ($\gamma$)/delta ($\delta$) heterodimer coexpressed at the cell surface with the invariant subunits of CD3 labeled gamma ($\gamma$), delta ($\delta$), epsilon ($\epsilon$), zeta ($\zeta$), and eta ($\eta$). Human CD3$\epsilon$ is described under UniProt P07766 (CD3E_HUMAN). An anti CD3$\epsilon$ antibody described in the state of the art is SP34 (Yang S J, The Journal of Immunology (1986) 137; 1097-1100). SP34 reacts with both primate and human CD3. SP34 is available from Pharmingen. A further anti CD3 antibody described in the state of the art is UCHT-1 (see WO2000041474). A further anti CD3 antibody described in the state of the art is BC-3 (Fred Hutchinson Cancer Research Institute; used in Phase I/II trials of GvHD, Anasetti et al., Transplantation 54:844 (1992)). SP34 differs from UCHT-1 and BC-3 in that SP-34 recognizes an epitope present on solely the c chain of CD3 (see Salmeron et al., (1991) J. Immunol. 147:3047) whereas UCHT-1 and BC-3 recognize an epitope contributed by both the and $\gamma$ chains. The sequence of an antibody with the same sequence as of antibody SP34 is mentioned in WO2008119565, WO2008119566, WO2008119567, WO2010037836, WO2010037837 and WO2010037838. A sequence which is 96% identical to VH of antibody SP34 is mentioned in U.S. Pat. No. 8,236,308 (WO2007042261).

Described herein are isolated multispecific antibodies that bind GPRC5D and CD3 ("GPRC5D x CD3 multispecific antibodies") and multispecific antigen-binding fragments thereof. In some embodiments an isolated antibody, or an antigen-binding fragment thereof, that binds immunospecifically to GPRC5D is provided.

In some embodiments, the GPRC5D-specific arm of the multispecific antibody binds human GPRC5D and cynomolgus monkey GPRC5D. In some embodiments, the GPRC5D-specific arm of the GPRC5D x CD3-multispecific antibodies or antigen-binding fragments binds the extracellular domain of human GPRC5D. In preferred embodiments, the GPRC5D x CD3 multispecific antibody or antigen-binding fragment is a bispecific antibody or antigen-binding fragment. In some embodiments, an isolated GPRC5D x CD3 bispecific antibody comprising: a) a first heavy chain (HC1); b) a second heavy chain (HC2); c) a first light chain (LC1); and d) a second light chain (LC2), wherein the HC1 and the LC1 pair to form a first antigen-binding site that immunospecifically binds GPRC5D, and the HC2 and the LC2 pair to form a second antigen-binding site that immunospecifically binds CD3, or a GPRC5D x CD3-bispecific binding fragment thereof is provided. In another embodiment, an isolated cell expressing the antibody or bispecific binding fragment is provided. In some embodiments, the GPRC5D-binding arm (or "GPRC5D-specific arm") of the GPRC5D x CD3 multispecific antibody is derived from a GPRC5D antibody described herein (for example, from an antibody having the CDR sequences listed in Table 1).

In some embodiments, the GPRC5D-specific arm of the GPRC5D x CD3-multispecific antibodies or antigen-binding fragments are IgG, or derivatives thereof. In some embodiments, the CD3-binding arm (or "CD3-specific arm") of the GPRC5D x CD3 multispecific antibody is derived from the mouse monoclonal antibody SP34, a mouse IgG3/lambda isotype. (K. R. Abhinandan and A. C. Martin, 2008. Mol. Immunol. 45, 3832-3839). In some embodiments, the CD3-binding arm of the GPRC5D x CD3 multispecific antibody comprises one VH domain and one VL domain selected from Table 2.

effector functions, such as antibody-dependent cellular cytotoxicity (ADCC) and complement-dependent cytotoxicity (CDC). In ADCC, the Fc region of an antibody binds to Fc receptors (FcgRs) on the surface of immune effector cells such as natural killers and macrophages, leading to the phagocytosis or lysis of the targeted cells. In CDC, the antibodies kill the targeted cells by triggering the complement cascade at the cell surface.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcgRs or the complement factors. The binding of IgG to the activating (FcgRI, FcgRIIa, FcgRIIIa and FcgRIIIb) and inhibitory (FcgRIIb) FcgRs or the first component of complement (C1q) depends on residues located in the hinge region and the CH2 domain. Mutations have been introduced in IgG1, IgG2 and IgG4 to reduce or silence Fc functionalities.

In one embodiment, the antibody comprises an Fc region with one or more of the following properties: (a) reduced effector function when compared to the parent Fc; (b) reduced affinity to Fcg RI, Fcg RIIa, Fcg RIIb, Fcg RIIIb and/or Fcg RIIIa, (c) reduced affinity to FcgRI (d) reduced affinity to FcgRIIa (e) reduced affinity to FcgRIIb, (f) reduced affinity to Fcg RIIIb or (g) reduced affinity to FcgRIIIa.

In some embodiments, the CD3-specific antibody or antigen-binding fragment from which the CD3-specific arm of the multispecific antibody is derived is IgG, or a derivative thereof. In some embodiments, the CD3-specific antibody or antigen-binding fragment from which the CD3-specific arm of the multispecific antibody is derived is IgG1, or a derivative thereof. In some embodiments, for example, the Fc region of the CD3-specific IgG1 antibody from which the CD3-binding arm is derived comprises L234A, L235A, and F405L substitutions in its Fc region. In some embodiments, the CD3-specific antibody or antigen-binding fragment from which the CD3-specific arm of the multispecific antibody is derived is IgG4, or a derivative thereof. In some

TABLE 2

Heavy chains and light chains of the CD3-specific antibody and antigen-binding fragment.

| VH | VL |
|---|---|
| CD3B219 (SEQ ID NO: 99):<br>EVQLVESGGGLVQPGGSLRLSCAASGFTFN<br>TYAMNWVRQAPGKGLEWVARIRSKYNNYAT<br>YYAASVKGRFTISRDDSKNSLYLQMNSLKTE<br>DTAVYYCARHGNFGNSYVSWFAYWGQGTL<br>VTVSSASTKGPSVFPLAPCSRSTSESTAALG<br>CLVKDYFPEPVTVSWNSGALTSGVHTFPAVL<br>QSSGLYSLSSVVTVPSSSLGTKTYTCNVDHK<br>PSNTKVDKRVESKYGPPCPPCPAPEAAGGP<br>SVFLFPPKPKDTLMISRTPEVTCVVVDVSQED<br>PEVQFNWYVDGVEVHNAKTKPREEQFNSTY<br>RVVSVLTVLHQDWLNGKEYKCKVSNKGLPS<br>SIEKTISKAKGQPREPQVYTLPPSQEEMTKN<br>QVSLTCLVKGFYPSDIAVEWESNGQPENNYK<br>TTPPVLDSDGSFLLYSKLTVDKSRWQEGNVF<br>SCSVMHEALHNHYTQKSLSLSLGK | CD3B219 (SEQ ID NO: 100):<br>QTVVTQEPSLTVSPGGTVTLTCRSSTGAVTTSNYA<br>NWVQQKPGQAPRGLIGGTNKRAPGTPARFSGSLL<br>GGKAALTLSGVQPEDEAEYYCALWYSNLWVFGG<br>GTKLTVLGQPKAAPSVTLFPPSSEELQANKATLVC<br>LISDFYPGAVTVAWKADSSPVKAGVETTTPSKQSN<br>NKYAASSYLSLTPEQWKSHRSYSCQVTHEGSTVE<br>KTVAPTECS |

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates embodiments, for example, the Fc region of the CD3-specific IgG4 antibody from which the CD3-binding arm is derived comprises S228P, L234A, L235A, F405L, and R409K substitutions in its Fc region. In some embodiments, the CD3-specific antibody or antigen-binding fragment from which the CD3-specific arm of the multispecific antibody is derived binds CD3ε on primary human T cells and/or primary cynomolgus T cells. In some embodiments, the CD3-specific antibody or antigen-binding fragment from which the CD3-specific arm of the multispecific antibody is derived activates primary human CD4+ T cells and/or primary cynomolgus CD4+ T cells.

In addition to the described GPRC5D x CD3-multispecific antibodies, also provided are polynucleotide sequences capable of encoding the described GPRC5D x CD3-multispecific antibodies. In some embodiments, an isolated synthetic polynucleotide encoding the HC1, the HC2, the LC1 or the LC2 of the GPRC5D x CD3 bispecific antibody or bispecific binding fragment is provided. Vectors comprising the described polynucleotides are also provided, as are cells expressing the GPRC5D x CD3-multispecific antibodies provided herein. Also described are cells capable of expressing the disclosed vectors. These cells may be mammalian cells (such as 293F cells, CHO cells), insect cells (such as Sf7 cells), yeast cells, plant cells, or bacteria cells (such as E. coli). The described antibodies may also be produced by hybridoma cells. In some embodiments, methods for generating the GPRC5D x CD3 bispecific antibody or bispecific binding fragment by culturing cells is provided.

Further provided herein are pharmaceutical compositions comprising the GPRC5D x CD3 multispecific antibodies or antigen-binding fragments and a pharmaceutically acceptable carrier.

Methods of using GPRC5D x CD3-Multispecific Antibodies

Methods of using the described GPRC5D x CD3-multispecific antibodies and multispecific antigen-binding fragments thereof are also disclosed. For example, the GPRC5D x CD3-multispecific antibodies and multispecific antigen-binding fragments thereof may be useful in the treatment of a GPRC5D-expressing cancer in a subject in need thereof. In some embodiments, the GPRC5D-expressing cancer is a lymphoma, such as multiple myeloma.

The described methods of treating GPRC5D-expressing cancer in a subject in need thereof include administering to the subject a therapeutically effective amount of a described GPRC5D x CD3-multispecific antibody or multispecific antigen-binding fragment thereof. In some embodiments, the subject is a mammal, preferably a human. In preferred embodiments are provided methods for treating a subject having cancer by administering a therapeutically effective amount of the GPRC5D x CD3 bispecific antibody or bispecific antigen-binding fragment to a patient in need thereof for a time sufficient to treat the cancer.

Further provided herein are methods for inhibiting growth or proliferation of cancer cells by administering a therapeutically effective amount of the GPRC5D x CD3 bispecific antibody or bispecific binding fragment to inhibit the growth or proliferation of cancer cells.

Also provided herein are methods of redirecting a T cell to a GPRC5D-expressing cancer cell by administering a therapeutically effective amount of the GPRC5D x CD3 bispecific antibody or bispecific binding fragment to redirect a T cell to a cancer.

GPRC5D x CD3-Specific Antibody Kits

Described herein are kits including the disclosed GPRC5D x CD3-multispecific antibodies. The described kits may be used to carry out the methods of using the GPRC5D x CD3-multispecific antibodies provided herein, or other methods known to those skilled in the art. In some embodiments the described kits may include the antibodies described herein and reagents for use in treating a GPRC5D-expressing cancer. Accordingly, the described kits may include one or more of the multispecific antibodies, or a multispecific antigen-binding fragment(s) thereof, described herein and a vessel for containing the antibody or fragment when not in use, and/or instructions for use of the antibody or fragment, the antibody or fragment affixed to a solid support, and/or detectably labeled forms of the antibody or fragment, as described herein.

BRIEF DESCRIPTION OF THE DRAWINGS

FIG. 11A-11E. GPRC5D x CD3 bispecific antibody binding to GPRC5D positive (H929, MM1R, LP1, OPM2) and negative cell lines (NALM6).

FIG. 14B shows the binding pattern of the lead molecules on GPRC5D+ multiple myeloma cell lines. Shaded, dotted line indicates isotype control and the solid line indicate lead molecule binding.

DETAILED DESCRIPTION OF ILLUSTRATIVE EMBODIMENTS

Definitions

Figure 1:
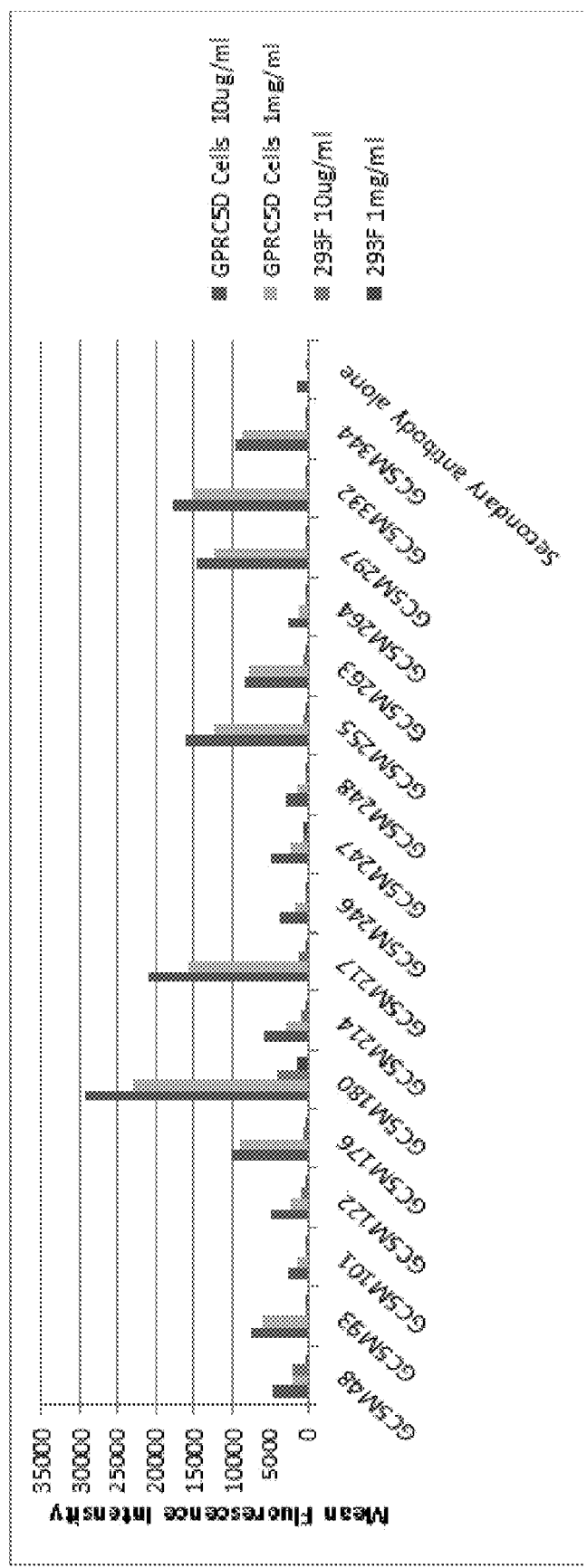
FIG. 1: Concentration dependent binding profile of selected anti-GPRC5D mAbs against human GPRC5D and non-transfected HEK 293 cells. Three mAbs, GC5B36, GC5B168, and GC5B205 were also observed to bind to the non-transfected (GPRC5D null) HEK293 cells.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" antibody or antigen-binding fragment, as used herein, is intended to refer to an antibody or antigen-binding fragment which is substantially free of other antibodies or antigen-binding fragments having different antigenic specificities (for instance, an isolated antibody that specifically binds to GPRC5D is substantially free of antibodies that specifically bind antigens other than GPRC5D). An isolated antibody that specifically binds to an epitope, isoform or variant of GPRC5D may, however, have cross-reactivity to other related antigens, for instance from other species (such as GPRC5D species homologs).

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include GPRC5D specific antibodies, or antigen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein. A "vector" is a replicon, such as plasmid, phage, cosmid, or virus in which another nucleic acid segment may be operably inserted so as to bring about the replication or expression of the segment.

A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

An "effective amount" or "therapeutically effective amount" refers to an amount effective, at dosages and for periods of time necessary, to achieve a desired therapeutic result. A therapeutically effective amount of a GPRC5D x CD3 antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

"Antibody" refers to all isotypes of immunoglobulins (IgG, IgA, IgE, IgM, IgD, and IgY) including various monomeric, polymeric and chimeric forms, unless otherwise specified.

Specifically encompassed by the term "antibody" are polyclonal antibodies, monoclonal antibodies (mAbs), and antibody-like polypeptides, such as chimeric antibodies and humanized antibodies.

"Antigen-binding fragments" are any proteinaceous structure that may exhibit binding affinity for a particular antigen. Antigen-binding fragments include those provided by any known technique, such as enzymatic cleavage, peptide synthesis, and recombinant techniques. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, a monovalent fragment consisting of the VL, VH, CL and CH1 domains, or a monovalent antibody as described in WO2007059782, bivalent fragments comprising two Fab fragments linked by a disulfide bridge at the hinge region, a Fd fragment consisting essentially of the $V_H$ and C.sub.H1 domains; a Fv fragment consisting essentially of the VL and VH domains of a single arm of an antibody, a dAb fragment (Ward et al., Nature 341, 544-546 (1989)), which consists essentially of a VH domain and also called domain antibodies (Holt et al; Trends Biotechnol. 2003 Nov.; 21(11):484-90); camelid or nanobodies (Revets et al; Expert Opin Biol Ther. 2005 Jan.; 5(1):111-24); an isolated complementarity determining region (CDR), and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase. The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat et al., *Sequences of Proteins of Immunological Interest,* 5th ed. NIH Publication No. 91-3242 (1991); Chothia et al., "Canonical Structures For the Hypervariable Regions of Immunoglobulins," *J. Mol. Biol.* 196:901 (1987); and MacCallum et al., "Antibody-Antigen Interactions: Contact Analysis and Binding Site Topography," J. Mol. Biol. 262:732 (1996)), each of which is hereby incorporated by reference in its entirety.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia et al., "Canonical Structures For the Hypervariable Regions of Immunoglobulins," *J. Mol. Biol.* 196: 901 (1987); Chothia et al., "Conformations of Immunoglobulin Hypervariable Regions," I 342:877 (1989); Martin and Thornton, "Structural Families in Loops of Homologous Proteins: Automatic Classification, Modelling and Application to Antibodies," *J. Mol. Biol.* 263:800 (1996), each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

"Specifically binds" or "binds specifically" or derivatives thereof when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1\times10^{-8}$ M, as measured by a surface plasmon resonance assay or a cell-binding assay. Phrases such as "[antigen]-specific" antibody (e.g., GPRC5D-specific antibody) are meant to convey that the recited antibody specifically binds the recited antigen.

Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

A "vector" is a replicon, such as plasmid, phage, cosmid, or virus in which another nucleic acid segment may be operably inserted so as to bring about the replication or expression of the segment.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome. The terms "expression" and "production" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture. The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include GPRC5D-specific antibodies, or antigen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

The term "redirect" or "redirecting" as used herein refers to the ability of the GPRC5D x CD3 antibody to traffic the activity of T cells effectively, from its inherent cognate specificity toward reactivity against GPRC5D-expressing cells.

The term "sample" as used herein refers to a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject.

A "known standard" may be a solution having a known amount or concentration of GPRC5D, where the solution may be a naturally occurring solution, such as a sample from a patient known to have early, moderate, late, progressive, or static cancer, or the solution may be a synthetic solution such as buffered water having a known amount of GPRC5D diluted therein. The known standards, described herein may include GPRC5D isolated from a subject, recombinant or purified GPRC5D protein, or a value of GPRC5D concentration associated with a disease condition.

As used herein, the terms "G-protein coupled receptor family C group 5 member D" and "GPRC5D" specifically include the human GPRC5D protein, for example as described in GenBank Accession No. BC069341, NCBI Reference Sequence: NP 061124.1 and UniProtKB/SwissProt Accession No. Q9NZD1 (see also Brauner-Osborne, H. et al. 2001, Biochim. Biophys. Acta 1518, 237-248).

The term "CD3" refers to the human CD3 protein multi-subunit complex. The CD3 protein multi-subunit complex is composed to 6 distinctive polypeptide chains. These include a CD3γ chain (SwissProt P09693), a CD3δ chain (SwissProt P04234), two CD3ε chains (SwissProt P07766), and one CD3 ζ chain homodimer (SwissProt 20963), and which is associated with the T cell receptor α and β chain. The term "CD3" includes any CD3 variant, isoform and species homolog which is naturally expressed by cells (including T cells) or can be expressed on cells transfected with genes or cDNA encoding those polypeptides, unless noted.

A "GPRC5D x CD3 antibody" is a multispecific antibody, optionally a bispecific antibody, which comprises two different antigen-binding regions, one of which binds specifically to the antigen GPRC5D and one of which binds specifically to CD3. A multispecific antibody can be a bispecific antibody, diabody, or similar molecule (see for instance *PNAS USA* 90(14), 6444-8 (1993) for a description of diabodies). The bispecific antibodies, diabodies, and the like, provided herein may bind any suitable target in addition to a portion of GPRC5D. The term "bispecific antibody" is to be understood as an antibody having two different antigen-binding regions defined by different antibody sequences. This can be understood as different target binding but includes as well binding to different epitopes in one target.

A "reference sample" is a sample that may be compared against another sample, such as a test sample, to allow for characterization of the compared sample. The reference sample will have some characterized property that serves as the basis for comparison with the test sample. For instance, a reference sample may be used as a benchmark for GPRC5D levels that are indicative of a subject having cancer. The reference sample does not necessarily have to be analyzed in parallel with the test sample, thus in some instances the reference sample may be a numerical value or range previously determined to characterize a given condition, such as GPRC5D levels that are indicative of cancer in a subject. The term also includes samples used for comparative purposes that are known to be associated with a physiologic state or disease condition, such as GPRC5D-expressing cancer, but that have an unknown amount of GPRC5D.

The term "progression," as used in the context of progression of GPRC5D-expressing cancer, includes the change of a cancer from a less severe to a more severe state. This may include an increase in the number or severity of tumors, the degree of metastasis, the speed with which the cancer is growing or spreading, and the like. For example, "the progression of colon cancer" includes the progression of such a cancer from a less severe to a more severe state, such as the progression from stage I to stage II, from stage II to stage III, etc.

The term "regression," as used in the context of regression of GPRC5D-expressing cancer, includes the change of a cancer from a more severe to a less severe state. This could include a decrease in the number or severity of tumors, the degree of metastasis, the speed with which the cancer is growing or spreading, and the like. For example, "the regression of colon cancer" includes the regression of such a cancer from a more severe to a less severe state, such as the progression from stage III to stage II, from stage II to stage I, etc.

The term "stable" as used in the context of stable GPRC5D-expressing cancer, is intended to describe a disease condition that is not, or has not, changed significantly enough over a clinically relevant period of time to be considered a progressing cancer or a regressing cancer.

The embodiments described herein are not limited to particular methods, reagents, compounds, compositions or biological systems, which can, of course, vary.

GPRC5D-Specific Antibodies and Antigen-Binding Fragments

Described herein are isolated monoclonal antibodies or antigen-binding fragments that specifically bind GPRC5D. The general structure of an antibody molecule comprises an antigen binding domain, which includes heavy and light chains, and the Fc domain, which serves a variety of functions, including complement fixation and binding antibody receptors.

The described GPRC5D-specific antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The GPRC5D-specific antibodies and antigen-binding fragments may be derived from any species by recombinant means. For example, the antibodies or antigen-binding fragments may be mouse, rat, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

The antibodies or antigen-binding fragments described herein can occur in a variety of forms, but will include one or more of the antibody CDRs shown in Table 1.

Described herein are isolated antibodies and antigen-binding fragments that immunospecifically bind to GPRC5D. In some embodiments, the GPRC5D-specific antibodies or antigen-binding fragments are human IgG, or derivatives thereof. While the GPRC5D-specific antibodies or antigen-binding fragments exemplified herein are human, the antibodies or antigen-binding fragments exemplified may be chimerized.

In some embodiments are provided a GPRC5D-specific antibody, or an antigen-binding fragment thereof, comprising a heavy chain comprising a CDR1, a CDR2, and a CDR3 of any one of the antibodies described in Table 1. In some embodiments are provided a GPRC5D-specific antibody, or an antigen-binding fragment thereof, comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

In some embodiments, the GPRC5D-specific antibodies and antigen-binding fragments comprise a heavy chain CDR1 comprising SEQ ID NO: 1, a heavy chain CDR2 comprising SEQ ID NO: 5, and a heavy chain CDR3 comprising SEQ ID NO: 9. In some embodiments, the GPRC5D-specific antibodies and antigen-binding fragments comprise a heavy chain CDR1 comprising SEQ ID NO: 1, a heavy chain CDR2 comprising SEQ ID NO: 5, a heavy chain CDR3 comprising SEQ ID NO: 9, a light chain CDR1 comprising SEQ ID NO: 13, a light chain CDR2 comprising SEQ ID NO: 16, and a light chain CDR3 comprising SEQ ID NO: 19. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 52. In some embodiments, the GPRC5D-specific antibodies and antigen-binding fragments comprise a heavy chain variable domain substantially the same as, or identical to, SEQ ID NO: 52 and a light chain variable domain substantially the same as, or identical to, SEQ ID NO: 56. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 2, a heavy chain CDR2 comprising SEQ ID NO: 6, and a heavy chain CDR3 comprising SEQ ID NO: 10. In some embodiments, the GPRC5D-specific antibodies and antigen-binding fragments comprise a heavy chain CDR1 comprising SEQ ID NO: 2, a heavy chain CDR2 comprising SEQ ID NO: 6, a heavy chain CDR3 comprising SEQ ID NO: 10, a light chain CDR1 comprising SEQ ID NO: 13, a light chain CDR2 comprising SEQ ID NO: 16, and a light chain CDR3 comprising SEQ ID NO: 19. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 53. In some embodiments, the GPRC5D-specific antibodies and antigen-binding fragments comprise a heavy chain variable domain substantially the same as, or identical to, SEQ ID NO: 53 and a light chain variable domain substantially the same as, or identical to, SEQ ID NO: 56. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 3, a heavy chain CDR2 comprising SEQ ID NO: 7, and a heavy chain CDR3 comprising SEQ ID NO: 11. In some embodiments, the GPRC5D-specific antibodies and antigen-binding fragments comprise a heavy chain CDR1 comprising SEQ ID NO: 3, a heavy chain CDR2 comprising SEQ ID NO: 7, a heavy chain CDR3 comprising SEQ ID NO: 11, a light chain CDR1 comprising SEQ ID NO: 14, a light chain CDR2 comprising SEQ ID NO: 17, and a light chain CDR3 comprising SEQ ID NO: 20. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 54. In some embodiments, the GPRC5D-specific antibodies and antigen-binding fragments comprise a heavy chain variable domain substantially the same as, or identical to, SEQ ID NO: 54 and a light chain variable domain substantially the same as, or identical to, SEQ ID NO: 57. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 4, a heavy chain CDR2 comprising SEQ ID NO: 8, and a heavy chain CDR3 comprising SEQ ID NO: 12. In some embodiments, the GPRC5D-specific antibodies and antigen-binding fragments comprise a heavy chain CDR1 comprising SEQ ID NO: 4, a heavy chain CDR2 comprising SEQ ID NO: 8, a heavy chain CDR3 comprising SEQ ID NO: 12, a light chain CDR1 comprising SEQ ID NO: 15, a light chain CDR2 comprising SEQ ID NO: 18, and a light chain CDR3 comprising SEQ ID NO: 21. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 55. In some embodiments, the GPRC5D-specific antibodies and antigen-binding fragments comprise a heavy chain variable domain substantially the same as, or identical to, SEQ ID NO: 55 and a light chain variable domain substantially the same as, or identical to, SEQ ID NO: 58. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 61, a heavy chain CDR2 comprising SEQ ID NO: 67, and a heavy chain CDR3 comprising SEQ ID NO: 72. In some embodiments, the GPRC5D-specific antibodies and antigen-binding fragments comprise a heavy chain CDR1 comprising SEQ ID NO: 61, a heavy chain CDR2 comprising SEQ ID NO: 67, a heavy chain CDR3 comprising SEQ ID NO: 72, a light chain CDR1 comprising SEQ ID NO: 13, a light chain CDR2 comprising SEQ ID NO: 78, and a light chain CDR3 comprising SEQ ID NO: 80. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 82. In some embodiments, the GPRC5D-specific antibodies and antigen-binding fragments comprise a heavy chain variable domain substantially the same as, or identical to, SEQ ID NO: 82 and a light chain variable domain substantially the same as, or identical to, SEQ ID NO: 92. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 2, a heavy chain CDR2 comprising SEQ ID NO: 28, and a heavy chain CDR3 comprising SEQ ID NO: 30. In some embodiments, the GPRC5D-specific antibodies and antigen-binding fragments comprise a heavy chain CDR1 comprising SEQ ID NO: 2, a heavy chain CDR2 comprising SEQ ID NO: 28, a heavy chain CDR3 comprising SEQ ID NO: 30, a light chain CDR1 comprising SEQ ID NO: 13, a light chain CDR2 comprising SEQ ID NO: 16, and a light chain CDR3 comprising SEQ ID NO: 19. This GPRC5D-specific antibody or antigen-binding fragment may comprise human framework sequences. In some embodiments, the GPRC5D- specific antibodies and antigen-binding fragments comprise a heavy chain variable domain substantially the same as, or identical to, SEQ ID NO: 83. In some embodiments, the GPRC5D-specific antibodies and antigen-binding fragments comprise a heavy chain variable domain substantially the same as, or identical to, SEQ ID NO: 83 and a light chain variable domain substantially the same as, or identical to, SEQ ID NO: 56. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 27, a heavy chain CDR2 comprising SEQ ID NO: 29, and a heavy chain CDR3 comprising SEQ ID NO: 73. In some embodiments, the GPRC5D-specific antibodies and antigen-binding fragments comprise a heavy chain CDR1 comprising SEQ ID NO: 27, a heavy chain CDR2 comprising SEQ ID NO: 29, a heavy chain CDR3 comprising SEQ ID NO: 73, a light chain CDR1 comprising SEQ ID NO: 14, a light chain CDR2 comprising SEQ ID NO: 17, and a light chain CDR3 comprising SEQ ID NO: 20.

This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 84. In some embodiments, the GPRC5D-specific antibodies and antigen-binding fragments comprise a heavy chain variable domain substantially the same as, or identical to, SEQ ID NO: 84 and a light chain variable domain substantially the same as, or identical to, SEQ ID NO: 57. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 27, a heavy chain CDR2 comprising SEQ ID NO: 29, and a heavy chain CDR3 comprising SEQ ID NO: 11. In some embodiments, the GPRC5D-specific antibodies and antigen-binding fragments comprise a heavy chain CDR1 comprising SEQ ID NO: 27, a heavy chain CDR2 comprising SEQ ID NO: 29 a heavy chain CDR3 comprising SEQ ID NO: 11, a light chain CDR1 comprising SEQ ID NO: 14, a light chain CDR2 comprising SEQ ID NO: 17, and a light chain CDR3 comprising SEQ ID NO: 20. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 85. In some embodiments, the GPRC5D-specific antibodies and antigen-binding fragments comprise a heavy chain variable domain substantially the same as, or identical to, SEQ ID NO: 85 and a light chain variable domain substantially the same as, or identical to, SEQ ID NO: 57. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 62, a heavy chain CDR2 comprising SEQ ID NO: 68, and a heavy chain CDR3 comprising SEQ ID NO: 74. In some embodiments, the GPRC5D-specific antibodies and antigen-binding fragments comprise a heavy chain CDR1 comprising SEQ ID NO: 62, a heavy chain CDR2 comprising SEQ ID NO: 68, a heavy chain CDR3 comprising SEQ ID NO: 74, a light chain CDR1 comprising SEQ ID NO: 14, a light chain CDR2 comprising SEQ ID NO: 17, and a light chain CDR3 comprising SEQ ID NO: 20. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 86. In some embodiments, the GPRC5D-specific antibodies and antigen-binding fragments comprise a heavy chain variable domain substantially the same as, or identical to, SEQ ID NO: 86 and a light chain variable domain substantially the same as, or identical to, SEQ ID NO: 57. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 63, a heavy chain CDR2 comprising SEQ ID NO: 69, and a heavy chain CDR3 comprising SEQ ID NO: 75. In some embodiments, the GPRC5D-specific antibodies and antigen-binding fragments comprise a heavy chain CDR1 comprising SEQ ID NO: 63, a heavy chain CDR2 comprising SEQ ID NO: 69, a heavy chain CDR3 comprising SEQ ID NO: 75, a light chain CDR1 comprising SEQ ID NO: 13, a light chain CDR2 comprising SEQ ID NO: 78, and a light chain CDR3 comprising SEQ ID NO: 80. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 87. In some embodiments, the GPRC5D-specific antibodies and antigen-binding fragments comprise a heavy chain variable domain substantially the same as, or identical to, SEQ ID NO: 87 and a light chain variable domain substantially the same as, or identical to, SEQ ID NO: 92. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 64, a heavy chain CDR2 comprising SEQ ID NO: 70, and a heavy chain CDR3 comprising SEQ ID NO: 12. In some embodiments, the GPRC5D-specific antibodies and antigen-binding fragments comprise a heavy chain CDR1 comprising SEQ ID NO: 64, a heavy chain CDR2 comprising SEQ ID NO: 70, a heavy chain CDR3 comprising SEQ ID NO: 12, a light chain CDR1 comprising SEQ ID NO: 15, a light chain CDR2 comprising SEQ ID NO: 18, and a light chain CDR3 comprising SEQ ID NO: 21. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 88. In some embodiments, the GPRC5D-specific antibodies and antigen-binding fragments comprise a heavy chain variable domain substantially the same as, or identical to, SEQ ID NO: 88 and a light chain variable domain substantially the same as, or identical to, SEQ ID NO: 58. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 65, a heavy chain CDR2 comprising SEQ ID NO: 68, and a heavy chain CDR3 comprising SEQ ID NO: 76. In some embodiments, the GPRC5D-specific antibodies and antigen-binding fragments comprise a heavy chain CDR1 comprising SEQ ID NO: 65, a heavy chain CDR2 comprising SEQ ID NO: 68, a heavy chain CDR3 comprising SEQ ID NO: 76, a light chain CDR1 comprising SEQ ID NO: 95, a light chain CDR2 comprising SEQ ID NO: 79, and a light chain CDR3 comprising SEQ ID NO: 81. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 89. In some embodiments, the GPRC5D-specific antibodies and antigen-binding fragments comprise a heavy chain variable domain substantially the same as, or identical to, SEQ ID NO: 89 and a light chain variable domain substantially the same as, or identical to, SEQ ID NO: 93. The heavy chain variable domain and light chain variable domain of antibodies discussed in this paragraph are suitable for inclusion in bispecific constructs in which one arm is an anti-GPRC5D arm.

In some embodiments, the GPRC5D-specific antibodies and antigen-binding fragments comprise a heavy chain CDR1 comprising SEQ ID NO: 66, a heavy chain CDR2 comprising SEQ ID NO: 71, and a heavy chain CDR3 comprising SEQ ID NO: 77. In some embodiments, the GPRC5D-specific antibodies and antigen-binding fragments comprise a heavy chain CDR1 comprising SEQ ID NO: 66, a heavy chain CDR2 comprising SEQ ID NO: 71, a heavy chain CDR3 comprising SEQ ID NO: 77, a light chain CDR1 comprising SEQ ID NO: 15, a light chain CDR2 comprising SEQ ID NO: 18, and a light chain CDR3 comprising SEQ ID NO: 21. This GPRC5D-specific antibody or antigen-binding fragment may comprise human framework sequences. In some embodiments, the GPRC5D-specific antibodies and antigen-binding fragments comprise a heavy chain variable domain substantially the same as, or identical to, SEQ ID NO: 91. In some embodiments, the GPRC5D-specific antibodies and antigen-binding fragments comprise a heavy chain variable domain substantially the same as, or identical to, SEQ ID NO: 91 and a light chain variable domain substantially the same as, or identical to, SEQ ID NO: 94. The heavy chain variable domain and light chain variable domain of antibodies discussed in this paragraph are suitable for inclusion in bispecific constructs in which one arm is an anti-GPRC5D arm.

In some embodiments, the antibodies or antigen-binding fragments are IgG, or derivatives thereof, e.g., IgG1, IgG2, IgG3, and IgG4 isotypes. In some embodiments wherein the antibody is of IgG1 isotype, the antibody comprises an IgG1 Fc region (SEQ ID NO: 60).

SEQ ID NO. 60
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

-continued
DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK

In some embodiments wherein the antibody is of IgG4 isotype, the antibody contains S228P, L234A, and L235A substitutions in its Fc region (SEQ ID NO. 59).

SEQ ID NO. 59
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEAAGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK

The specific antibodies defined by CDR and/or variable domain sequence discussed in the above paragraphs may include these modifications.

Also disclosed are isolated polynucleotides that encode the antibodies or antigen-binding fragments that immunospecifically bind to GPRC5D. The isolated polynucleotides capable of encoding the variable domain segments provided herein may be included on the same, or different, vectors to produce antibodies or antigen-binding fragments. An exemplary polynucleotide sequence that encodes a GPRC5D antibody is shown below:

Heavy Chain Sequence (SEQ ID NO: 96):
atggcctgggtctggaccctgctgttcctgatggccgctgcccagagca tccaggcccaggtgcagctggtgcagagcggcgccgaggtgaagaagcc cggcgccagcgtgaaggtgagctgcaaggccagcggctacagcttcacc ggctacaccatgaactgggtgcggcaggcccccggccagggcctggagt ggatgggcctgatcaaccctacaacagcgacaccaactacgcccagaa gctgcagggccgggtgaccatgaccaccgacaccagcaccagcaccgcc tacatggagctgcggagcctgcggagcgacgacaccgccgtgtactact gcgcccgggtggccctgcgggtggccctggactactggggccagggcac cctggtgaccgtgagcagcgcctccaccaagggcccatccgtcttcccc ctggcgccctgctccaggagcacctccgagagcacagccgccctgggct gcctggtcaaggactacttccccgaaccggtgacggtgtcgtggaactc aggcgccctgaccagcggcgtgcacaccttcccggctgtcctacagtcc tcaggactctactccctcagcagcgtggtgaccgtgccctccagcagct tgggcacgaaaacctacacctgcaacgtagatcacaagcccagcaacac caaggtggacaagagagttgagtccaaatatggtccccatgcccacca tgcccagcacctgaggccgccggggaccatcagtcttcctgttccccc caaaacccaaggacactctcatgatctcccggacccctgaggtcacgtg cgtggtggtggacgtgagccaggaagaccccgaggtccagttcaactgg -continued

```
tacgtggatggcgtggaggtgcataatgccaagacaaagccgcgggagg
agcagttcaacagcacgtaccgtgtggtcagcgtcctcaccgtcctgca
ccaggactggctgaacggcaaggagtacaagtgcaaggtctccaacaaa
ggcctcccgtcctccatcgagaaaaccatctccaaagccaaagggcagc
cccgagagccacaggtgtacaccctgcccccatcccaggaggagatgac
caagaaccaggtcagcctgacctgcctggtcaaaggcttctacccagc
gacatcgccgtggagtgggagagcaatgggcagccggagaacaactaca
agaccacgcctcccgtgctggactccgacggctccttcttcctctacag
caggctaaccgtggacaagagcaggtggcaggaggggaatgtcttctca
tgctccgtgatgcatgaggctctgcacaaccactacacacagaagagcc
tctccctgtctctgggtaaatga
```

Light Chain Sequence (SEQ ID NO: 90):

```
atgcgggtgctggcccagctgctgggactgctgctgctgtgcttccctg
gcgccagatgcgacatccagatgacccagagcccagcagcctgagcgc
cagcgtgggcgaccgggtgaccatcacctgcaaggccagccagaacgtg
gccaccacgtgggctggtaccagcagaagcccggcaaggcccccaagc
ggctgatctacagcgccagctaccggtacagcggcgtgcccagccggtt
cagcggcagcggcagcggcaccgagttcaccctgaccatcagcaacctg
cagcccgaggacttcgccacctactactgccagcagtacaaccggtacc
cctacaccttcggccagggcaccaagctggagatcaagcgtacggtggc
tgcaccatctgtcttcatcttcccgccatctgatgagcagttgaaatct
ggaactgcctctgttgtgtgcctgctgaataacttctatcccagagagg
ccaaagtacagtggaaggtggataacgccctccaatcgggtaactccca
ggagagtgtcacagagcaggacagcaaggacagcacctacagcctcagc
agcaccctgacgctgagcaaagcagactacgagaaacacaaagtctacg
cctgcgaagtcacccatcagggcctgagctcgcccgtcacaaagagctt
caacaggggagagtgttga
```

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The GPRC5D-specific antibodies or antigen-binding fragments described herein include variants having single or multiple amino acid substitutions, deletions, or additions that retain the biological properties (e.g., binding affinity or immune effector activity) of the described GPRC5D-specific antibodies or antigen-binding fragments. In the context of the present invention the following notations are, unless otherwise indicated, used to describe a mutation; i) substitution of an amino acid in a given position is written as e.g. S228P which means a substitution of a Serine in position 228 with a Proline; and ii) for specific variants the specific three or one letter codes are used, including the codes Xaa and X to indicate any amino acid residue. Thus, the substitution of Serine for Arginine in position 228 is designated as: S228P, or the substitution of any amino acid residue for Serine in position 228 is designated as S228P. In case of deletion of Serine in position 228 it is indicated by S228*. The skilled person may produce variants having single or multiple amino acid substitutions, deletions, or additions.

These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The GPRC5D-specific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 or IgG4 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 Mol. Cell. Biol. 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the GPRC5D-specific antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene, a puromycin resistance gene, a blasticidin resistance gene), glutamate synthase genes, HSV-TK, HSV-TK derivatives for ganciclovir selection, or bacterial purine nucleoside phosphorylase gene for 6-methylpurine selection (Gadi et al., 7 Gene Ther. 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate GPRC5D-specific antibody or antigen-binding fragment-producing cells. Thus, another aspect features host cells transformed with vectors comprising a nucleic acid sequence encoding an antibody or antigen-binding fragment thereof that specifically binds GPRC5D, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 Pharmac. Ther. 69-92 (1985)). Calcium phosphate precipitation and polyethylene glycol (PEG)-induced fusion of bacterial protoplasts with mammalian cells may also be used to transform cells.

Cells suitable for use in the expression of the GPRC5D-specific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Methods of Using GPRC5D-Specific Antibodies for Treatment

Provided herein are GPRC5D-specific antibodies or antigen-binding fragments thereof for use in therapy. In particular, these antibodies or antigen-binding fragments may be useful in treating cancer, such as GPRC5D-expressing cancer. Accordingly, the invention provides a method of treating cancer comprising administering an antibody as described herein, such as GPRC5D-specific antibodies or antigen-binding fragments. For example, the use may be by interfering with GPRC5D-receptor interactions or where the antibody is conjugated to a toxin, so targeting the toxin to the GPRC5D-expressing cancer. In some embodiments GPRC5D-expressing cancer includes lymphoma, such as multiple myeloma (MM). The antibodies for use in these methods include those described herein above, for example a GPRC5D-specific antibody or antigen-binding fragment with the features set out in Table 1, for example the CDRs or variable domain sequences, and in the further discussion of these antibodies.

In some embodiments described herein, immune effector properties of the GPRC5D-specific antibodies may be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. may be provided and/or controlled by modifying residues in the Fc responsible for these activities.

"Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of monoclonal antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved Fc.gamma.RIIIa binding without altering antigen binding or CDC activity. Such mAbs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the .alpha. 1,6-fucosyltrasferase (FUT8) gene (Mori et al., Biotechnol Bioeng 88:901-908, 2004), or coexpression of β-1, 4-N-acetylglucosaminyltransferase III and golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the GPRC5D antibodies may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

Methods of Detecting GPRC5D

Provided herein are methods for detecting GPRC5D in a biological sample by contacting the sample with an antibody, or antigen-binding fragment thereof, described herein. As described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the described methods include detecting GPRC5D in a biological sample by contacting the sample with any of the GPRC5D-specific antibodies or antigen-binding fragments thereof described herein.

In some embodiments the sample may be contacted with more than one of the GPRC5D-specific antibodies or antigen-binding fragments described herein. For example, a sample may be contacted with a first GPRC5D-specific antibody, or antigen-binding fragment thereof, and then contacted with a second GPRC5D-specific antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

The described GPRC5D-specific antibodies and antigen-binding fragments may be detectably labeled. In some embodiments labeled antibodies and antigen-binding fragments may facilitate the detection GPRC5D via the methods described herein. Many such labels are readily known to those skilled in the art. For example, suitable labels include, but should not be considered limited to, radiolabels, fluorescent labels, epitope tags, biotin, chromophore labels, ECL labels, or enzymes. More specifically, the described labels include ruthenium, $^{111}$In—DOTA, $^{111}$In—diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like.

The described GPRC5D-specific antibodies and antigen-binding fragments may be used in a variety of assays to detect GPRC5D in a biological sample. Some suitable assays include, but should not be considered limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In some embodiments described herein detection of GPRC5D-expressing cancer cells in a subject may be used to determine that the subject may be treated with a therapeutic agent directed against GPRC5D.

GPRC5D is present at detectable levels in blood and serum samples. Thus, provided herein are methods for detecting GPRC5D in a sample derived from blood, such as a serum sample, by contacting the sample with an antibody, or antigen-binding fragment thereof, that specifically binds GPRC5D. The blood sample, or a derivative thereof, may be diluted, fractionated, or otherwise processed to yield a sample upon which the described method may be performed. In some embodiments, GPRC5D may be detected in a blood sample, or a derivative thereof, by any number of assays known in the art, such as, but not limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Methods for Diagnosing Cancer

Provided herein are methods for diagnosing GPRC5D-expressing cancer in a subject. In some embodiments GPRC5D-expressing cancer include lymphomas, such as multiple myeloma (MM). In some embodiments, as described above, detecting GPRC5D in a biological sample, such as a blood sample or a serum sample, provides the ability to diagnose cancer in the subject from whom the sample was obtained. Alternatively, in some embodiments other samples such as a histological sample, a fine needle aspirate sample, resected tumor tissue, circulating cells, circulating tumor cells, and the like, may also be used to assess whether the subject from whom the sample was obtained has cancer. In some embodiments, it may already be known that the subject from whom the sample was obtained has cancer, but the type of cancer afflicting the subject may not yet have been diagnosed or a preliminary diagnosis may be unclear, thus detecting GPRC5D in a biological sample obtained from the subject can allow for, or clarify, diagnosis of the cancer. For example, a subject may be known to have cancer, but it may not be known, or may be unclear, whether the subject's cancer is GPRC5D-expressing.

In some embodiments the described methods involve assessing whether a subject is afflicted with GPRC5D-expressing cancer by determining the amount of GPRC5D that is present in a biological sample derived from the subject; and comparing the observed amount of GPRC5D with the amount of GPRC5D in a control, or reference, sample, wherein a difference between the amount of GPRC5D in the sample derived from the subject and the amount of GPRC5D in the control, or reference, sample is an indication that the subject is afflicted with a GPRC5D-expressing cancer. In another embodiment the amount of GPRC5D observed in a biological sample obtained from a subject may be compared to levels of GPRC5D known to be associated with certain forms or stages of cancer, to determine the form or stage of the subject's cancer. In some embodiments the amount of GPRC5D in the sample derived from the subject is assessed by contacting the sample with an antibody, or an antigen-binding fragment thereof, that immunospecifically binds GPRC5D, such as the GPRC5D-specific antibodies described herein.

The sample assessed for the presence of GPRC5D may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments GPRC5D-expressing cancer includes hematological cancer, such as multiple myeloma (MM). In some embodiments the subject is a human.

In some embodiments the method of diagnosing a GPRC5D-expressing cancer will involve: contacting a biological sample of a subject with a GPRC5D-specific antibody, or an antigen-binding fragment thereof (such as those derivable from the antibodies and fragments provided in Table 1), quantifying the amount of GPRC5D present in the sample that is bound by the antibody or antigen-binding fragment thereof, comparing the amount of GPRC5D present in the sample to a known standard or reference sample; and determining whether the subject's GPRC5D levels fall within the levels of GPRC5D associated with cancer. In an additional embodiment, the diagnostic method can be followed with an additional step of administering or prescribing a cancer-specific treatment. In another embodiment, the diagnostic method can be followed with an additional step of transmitting the results of the determination to facilitate treatment of the cancer. In some embodiments the cancer-specific treatment may be directed against GPRC5D-expressing cancers, such as the GPRC5D x CD3 multispecific antibodies described herein.

In some embodiments the described methods involve assessing whether a subject is afflicted with GPRC5D-expressing cancer by determining the amount of GPRC5D present in a blood or serum sample obtained from the subject; and comparing the observed amount of GPRC5D with the amount of GPRC5D in a control, or reference, sample, wherein a difference between the amount of GPRC5D in the sample derived from the subject and the amount of GPRC5D in the control, or reference, sample is an indication that the subject is afflicted with a GPRC5D-expressing cancer.

In some embodiments the control, or reference, sample may be derived from a subject that is not afflicted with GPRC5D-expressing cancer. In some embodiments the control, or reference, sample may be derived from a subject that is afflicted with GPRC5D-expressing cancer. In some embodiments where the control, or reference, sample is derived from a subject that is not afflicted with GPRC5D-expressing cancer, an observed increase in the amount of GPRC5D present in the test sample, relative to that observed for the control or reference sample, is an indication that the subject being assessed is afflicted with GPRC5D-expressing cancer. In some embodiments where the control sample is derived from a subject that is not afflicted with GPRC5D-expressing cancer, an observed decrease or similarity in the amount of GPRC5D present in the test sample, relative to that observed for the control or reference sample, is an indication that the subject being assessed is not afflicted with GPRC5D-expressing cancer. In some embodiments where the control or reference sample is derived from a subject that is afflicted with GPRC5D-expressing cancer, an observed similarity in the amount of GPRC5D present in the test sample, relative to that observed for the control or reference sample, is an indication that the subject being assessed is afflicted with GPRC5D-expressing cancer. In some embodiments where the control or reference sample is derived from a subject that is afflicted with GPRC5D-expressing cancer, an observed decrease in the amount of GPRC5D present in the test sample, relative to that observed for the control or reference sample, is an indication that the subject being assessed is not afflicted with GPRC5D-expressing cancer.

In some embodiments the amount of GPRC5D in the sample derived from the subject is assessed by contacting the sample with an antibody, or an antigen-binding fragment thereof, that specifically binds GPRC5D, such as the antibodies described herein. The sample assessed for the presence of GPRC5D may be derived from a blood sample, a serum sample, circulating cells, circulating tumor cells, cells that are not tissue associated (i.e., free cells), tissues (e.g., surgically resected tumor tissue, biopsies, including fine needle aspiration), histological preparations, and the like.

In various aspects, the amount of GPRC5D is determined by contacting the sample with an antibody, or antigen-binding fragment thereof, that specifically binds GPRC5D. In some embodiments, the sample may be contacted by more than one type of antibody, or antigen-binding fragment thereof, that specifically binds GPRC5D. In some embodiments, the sample may be contacted by a first antibody, or antigen-binding fragment thereof, that specifically binds GPRC5D and then contacted by a second antibody, or antigen-binding fragment thereof, that specifically binds GPRC5D. GPRC5D-specific antibodies or antigen-binding fragments such as those described herein may be used in this capacity.

Various combinations of the GPRC5D-specific antibodies and antigen-binding fragments can be used to provide a "first" and "second" antibody or antigen-binding fragment to carry out the described diagnostic methods. In some embodiments GPRC5D-expressing cancer includes lymphomas, such as multiple myeloma (MM).

In certain embodiments, the amount of GPRC5D is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In various embodiments of the described diagnostic methods a control or reference sample is used. This sample may be a positive or negative assay control that ensures the assay used is working properly; for example, an assay control of this nature might be commonly used for immunohistochemistry assays. Alternatively, the sample may be a standardized reference for the amount of GPRC5D in a biological sample from a healthy subject. In some embodiments, the observed GPRC5D levels of the tested subject may be compared with GPRC5D levels observed in samples from subjects known to have GPRC5D-expressing cancer. In some embodiments, the control subject may be afflicted with a particular cancer of interest. In some embodiments, the control subject is known to have early stage cancer, which may or may not be GPRC5D-expressing cancer. In some embodiments, the control subject is known to have intermediate stage cancer, which may or may not be GPRC5D-expressing cancer. In some embodiments, the control subject is known to have late stage, which may or may not be GPRC5D-expressing cancer.

Methods for Monitoring Cancer

Provided herein are methods for monitoring GPRC5D-expressing cancer in a subject. In some embodiments GPRC5D-expressing cancer includes lymphomas, such as multiple myeloma (MM). In some embodiments the described methods involve assessing whether GPRC5D-expressing cancer is progressing, regressing, or remaining stable by determining the amount of GPRC5D that is present in a test sample derived from the subject; and comparing the observed amount of GPRC5D with the amount of GPRC5D in a biological sample obtained, in a similar manner, from the subject at an earlier point in time, wherein a difference between the amount of GPRC5D in the test sample and the earlier sample provides an indication of whether the cancer is progressing, regressing, or remaining stable. In this regard, a test sample with an increased amount of GPRC5D, relative to the amount observed for the earlier sample, may indicate progression of a GPRC5D-expressing cancer. Conversely, a test sample with a decreased amount of GPRC5D, relative to the amount observed for the earlier sample, may indicate regression of a GPRC5D-expressing cancer.

Accordingly, a test sample with an insignificant difference in the amount of GPRC5D, relative to the amount observed for the earlier sample, may indicate a state of stable disease for a GPRC5D-expressing cancer. In some embodiments the amount of GPRC5D in a biological sample derived from the subject is assessed by contacting the sample with an antibody, or an antibody fragment thereof, that specifically binds GPRC5D, such as the antibodies described herein. The sample assessed for the presence of GPRC5D may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the subject is a human.

In some embodiments the methods of monitoring a GPRC5D-expressing cancer will involve: contacting a biological sample of a subject with a GPRC5D-specific antibody, or antigen-binding fragment thereof (such as those derivable from the antibodies and fragments provided in Table 1), quantifying the amount of GPRC5D present in the sample, comparing the amount of GPRC5D present in the sample to the amount of GPRC5D determined to be in a biological sample obtained, in a similar manner, from the same subject at an earlier point in time; and determining whether the subject's GPRC5D level has changed over time. A test sample with an increased amount of GPRC5D, relative to the amount observed for the earlier sample, may indicate progression of cancer. Conversely, a test sample with a decreased amount of GPRC5D, relative to the amount observed for the earlier sample, may indicate regression of a GPRC5D-expressing cancer. Accordingly, a test sample with an insignificant difference in the amount of GPRC5D, relative to the amount observed for the earlier sample, may indicate a state of stable disease for a GPRC5D-expressing cancer. In some embodiments, the GPRC5D levels of the sample may be compared to a known standard or a reference sample, alone or in addition to the GPRC5D levels observed for a sample assessed at an earlier point in time. In an additional embodiment, the diagnostic method can be followed with an additional step of administering a cancer-specific treatment. In some embodiments the cancer-specific treatment may be directed against GPRC5D-expressing cancers.

In various aspects, the amount of GPRC5D is determined by contacting the sample with an antibody, or antigen-binding fragment thereof, that specifically binds GPRC5D. In some embodiments, the sample may be contacted by more than one type of antibody, or antigen-binding fragment thereof, that specifically binds GPRC5D. In some embodiments, the sample may be contacted by a first antibody, or antigen-binding fragment thereof, that specifically binds GPRC5D and then contacted by a second antibody, or antigen-binding fragment thereof, that specifically binds GPRC5D. Antibodies such as those described herein may be used in this capacity.

Various combinations of the antibodies and antigen-binding fragments described in Table 1 can be used to provide a "first" and "second" antibody or antigen-binding fragment to carry out the described monitoring methods. In some embodiments GPRC5D-expressing cancer includes a hematological cancer, such as multiple myeloma (MM).

In certain embodiments, the amount of GPRC5D is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Kits for Detecting GPRC5D

Provided herein are kits for detecting GPRC5D in a biological sample. These kits include one or more of the GPRC5D-specific antibodies described herein, or an antigen-binding fragment thereof, and instructions for use of the kit.

The provided GPRC5D-specific antibody, or antigen-binding fragment, may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of GPRC5D can further include, for example, buffers or other reagents for use in an assay for determining the level of GPRC5D. The instructions can be, for example, printed instructions for performing the assay and/or instructions for evaluating the level of expression of GPRC5D.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

Multispecific Antibodies

The binding domains of the anti-GPRC5D antibodies described herein recognize cells expressing GPRC5D on their surface. As noted above, GPRC5D expression can be indicative of a cancerous cell. More specific targeting to particular subsets of cells can be achieved by making bispecific molecules, such as antibodies or antibody fragments, which bind to GPRC5D and to another target, such as CD3 and BCMA. This is achieved by making a molecule which comprises a first region binding to GPRC5D and a second binding region binding to the other target antigen. The antigen-binding regions can take any form that allows specific recognition of the target, for example the binding region may be or may include a heavy chain variable domain, an Fv (combination of a heavy chain variable domain and a light chain variable domain), a binding domain based on a fibronectin type III domain (such as from fibronectin, or based on a consensus of the type III domains from fibronectin, or from tenascin or based on a consensus of the type III domains from tenascin, such as the Centyrin molecules from Janssen Biotech, Inc., see e.g. WO2010/051274 and WO2010/093627). Accordingly, bispecific molecules comprising two different antigen-binding regions which bind GPRC5D and another antigen, respectively, are provided.

Some of the multispecific antibodies described herein comprise two different antigen-binding regions which bind GPRC5D and CD3, respectively. In preferred embodiments, multispecific antibodies that bind GPRC5D and CD3 (GPRC5D x CD3-multispecific antibodies) and multispecific antigen-binding fragments thereof are provided. In some embodiments, the GPRC5D x CD3-multispecific antibody comprises a first heavy chain (HC1) and a first light chain (LC1) that pair to form a first antigen-binding site that specifically binds GPRC5D and a second heavy chain (HC2) and a second light chain (LC2) that pair to form a second antigen-binding site that specifically binds CD3. In preferred embodiments, the GPRC5D x CD3-multispecific antibody is a bispecific antibody comprising a GPRC5D-specific arm comprising a first heavy chain (HC1) and a first light chain (LC1) that pair to form a first antigen-binding site that specifically binds CD3 and a CD3-specific arm comprising second heavy chain (HC2) and a second light chain (LC2) that pair to form a second antigen-binding site that specifically binds GPRC5D. In some embodiments, the bispecific antibodies of the invention include antibodies having a full length antibody structure. "Full length antibody" as used herein refers to an antibody having two full length antibody heavy chains and two full length antibody light chains. A full length antibody heavy chain (HC) includes heavy chain variable and constant domains VH, CH1, CH2, and CH3. A full length antibody light chain (LC) includes light chain variable and constant domains VL and CL. The full length antibody may be lacking the C-terminal lysine (K) in either one or both heavy chains. The term "Fab-arm" or "half molecule" refers to one heavy chain-light chain pair that specifically binds an antigen. In some embodiments, one of the antigen-binding domains is a non-antibody based binding domain, e.g. a binding domain of based on a fibronectin type 3 domain, e.g. Centyrin.

The GPRC5D-binding arm of the multispecific antibodies provided herein may be derived from any of the GPRC5D-specific antibodies described above. In some exemplary embodiments of such GPRC5D-binding arms, the first antigen-binding region which binds GPRC5D comprises a heavy chain CDR1, CDR2, and CDR3 derived from an antibody clone as described in Table 1. In some exemplary embodiments of such GPRC5D-binding arms, the first antigen-binding region which binds GPRC5D comprises heavy chain CDR1, CDR2, and CDR3 and light chain CDR1, CDR2, and CDR3 derived from an antibody clone as described in Table 1. In some exemplary embodiments of such GPRC5D-binding arms, the first antigen-binding region which binds GPRC5D comprises heavy chain CDR1, CDR2, and CDR3 of clone GC5B81, GC5B465, GS5B483, GC5B596, GC5B382, GC5B379, GC5B373, GC5B376, GC5B385, GC5B370, GC5B602, GC5B603, GC5B599, GC5B601, GC5B598, or GC5B597.

In some exemplary embodiments of such GPRC5D-binding arms, the first antigen-binding region which binds GPRC5D comprises heavy chain CDR1, CDR2, and CDR3 and light chain CDR1, CDR2, and CDR3 of clone GC5B81, GC5B465, GS5B483 or GC5B596. In some exemplary embodiments of such GPRC5D-binding arms, the first antigen-binding region which binds GPRC5D comprises a heavy chain variable domain derived from an antibody clone as described in Table 1. In some exemplary embodiments of such GPRC5D-binding arms, the first antigen-binding region which binds GPRC5D comprises heavy chain variable domain and light chain variable domain derived from an antibody clone as described in Table 1. In some exemplary embodiments of such GPRC5D-binding arms, the first antigen-binding region which binds GPRC5D comprises heavy chain variable domain of clone GC5B81, GC5B465, GS5B483 or GC5B596. In some exemplary embodiments of such GPRC5D-binding arms, the first antigen-binding region which binds GPRC5D comprises heavy chain variable domain and light chain variable domain of clone GC5B81, GC5B465, GS5B483, GC5B596, GC5B382, GC5B379, GC5B373, GC5B376, GC5B385, GC5B370, GC5B602, GC5B603, GC5B599, GC5B601, GC5B598, or GC5B597.

Table 3 provides a listing of GPRC5D x CD3 bi-specific antibodies having one heavy and light chain pair specific for GPRC5D and another heavy and light chain pair specific for CD3, where the particular antibody ID is listed to describe the antigen-specific antibody arms used to produce the described embodiment.

TABLE 3

| GPRC5D-specific arm = Ab ID | CD3-specific arm = Ab ID |
|---|---|
| GC5B81 | CD3B219 |
| GC5B465 | CD3B219 |
| GC5B483 | CD3B219 |
| GC5B596 | CD3B219 |
| GC5B382 | CD3B219 |
| GC5B379 | CD3B219 |
| GC5B373 | CD3B219 |
| GC5B376 | CD3B219 |
| GC5B385 | CD3B219 |
| GC5B370 | CD3B219 |
| GC5B602 | CD3B219 |
| GC5B603 | CD3B219 |
| GC5B599 | CD3B219 |
| GC5B601 | CD3B219 |
| GC5B598 | CD3B219 |
| GC5B597 | CD3B219 |

In some embodiments of the bispecific antibodies, the GPRC5D-binding arm binds also binds cynomolgus GPRC5D, preferably the extracellular domain thereof.

In some embodiments, the GPRC5D-binding arm of the multispecific antibody is IgG, or a derivative thereof, e.g., IgG1, IgG2, IgG3, and IgG4 isotypes. In some embodiments wherein the GPRC5D-binding arm has an IgG4 isotype, it contains S228P, L234A, and L235A substitution(s) in its Fc region.

In some embodiments of the bispecific antibodies, the second antigen-binding arm binds human CD3. In some preferred embodiments, the CD3-specific arm of the GPRC5D x CD3 bispecific antibody is derived from a CD3-specific antibody that binds and activates human primary T cells and/or cynomolgus monkey primary T cells. In some embodiments, the CD3-binding arm binds to an epitope at the N-terminus of CD3ε. In some embodiments, the CD3-binding arm contacts an epitope including the six N-terminal amino acids of CD3ε. In some embodiments, the CD3-specific binding arm of the bispecific antibody is derived from the mouse monoclonal antibody SP34, a mouse IgG3/lambda isotype. In some embodiments, the CD3-binding arm comprises the CDRs of antibody SP34. Such CD3-binding arms may bind to CD3 with an affinity of $5 \times 10^{-7}$M or less, such as $1 \times 10^{-7}$M or less, $5 \times 10^{-8}$M or less, $1 \times 10^{-8}$M or less, $5 \times 10^{-9}$M or less, or $1 \times 10^{-9}$M or less. The CD3-specific binding arm may be a humanized version of an arm of mouse monoclonal antibody SP34. Human framework adaptation (HFA) may be used to humanize the anti-CD3 antibody from which the CD3-specific arm is derived. In some embodiments of the bispecific antibodies, the CD3-binding arm comprises a heavy chain and light chain pair selected from Table 2.

In some embodiments, the CD3-binding arm is IgG, or a derivative thereof. In some embodiments, the CD3-binding arm is IgG1, IgG2, IgG3, or IgG4. In some embodiments where in the CD3-binding arm has an IgG4 isotype, it contains S228P, L234A, L235A, F405L, and R409K substitution(s) in its Fc region. In some embodiments, the antibodies or antigen-binding fragments bind CD3ε on primary human T cells. In some embodiments, the antibodies or antigen-binding fragments bind CD3ε on primary cynomolgus T cells. In some embodiments, the antibodies or antigen-binding fragments bind CD3ε on primary human and cynomolgus T cells. In some embodiments, the antibodies or antigen-binding fragments activate primary human CD3+ T cells. In some embodiments, the antibodies or antigen-binding fragments activate primary cynomolgus CD4+ T cells.

In some embodiments are provided a GPRC5D x CD3 bispecific antibody having a GPRC5D-binding arm comprising a heavy chain of antibody clone GC5B81, GC5B465, GS5B483, GC5B596, GC5B382, GC5B379, GC5B373, GC5B376, GC5B385, GC5B370, GC5B602, GC5B603, GC5B599, GC5B601, GC5B598, or GC5B597. In some embodiments are provided a GPRC5D x CD3 bispecific antibody having a GPRC5D-binding arm comprising a heavy chain and light chain of antibody clone GC5B81, GC5B465, GS5B483, GC5B596, GC5B382, GC5B379, GC5B373, GC5B376, GC5B385, GC5B370, GC5B602, GC5B603, GC5B599, GC5B601, GC5B598, or GC5B597. In some embodiments are provided a GPRC5D x CD3 bispecific antibody having a CD3-binding arm comprising a heavy chain of antibody clone CD3B219. In some embodiments are provided a GPRC5D x CD3 bispecific antibody having a CD3-binding arm comprising a heavy chain and light chain of antibody clone CD3B219. In some embodiments are provided a GPRC5D x CD3 bispecific antibody having a GPRC5D-binding arm comprising a heavy chain of antibody clone GC5B81, GC5B465, GS5B483, GC5B596, GC5B382, GC5B379, GC5B373, GC5B376, GC5B385, GC5B370, GC5B602, GC5B603, GC5B599, GC5B601, GC5B598, or GC5B597 and a CD3-binding arm comprising a heavy chain of antibody clone CD3B219. In some embodiments are provided a GPRC5D x CD3 bispecific antibody having a GPRC5D-binding arm comprising a heavy chain and light chain of antibody clone GC5B81, GC5B465, GS5B483, GC5B596, GC5B382, GC5B379, GC5B373, GC5B376, GC5B385, GC5B370, GC5B602, GC5B603, GC5B599, GC5B601, GC5B598, or GC5B597 and a CD3-binding arm comprising a heavy chain and light chain of antibody clone CD3B219.

An exemplary GPRC5D x CD3 bispecific antibody is provided in Table 23.

Different formats of bispecific antibodies have been described and were recently reviewed by Chames and Baty (2009) Curr Opin Drug Disc Dev 12:276.

In some embodiments, the bispecific antibody of the present invention is a diabody, a cross-body, or a bispecific antibody obtained via a controlled Fab arm exchange as those described in the present invention.

In some embodiments, the bispecific antibodies include IgG-like molecules with complementary CH3 domains to force heterodimerisation; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody)(EMD Serono), the Biclonic (Merus) and the DuoBody (Genmab A/S).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules include to ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv).sub.2-Fab (National Research Center for Antibody Medicine—China).

In some embodiments, Fab fusion bispecific antibodies include F(ab)2 (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv—, diabody-based and domain antibodies include but are not limited to Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Full length bispecific antibodies of the invention may be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each bind a distinct epitope, i.e. an epitope on GPRC5D and an epitope on CD3.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Intl. Publ. No. WO 2006/028936) may be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S L368A_Y407V.

Other strategies such as promoting heavy chain heterodimerization using electrostatic interactions by substituting positively charged residues at one CH3 surface and negatively charged residues at a second CH3 surface may be used, as described in US Pat. Publ. No. U.S. 2010/0015133; US Pat. Publ. No. U.S. 2009/0182127; U.S. Pat. Publ. No. U.S. 2010/028637 or US Pat. Publ. No. U.S. 2011/0123532. In other strategies, heterodimerization may be promoted by the following substitutions (expressed as modified position in the first CH3 domain of the first heavy chain/modified position in the second CH3 domain of the second heavy chain): L351Y_F405AY407V/T394W, T366I_K392M_T394W/F405A_Y407V, T366L_K392M_T394W/F405A_Y407V, L351Y_Y407A/T366A K409F, L351Y_Y407A/T366V_K409F_Y407A/T366A K409F, or T350V L351Y F405A Y407V/T350V T366L_K392L T394W as described in U.S. Pat. Publ. No. U.S. 2012/0149876 or U.S. Pat. Publ. No. US2013/0195849.

In addition to methods described above, bispecific antibodies of the invention may be generated in vitro in a cell-free environment by introducing asymmetrical mutations in the CH3 regions of two mono specific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody (e.g., anti-GPRC5D antibody) and the second monospecific bivalent antibody (e.g., anti-CD3 antibody) are engineered to have certain substitutions in the CH3 domain that promotes heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing conditions. Exemplary reducing agents that may be used are 2-mercaptoethylamine (2-MEA), dithiothreitol (DTT), dithioerythritol (DTE), glutathione, tris (2-carboxyethyl) phosphine (TCEP), L-cysteine and beta-mercaptoethanol, preferably a reducing agent selected from the group consisting of: 2-mercaptoethylamine, dithiothreitol and tris (2-carboxyethyl) phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 may be used.

In addition to the described GPRC5D x CD3-multispecific antibodies, also provided are polynucleotide sequences capable of encoding the described GPRC5D x CD3-multispecific antibodies. Vectors comprising the described polynucleotides are also provided, as are cells expressing the GPRC5D x CD3-multispecific antibodies provided herein.

Also described are cells capable of expressing the disclosed vectors. These cells may be mammalian cells (such as 293F cells, CHO cells), insect cells (such as Sf7 cells), yeast cells, plant cells, or bacteria cells (such as *E. coli*). The described antibodies may also be produced by hybridoma cells.

Therapeutic Composition and Methods of Treatment Using Multispecific Antibodies and Multispecific Antigen-Binding Fragments Thereof The GPRC5D bispecific antibodies discussed above, for example the GPRC5D x CD3 bispecific antibodies discussed above, are useful in therapy. In particular, the GPRC5D bispecific antibodies are useful in treating cancer. Also provided herein are therapeutic compositions for the treatment of a hyperproliferative disorder in a mammal which comprises a therapeutically effective amount of a multispecific antibody or multispecific antigen-binding fragment described herein and a pharmaceutically acceptable carrier. In preferred embodiments, the multispecific antibody is a GPRC5D x CD3-multispecific antibody as described herein, or a multispecific antigen-binding fragment thereof, and more preferably a GPRC5D x CD3-bispecific antibody as described herein, or a GPRC5D x CD3-bispecific antigen-binding fragment thereof. In one embodiment said pharmaceutical composition is for the treatment of a GPRC5D-expressing cancer, including (but not limited to) the following: GPRC5D-expressing B cell cancers, such as multiple myeloma (MM); and other cancers yet to be determined in which GPRC5D is expressed. Particular bispecific antibodies that may be used to treat cancer, such as hematological cancer, including the specific cancers discussed above, include antibodies GC5B81, GC5B465, GS5B483 or GC5B596.

The pharmaceutical compositions provided herein comprise: a) an effective amount of a multispecific antibody or antibody fragment of the present invention, and b) a pharmaceutically acceptable carrier, which may be inert or physiologically active. In preferred embodiments, the multispecific antibody is a GPRC5D x CD3-multispecific antibody as described herein, or a multispecific antigen-binding fragment thereof, and more preferably a GPRC5D x CD3-bispecific antibody as described herein, or a GPRC5D x CD3-bispecific antigen-binding fragment thereof. As used herein, the term "pharmaceutically acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as any combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH.about.7.4, containing or not containing about 1 mg/mL to 25 mg/mL human serum albumin, (2) 0.9% saline (0.9% w/v sodium chloride (NaCl)), and (3) 5% (w/v) dextrose; and may also contain an antioxidant such as tryptamine and a stabilizing agent such as Tween 20®.

The compositions herein may also contain a further therapeutic agent, as necessary for the particular disorder being treated. Preferably, the multispecific antibody or antibody fragment and the supplementary active compound will have complementary activities that do not adversely affect each other. In a preferred embodiment, the further therapeutic agent is cytarabine, an anthracycline, histamine dihydrochloride, or interleukin 2. In a preferred embodiment, the further therapeutic agent is a chemotherapeutic agent.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperitoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects.

Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohol's, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The multispecific antibody or antibody fragment may also be orally administered. As solid compositions for oral administration, tablets, pills, powders (gelatin capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The doses depend on the desired effect, the duration of the treatment and the route of administration used; they are generally between 5 mg and 1000 mg per day orally for an adult with unit doses ranging from 1 mg to 250 mg of active substance. In general, the doctor will determine the appropriate dosage depending on the age, weight and any other factors specific to the subject to be treated.

Also provided herein are methods for killing a GPRC5D+ cell by administering to a patient in need thereof a multi specific antibody which binds said GPRC5D and is able to recruit T cells to kill said GPRC5D+ cell (i.e., T cell redirection). Any of the multispecific antibodies or antibody fragments of the invention may be used therapeutically. For example, in one embodiment the GPRC5D x CD3-multispecific antibody may be used therapeutically to treat cancer in a subject.

In a preferred embodiment, multispecific antibodies or antibody fragments of the invention are used for the treatment of a hyperproliferative disorder in a mammal. In a more preferred embodiment, one of the pharmaceutical compositions disclosed above, and which contains a multispecific antibody or antibody fragment of the invention, is used for the treatment of a hyperproliferative disorder in a mammal. In one embodiment, the disorder is a cancer. In particular, the cancer is a GPRC5D-expressing cancer, including (but not limited to) the following: GPRC5D-expressing B-cell cancers, such as multiple myeloma (MM); and other cancers yet to be determined in which GPRC5D is expressed. In preferred embodiments, the multispecific antibody is a GPRC5D x CD3-multispecific antibody as described herein, or a multispecific antigen-binding fragment thereof, and more preferably a GPRC5D x CD3-bispecific antibody as described herein, or a GPRC5D x CD3-bispecific antigen-binding fragment thereof.

Accordingly, the pharmaceutical compositions of the invention are useful in the treatment or prevention of a variety of cancers, including (but not limited to) the following: a GPRC5D-expressing cancer, including (but not limited to) the following: GPRC5D-expressing B/Plasma cell cancers, such as acute multiple myeloma (MM) or premalignant myelomas such as MGUS (Monoclonal Gammopathy of Undetermined Significance) and SMM (Smoldering Multiple myeloma) and plasmacytoma; and other cancers yet to be determined in which GPRC5D is expressed.

Similarly, further provided herein is a method for inhibiting the growth of selected cell populations comprising contacting GPRC5D-expressing target cells, or tissue containing such target cells, with an effective amount of a multispecific antibody or antibody fragment of the present invention, either alone or in combination with other cytotoxic or therapeutic agents, in the presence of a peripheral blood mononuclear cell (PBMC). In preferred embodiments, the multispecific antibody is a GPRC5D x CD3-multispecific antibody as described herein, or a multispecific antigen-binding fragment thereof, and more preferably a GPRC5D x CD3-bispecific antibody as described herein, or a GPRC5D x CD3-bispecific antigen-binding fragment thereof. In a preferred embodiment, the further therapeutic agent is cytarabine, an anthracycline, histamine dihydrochloride, or interleukin 2. In a preferred embodiment, the further therapeutic agent is a chemotherapeutic agent. The method for inhibiting the growth of selected cell populations can be practiced in vitro, in vivo, or ex vivo.

Examples of in vitro uses include treatments of autologous bone marrow prior to their transplant into the same patient in order to kill diseased or malignant cells; treatments of bone marrow prior to its transplantation in order to kill competent T cells and prevent graft-versus-host-disease (GVHD); treatments of cell cultures in order to kill all cells except for desired variants that do not express the target antigen; or to kill variants that express undesired antigen. The conditions of non-clinical in vitro use are readily determined by one of ordinary skill in the art.

Examples of clinical ex vivo use are to remove tumor cells from bone marrow prior to autologous transplantation in cancer treatment. Treatment can be carried out as follows. Bone marrow is harvested from the patient or other individual and then incubated in medium containing serum to which is added the cytotoxic agent of the invention. Concentrations range from about 10 uM to 1 uM, for about 30 min to about 48 hr at about 37° C. The exact conditions of concentration and time of incubation, i.e., the dose, are readily determined by one of ordinary skill in the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, a therapeutically effective amount of the multispecific antibody or antigen-binding fragment is administered to a subject in need thereof. For example, the GPRC5D x CD3-multispecific antibodies and multispecific antigen-binding fragments thereof may be useful in the treatment of a GPRC5D-expressing cancer in a subject in need thereof. In some embodiments, the GPRC5D-expressing cancer is a B-cell cancer, such as multiple myeloma (MM). In preferred embodiments, the multispecific antibody is a GPRC5D x CD3-multispecific antibody as described herein, or a multispecific antigen-binding fragment thereof, and more preferably a GPRC5D x CD3-bispecific antibody as described herein, or a GPRC5D x CD3-bispecific antigen-binding fragment thereof. In some embodiments, the subject is a mammal, preferably a human. In some embodiments, the multispecific antibody or antigen-binding fragment will be administered as a solution that has been tested for sterility.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the multispecific antibodies and fragments depend on the disease or condition to be treated and may be determined by one skilled in the art. An exemplary, non-limiting range for a therapeutically effective amount of a compound of the present invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg.

A physician or veterinarian having ordinary skill in the art may readily determine and prescribe the effective amount of the pharmaceutical composition required. For example, the physician or veterinarian could start doses of the multispecific antibody or fragment employed in the pharmaceutical composition at levels lower than that required in order to achieve the desired therapeutic effect and gradually increase the dosage until the desired effect is achieved. In general, a suitable daily dose of a bispecific antibody of the present invention will be that amount of the compound which is the lowest dose effective to produce a therapeutic effect. Administration may e.g. be parenteral, such as intravenous, intramuscular or subcutaneous. In one embodiment, the multispecific antibody or fragment may be administered by infusion in a weekly dosage of calculated by mg/m$^2$. Such dosages can, for example, be based on the mg/kg dosages provided above according to the following: dose (mg/kg) x70:1.8. Such administration may be repeated, e.g., 1 to 8 times, such as 3 to 5 times. The administration may be performed by continuous infusion over a period of from 2 to 24 hr, such as of from 2 to 12 hr. In one embodiment, the multispecific antibody or fragment may be administered by slow continuous infusion over a long period, such as more than 24 hours, in order to reduce toxic side effects.

In one embodiment, the multispecific antibody or fragment may be administered in a weekly dosage of calculated as a fixed dose for up to eight times, such as from four to six times when given once a week. Such regimen may be repeated one or more times as necessary, for example, after six months or twelve months. Such fixed dosages can, for example, be based on the mg/kg dosages provided above, with a body weight estimate of 70 kg. The dosage may be determined or adjusted by measuring the amount of bispecific antibody of the present invention in the blood upon administration by for instance taking out a biological sample and using anti-idiotypic antibodies which target the GPRC5D antigen binding region of the multispecific antibodies of the present invention.

In one embodiment, the multispecific antibody or fragment may be administered by maintenance therapy, such as, e.g., once a week for a period of six months or more.

A multispecific antibody or fragment may also be administered prophylactically in order to reduce the risk of developing cancer, delay the onset of the occurrence of an event in cancer progression, and/or reduce the risk of recurrence when a cancer is in remission.

The multispecific antibodies and fragments thereof as described herein may also be administered in combination therapy, i.e., combined with other therapeutic agents relevant for the disease or condition to be treated. Accordingly, in one embodiment, the antibody-containing medicament is for combination with one or more further therapeutic agent, such as a chemotherapeutic agent. In some embodiments, the other therapeutic agent is cytarabine, an anthracycline, histamine dihydrochloride, or interleukin 2. Such combined administration may be simultaneous, separate or sequential, in any order. For simultaneous administration the agents may be administered as one composition or as separate compositions, as appropriate. In one embodiment, a method for treating a disorder involving cells expressing GPRC5D in a subject, which method comprises administration of a therapeutically effective amount of a multispecific antibody or fragment, such as a GPRC5D x CD3 bispecific antibody described herein, and radiotherapy to a subject in need thereof is provided. In one embodiment is provided a method for treating or preventing cancer, which method comprises administration of a therapeutically effective amount of a multispecific antibody or fragment, such as a GPRC5D x CD3 antibody described herein, and radiotherapy to a subject in need thereof. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

Kits

Also provided herein are includes kits, e.g., comprising a described multispecific antibody or antigen-binding fragment thereof and instructions for the use of the antibody or fragments for killing of particular cell types. In preferred embodiments, the multispecific antibody is a GPRC5D x CD3-multispecific antibody as described herein, or a multispecific antigen-binding fragment thereof, and more preferably a GPRC5D x CD3-bispecific antibody as described herein, or a GPRC5D x CD3-bispecific antigen-binding fragment thereof. The instructions may include directions for using the multispecific antibody or antigen-binding fragment thereof in vitro, in vivo or ex vivo.

Typically, the kit will have a compartment containing the multispecific antibody or antigen-binding fragment thereof. The multispecific antibody or antigen-binding fragment thereof may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the multispecific antibody or antigen-binding fragment thereof prior to administering to a patient, and tools that aid in administering the multispecific antibody or antigen-binding fragment thereof to a patient.

Diagnostic Uses

The multispecific antibodies and fragments described herein may also be used for diagnostic purposes. Thus, also provided are diagnostic compositions comprising a multispecific antibody or fragments as defined herein, and to its use. In preferred embodiments, the multispecific antibody is a GPRC5D x CD3-multispecific antibody as described herein, or a multispecific antigen-binding fragment thereof, and more preferably a GPRC5D x CD3-bispecific antibody as described herein, or a GPRC5D x CD3-bispecific antigen-binding fragment thereof. In one embodiment, the present invention provides a kit for diagnosis of cancer comprising a container comprising a bispecific GPRC5D x CD3 antibody, and one or more reagents for detecting binding of the antibody to GPRC5D. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. For example, the multispecific antibodies described herein, or antigen-binding fragments thereof, may be labeled with a radiolabel, a fluorescent label, an epitope tag, biotin, a chromophore label, an ECL label, an enzyme, ruthenium, In-DOTA, diethylenetriaminepentaacetic acid (DTPA), horseradish peroxidase, alkaline phosphatase and beta-galactosidase, or poly-histidine or similar such labels known in the art.

EMBODIMENTS

The disclosure provided herein also provides the following non-limiting embodiments.

1. An isolated antibody, or an antigen-binding fragment thereof, that binds specifically to GPRC5D comprising:

a. a heavy chain complementarity determining region 1 (CDR1) having the amino acid sequence of SEQ ID NO: 1, a heavy chain CDR2 having the amino acid sequence of SEQ ID NO: 5, and a heavy chain CDR3 having the amino acid sequence of SEQ ID NO: 9;

b. a heavy chain CDR1 having the amino acid sequence of SEQ ID NO: 2, a heavy chain CDR2 having the amino acid sequence of SEQ ID NO: 6, and a heavy chain CDR3 having the amino acid sequence of SEQ ID NO: 10;

c. a heavy chain CDR1 having the amino acid sequence of SEQ ID NO: 3, a heavy chain CDR2 having the amino acid sequence of SEQ ID NO: 7, and a heavy chain CDR3 having the amino acid sequence of SEQ ID NO: 11;

d. a heavy chain CDR1 having the amino acid sequence of SEQ ID NO: 4, a heavy chain CDR2 having the amino acid sequence of SEQ ID NO: 8, and a heavy chain CDR3 having the amino acid sequence of SEQ ID NO: 12;

e. a heavy chain CDR1 having the amino acid sequence of SEQ ID NO: 61, a heavy chain CDR2 having the amino acid sequence of SEQ ID NO: 67, and a heavy chain CDR3 having the amino acid sequence of SEQ ID NO: 72;

f. a heavy chain CDR1 having the amino acid sequence of SEQ ID NO: 2, a heavy chain CDR2 having the amino acid sequence of SEQ ID NO: 28, and a heavy chain CDR3 having the amino acid sequence of SEQ ID NO: 30;

g. a heavy chain CDR1 having the amino acid sequence of SEQ ID NO: 27, a heavy chain CDR2 having the amino acid sequence of SEQ ID NO: 29, and a heavy chain CDR3 having the amino acid sequence of SEQ ID NO: 73;

h. a heavy chain CDR1 having the amino acid sequence of SEQ ID NO: 27, a heavy chain CDR2 having the amino acid sequence of SEQ ID NO: 29, and a heavy chain CDR3 having the amino acid sequence of SEQ ID NO: 11;

i. a heavy chain CDR1 having the amino acid sequence of SEQ ID NO: 62, a heavy chain CDR2 having the amino acid sequence of SEQ ID NO: 68, and a heavy chain CDR3 having the amino acid sequence of SEQ ID NO: 74;

j. a heavy chain CDR1 having the amino acid sequence of SEQ ID NO: 63, a heavy chain CDR2 having the amino acid sequence of SEQ ID NO: 69, and a heavy chain CDR3 having the amino acid sequence of SEQ ID NO: 75;

k. a heavy chain CDR1 having the amino acid sequence of SEQ ID NO: 64, a heavy chain CDR2 having the amino acid sequence of SEQ ID NO: 70, and a heavy chain CDR3 having the amino acid sequence of SEQ ID NO: 12;

l. a heavy chain CDR1 having the amino acid sequence of SEQ ID NO: 65, a heavy chain CDR2 having the amino acid sequence of SEQ ID NO: 68, and a heavy chain CDR3 having the amino acid sequence of SEQ ID NO: 76; or m. a heavy chain CDR1 having the amino acid sequence of SEQ ID NO: 66, a heavy chain CDR2 having the amino acid sequence of SEQ ID NO: 71, and a heavy chain CDR3 having the amino acid sequence of SEQ ID NO: 77.

2. The isolated antibody, or an antigen-binding fragment of embodiment 1, wherein a. said antibody comprising said heavy chain CDR1 having the amino acid sequence of SEQ ID NO: 1, said heavy chain CDR2 having the amino acid sequence of SEQ ID NO: 5, and said heavy chain CDR3 having the amino acid sequence of SEQ ID NO: 9 further comprises a light chain CDR1 having the amino acid sequence of SEQ ID NO: 13, a light chain CDR2 having the amino acid sequence of SEQ ID NO: 16, and a light chain CDR3 having the amino acid sequence of SEQ ID NO: 19;

b. said antibody comprising said heavy chain CDR1 having the amino acid sequence of SEQ ID NO: 2, said heavy chain CDR2 having the amino acid sequence of SEQ ID NO: 6, and said heavy chain CDR3 having the amino acid sequence of SEQ ID NO: 10 further comprises a light chain CDR1 having the amino acid sequence of SEQ ID NO: 13, a light chain CDR2 having the amino acid sequence of SEQ ID NO: 16, and a light chain CDR3 having the amino acid sequence of SEQ ID NO: 19;

c. said antibody comprising said heavy chain CDR1 having the amino acid sequence of SEQ ID NO: 3, said heavy chain CDR2 having the amino acid sequence of SEQ ID NO: 7, and said heavy chain CDR3 having the amino acid sequence of SEQ ID NO: 11 further comprises a light chain CDR1 having the amino acid sequence of SEQ ID NO: 14, a light chain CDR2 having the amino acid sequence of SEQ ID NO: 17, and a light chain CDR3 having the amino acid sequence of SEQ ID NO: 20;

d. said antibody comprising said heavy chain CDR1 having the amino acid sequence of SEQ ID NO: 4, said heavy chain CDR2 having the amino acid sequence of SEQ ID NO: 8, and said heavy chain CDR3 having the amino acid sequence of SEQ ID NO: 12 further comprises a light chain CDR1 having the amino acid sequence of SEQ ID NO: 15, a light chain CDR2 having the amino acid sequence of SEQ ID NO: 18, and a light chain CDR3 having the amino acid sequence of SEQ ID NO: 21;

e. said antibody comprising said heavy chain CDR1 having the amino acid sequence of SEQ ID NO: 61, said heavy chain CDR2 having the amino acid sequence of SEQ ID NO: 67, and said heavy chain CDR3 having the amino acid sequence of SEQ ID NO: 72 further comprises a light chain CDR1 having the amino acid sequence of SEQ ID NO: 13, a light chain CDR2 having the amino acid sequence of SEQ ID NO: 78, and a light chain CDR3 having the amino acid sequence of SEQ ID NO: 80;

f. said antibody comprising said heavy chain CDR1 having the amino acid sequence of SEQ ID NO: 2, said heavy chain CDR2 having the amino acid sequence of SEQ ID NO: 28, and said heavy chain CDR3 having the amino acid sequence of SEQ ID NO: 30 further comprises a light chain CDR1 having the amino acid sequence of SEQ ID NO: 13, a light chain CDR2 having the amino acid sequence of SEQ ID NO: 6, and a light chain CDR3 having the amino acid sequence of SEQ ID NO: 19;

g. said antibody comprising said heavy chain CDR1 having the amino acid sequence of SEQ ID NO: 27, said heavy chain CDR2 having the amino acid sequence of SEQ ID NO: 29, and said heavy chain CDR3 having the amino acid sequence of SEQ ID NO: 73 further comprises a light chain CDR1 having the amino acid sequence of SEQ ID NO: 14, a light chain CDR2 having the amino acid sequence of SEQ ID NO: 17, and a light chain CDR3 having the amino acid sequence of SEQ ID NO: 20;

h. said antibody comprising said heavy chain CDR1 having the amino acid sequence of SEQ ID NO: 27, said heavy chain CDR2 having the amino acid sequence of SEQ ID NO: 29, and said heavy chain CDR3 having the amino acid sequence of SEQ ID NO: 11 further comprises a light chain CDR1 having the amino acid sequence of SEQ ID NO: 14, a light chain CDR2 having the amino acid sequence of SEQ ID NO: 17, and a light chain CDR3 having the amino acid sequence of SEQ ID NO: 20;

i. said antibody comprising said heavy chain CDR1 having the amino acid sequence of SEQ ID NO: 62, said heavy chain CDR2 having the amino acid sequence of SEQ ID NO: 68, and said heavy chain CDR3 having the amino acid sequence of SEQ ID NO: 74 further comprises a light chain CDR1 having the amino acid sequence of SEQ ID NO: 14, a light chain CDR2 having the amino acid sequence of SEQ ID NO: 17, and a light chain CDR3 having the amino acid sequence of SEQ ID NO: 20;

j. said antibody comprising said heavy chain CDR1 having the amino acid sequence of SEQ ID NO: 63, said heavy chain CDR2 having the amino acid sequence of SEQ ID NO: 69, and said heavy chain CDR3 having the amino acid sequence of SEQ ID NO: 75 further comprises a light chain CDR1 having the amino acid sequence of SEQ ID NO: 13, a light chain CDR2 having the amino acid sequence of SEQ ID NO: 78, and a light chain CDR3 having the amino acid sequence of SEQ ID NO: 80;

k. said antibody comprising said heavy chain CDR1 having the amino acid sequence of SEQ ID NO: 61, said heavy chain CDR2 having the amino acid sequence of SEQ ID NO: 67, and said heavy chain CDR3 having the amino acid sequence of SEQ ID NO: 72 further comprises a light chain CDR1 having the amino acid sequence of SEQ ID NO: 13, a light chain CDR2 having the amino acid sequence of SEQ ID NO: 78, and a light chain CDR3 having the amino acid sequence of SEQ ID NO: 80;

l. said antibody comprising said heavy chain CDR1 having the amino acid sequence of SEQ ID NO: 65, said heavy chain CDR2 having the amino acid sequence of SEQ ID NO: 68, and said heavy chain CDR3 having the amino acid sequence of SEQ ID NO: 76 further comprises a light chain CDR1 having the amino acid sequence of SEQ ID NO: 95, a light chain CDR2 having the amino acid sequence of SEQ ID NO: 79, and a light chain CDR3 having the amino acid sequence of SEQ ID NO: 81; or m. said antibody comprising said heavy chain CDR1 having the amino acid sequence of SEQ ID NO: 66, said heavy chain CDR2 having the amino acid sequence of SEQ ID NO: 71, and said heavy chain CDR3 having the amino acid sequence of SEQ ID NO: 77 further comprises a light chain CDR1 having the amino acid sequence of SEQ ID NO: 15, a light chain CDR2 having the amino acid sequence of SEQ ID NO: 18, and a light chain CDR3 having the amino acid sequence of SEQ ID NO: 21.

3. An isolated antibody, or an antigen-binding fragment thereof, that binds specifically to GPRC5D, and comprises a variable heavy (VH) chain region selected from the group consisting of SEQ ID NOs: 52, 53, 54, 55, 82, 83, 84, 85, 86, 87, 88, 89, or 91.

4. The antibody of embodiment 3, wherein the antibody or antigen binding fragment thereof comprises a variable light (VL) chain region selected from the group consisting of SEQ ID NOs: 56, 57, 58, 92, 93, or 94.

5. The antibody of embodiment 3, wherein the antibody or antigen binding fragment thereof comprises a VH region selected from the group consisting of SEQ ID NOs: 52, 53, 54, 55, 82, 83, 84, 85, 86, 87, 88, 89, or 91 and a VL region selected from the group consisting of SEQ ID NOs: 56, 57, 58, 92, 93, or 94.

6. The antibody of embodiment 5, wherein the VH chain region comprises SEQ ID NOs: 52, 53, or 83 paired with a VL chain region comprising SEQ ID NO: 56.

7. The antibody of embodiment 5, wherein the VH chain region comprises SEQ ID NOs: 54, 84, 85, 86, or 90 paired with a VL chain region comprising SEQ ID NO: 57.

8. The antibody of embodiment 5, wherein the VH chain region comprises SEQ ID NOs: 55 or 88 paired with a VL chain region comprising SEQ ID NO: 58.

9. The antibody of embodiment 5, wherein the VH chain region comprises SEQ ID NOs: 82 or 87 paired with a VL chain region comprising SEQ ID NO: 92.

10. The antibody of embodiment 5, wherein the VH chain region comprises SEQ ID NO: 89 paired with a VL chain region comprising SEQ ID NO: 93.

11. The antibody of embodiment 5, wherein the VH chain region comprises SEQ ID NO: 91 paired with a VL chain region comprising SEQ ID NO: 94.

12. The antibody or antigen-binding fragment of any one of embodiments 1 to 11 wherein the antibody or antigen-binding fragment thereof binds to a polypeptide having the amino acid sequence of SEQ ID NO: 22.

13. The antibody or antigen-binding fragment of any one of embodiments 1 to 12 wherein the antibody or antigen-binding fragment is a human antibody or antigen-binding fragment.

14. The antibody or antigen-binding fragment of any one of embodiments 1 to 13 wherein the antibody or antigen-binding fragment is recombinant.

15. The antigen binding fragment of any one of embodiments 1 to 14 wherein the antigen binding fragment is a Fab fragment, a Fab2 fragment, or a single chain antibody.

16. The antibody or antigen-binding fragment of any one of embodiments 1 to 15 wherein the antibody or antigen-binding fragment thereof are of IgG1, IgG2, IgG3, or IgG4 isotype.

17. The antibody or antigen-binding fragment of any of embodiments 1 to 9 is an IgG1 or an IgG4 isotype.

18. The antibody of embodiment 17 wherein the IgG1 has a K409R substitution in its Fc region.

19. The antibody of embodiment 17 wherein the IgG1 has an F405L substitution in its Fc region.

20. The antibody of embodiment 20 wherein the IgG4 has an F405L substitution and an R409K substitution in its Fc region.

21. The antibody of embodiment 16 further comprising an S228P substitution, an L234A substitution, and an L235A substitution in its Fc region.

22. The antibody or antigen-binding fragment of any one of embodiments 1 to 14 wherein the antibody or antigen-binding fragment thereof specifically binds human GPRC5D and cross reacts to cynomolgus monkey GPRC5D.

23. The antibody or antigen-binding fragment of any one of embodiment 17 wherein the antibody or antigen-binding fragment induces ADCC in vitro with an $EC_{50}$ of less than about 28 nM.

24. An isolated cell expressing the antibody or antigen-binding fragment of any one of embodiments 1 to 11.

25. The cell of embodiment 24 wherein the cell is a hybridoma.

26. The cell of embodiment 24 wherein the antibody is recombinantly produced.

27. An isolated GPRC5D x CD3 bispecific antibody comprising:
 a) a first heavy chain (HC1);
 b) a second heavy chain (HC2);
 c) a first light chain (LC1); and
 d) a second light chain (LC2), wherein the HC1 and the LC1 pair to form a first antigen-binding site that specifically binds CD3, and the HC2 and the LC2 pair to form a second antigen-binding site that specifically binds GPRC5D, or a GPRC5D x CD3-bispecific binding fragment thereof.

28. The GPRC5D x CD3 bispecific antibody or bispecific binding fragment of embodiment 27 wherein HC1 comprises SEQ ID NO: 25 and LC1 comprises SEQ ID NO: 26.

29. The GPRC5D x CD3 bispecific antibody or bispecific binding fragment of embodiment 28 wherein HC2 comprises SEQ ID NO: 52 and LC2 comprises SEQ ID NO: 56.

30. The GPRC5D x CD3 bispecific antibody or bispecific binding fragment of embodiment 28 wherein HC2 comprises SEQ ID NO: 53 and LC2 comprises SEQ ID NO: 56.

31. The GPRC5D x CD3 bispecific antibody or bispecific binding fragment of embodiment 28 wherein HC2 comprises SEQ ID NO: 54 and LC2 comprises SEQ ID NO: 57.

32. The GPRC5D x CD3 bispecific antibody or bispecific binding fragment of embodiment 28 wherein HC2 comprises SEQ ID NO: 55 and LC2 comprises SEQ ID NO: 58.

33. The GPRC5D x CD3 bispecific antibody or bispecific binding fragment of embodiment 28 wherein HC2 comprises SEQ ID NO: 82 and LC2 comprises SEQ ID NO: 92.

34. The GPRC5D x CD3 bispecific antibody or bispecific binding fragment of embodiment 28 wherein HC2 comprises SEQ ID NO: 83 and LC2 comprises SEQ ID NO: 56.

35. The GPRC5D x CD3 bispecific antibody or bispecific binding fragment of embodiment 28 wherein HC2 comprises SEQ ID NO: 84 and LC2 comprises SEQ ID NO: 57.

36. The GPRC5D x CD3 bispecific antibody or bispecific binding fragment of embodiment 28 wherein HC2 comprises SEQ ID NO: 85 and LC2 comprises SEQ ID NO: 57.

37. The GPRC5D x CD3 bispecific antibody or bispecific binding fragment of embodiment 28 wherein HC2 comprises SEQ ID NO: 86 and LC2 comprises SEQ ID NO: 57.

38. The GPRC5D x CD3 bispecific antibody or bispecific binding fragment of embodiment 28 wherein HC2 comprises SEQ ID NO: 87 and LC2 comprises SEQ ID NO: 92.
39. The GPRC5D x CD3 bispecific antibody or bispecific binding fragment of embodiment 28 wherein HC2 comprises SEQ ID NO: 88 and LC2 comprises SEQ ID NO: 58.
40. The GPRC5D x CD3 bispecific antibody or bispecific binding fragment of embodiment 28 wherein HC2 comprises SEQ ID NO: 89 and LC2 comprises SEQ ID NO: 93.
41. The GPRC5D x CD3 bispecific antibody or bispecific binding fragment of embodiment 28 wherein HC2 comprises SEQ ID NO: 91 and LC2 comprises SEQ ID NO: 94.
42. The GPRC5D x CD3 bispecific antibody or bispecific binding fragment of embodiment 28 wherein HC2 comprises SEQ ID NO: 85 and LC2 comprises SEQ ID NO: 57.
43. The GPRC5D x CD3 bispecific antibody or bispecific binding fragment of any one of embodiments 27 to 42 wherein the antibody or bispecific binding fragment are of IgG1, IgG2, IgG3, or IgG4 isotype.
44. The GPRC5D x CD3 bispecific antibody or bispecific binding fragment of embodiment 43 wherein the antibody or bispecific binding fragment is IgG4 isotype.
45. The GPRC5D x CD3 bispecific antibody or bispecific binding fragment of embodiments 27 to 42 wherein the antibody or bispecific binding fragment thereof binds GPRC5D on the surface of human myeloma cells.
46. The GPRC5D x CD3 bispecific antibody or bispecific binding fragment of embodiments 27 to 42 wherein the antibody or bispecific binding fragment thereof binds GPRC5D on the surface of human multiple myeloma cells.
47. The GPRC5D x CD3 bispecific antibody or bispecific binding fragment of embodiment 27 to 42 wherein the antibody or bispecific binding fragment induces human T cell activation in vitro with an $EC_{50}$ of less than about 0.22 nM.
48. The GPRC5D x CD3 bispecific antibody or bispecific binding fragment of embodiment 27 to 42 wherein the antibody or bispecific binding fragment induces T-cell dependent cytotoxicity of GPRC5D-expressing cells in vitro with an $EC_{50}$ of less than about 0.89 nM.
49. An isolated cell expressing the antibody or bispecific binding fragment of any one of embodiments 27 to 42.
50. The cell of embodiment 49 wherein the cell is a hybridoma.
51. The cell of embodiment 49 wherein the antibody or bispecific binding fragment is recombinantly produced.
52. A method for treating a subject having cancer, said method comprising:
    administering a therapeutically effective amount of the GPRC5D x CD3 bispecific antibody or bispecific binding fragment of any one of embodiments 27 to 42 to a patient in need thereof for a time sufficient to treat the cancer.
53. A method for inhibiting growth or proliferation of cancer cells, said method comprising:
    administering a therapeutically effective amount of the GPRC5D x CD3 bispecific antibody or bispecific binding fragment of any one of embodiments 27 to 42 to inhibit the growth or proliferation of cancer cells.
54. A method of redirecting a T cell to a GPRC5D-expressing cancer cell, said method comprising:
    administering a therapeutically effective amount of the GPRC5D x CD3 bispecific antibody or bispecific binding fragment of any one of embodiments 27 to 42 to redirect a T cell to a cancer.
55. The method of embodiment 52, 53, or 54 wherein the cancer is a hematological cancer.
56. The method of embodiment 55 wherein the hematological cancer is a GPRC5D-expressing B cell cancer.
57. The method of embodiment 56 wherein the GPRC5D-expressing B cell cancer is multiple myeloma.
58. The method of embodiment 52 comprising administering a second therapeutic agent.
59. The method of embodiment 58 wherein the second therapeutic agent is a chemotherapeutic agent or a targeted anti-cancer therapy.
60. The method of embodiment 59 wherein the chemotherapeutic agent is cytarabine, an anthracycline, histamine dihydrochloride, or interleukin 2.
61. The method of embodiment 59 wherein the second therapeutic agent is administered to said subject simultaneously with, sequentially, or separately from the bispecific antibody.
62. A pharmaceutical composition comprising the GPRC5D x CD3 bispecific antibody or bispecific binding fragment of any one of embodiments 27 to 42 and a pharmaceutically acceptable carrier.
63. A method for generating the GPRC5D x CD3 bispecific antibody or bispecific binding fragment of any one of embodiments 27 to 42 by culturing the cell of any one of embodiments 49 to 51.
64. An isolated synthetic polynucleotide encoding the HC1, the HC2, the LC1 or the LC2 of the GPRC5D x CD3 bispecific antibody or bispecific binding fragment of any one of embodiments 27 to 42.
65. A kit comprising the GPRC5D x CD3 bispecific antibody or bispecific binding fragment as defined in any one of embodiments 27 to 42 and/or a polynucleotide as defined in embodiment 63 and packaging for the same.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1: Antigens

Due to difficulties in production of recombinant GPRC5D antigens, transfected cell lines displaying GPRC5D [human (SEQ ID NO: 22), cyno (SEQ ID NO: 23), and murine (SEQ ID NO: 24)] were generated using standard methods to be used as whole cell antigens for antibody generation and characterization studies (Table 4).

TABLE 4

| GPRC5D-expressing cell lines | | | |
|---|---|---|---|
| Protein | Cell Line | Promoter | Resistance |
| Human GPRC5D | HEK293T | CMV | Neomycin |
| Cyno GPRC5D | HEK293F | CMV | Blasticidin |

Example 2: Generation of GPRCD5D Antibodies Using Phage Display

Two distinct approaches were followed in the generation of GPRC5D antibodies by phage: standard cell panning (negative selection) and FACS cell phage panning (competitive selection).

Standard Cell Phage Panning (Negative Selection):

In-house de novo phage libraries have been described in detail (Shi et al (2010) J. Mol. Biol. 397:385-396; Int. Pat. Publ. No. WO09/085462). These libraries were built on three human VH germline genes (IGHV1-69, 3-23, 5-51) and four human VL germline genes (A27, B3, L6, O12) designed to have high diversity in CDR-H3. Three de novo phage libraries (DNP00004-169HC/LC mix, DNP00005-323HC/LC mix and DNP00006-551HC/LC mix) displaying Fab variants on phage coat protein pIX were panned against GPRC5D-expressing HEK293 G5 stable cells (target cells) for round 1, 3, 5 and for rounds 2 and 4 the previous round of amplified Fab-pIX phage were applied to HEK293 background cells (the negative selection) (see Table 5). Round 1 de novo Fab-pIX phage bound to the target cells were recovered for overnight amplification. The round 1 selected phage was applied to the background cells for round 2 where the unbound Fab-pIX phage were recovered for overnight negatively selected phage amplification. Another set of positive and negative rounds of panning were performed, rounds 3 and 4. The final round was performed with the last round of negatively selected amplified phage split into two panning samples one for target cells and one for background cell panning.

TABLE 5

Standard cell phage panning flowchart-negative selection

| Panning Round | Cells used as antigen |
| --- | --- |
| 1 | Human GPRC5D HEK293 |
| 2 | HEK293 |
| 3 | Human GPRC5D HEK 293 |
| 4 | HEK293 |
| 5 [split] | Human GPRC5D HEK 293 |
|  | HEK 293 |

Standard Cell Phage Panning (Background Selection):

The Fab-pIX phage display libraries were added to HEK293 cells following similar environments and incubation times as performed with the standard cell panning procedure previously mentioned (Table 6). After three rounds the DNA corresponding to the HEK293 bound Fab-pIX phage was used to produce PCR amplicons for NGS. These NGS results would be used in an additional dynamic subtractive analysis within the NGS2.0 software to help in distinguishing possible target specific Fab candidates.

TABLE 6

Standard cell phage panning flowchart-background selection

| Panning Round | Cells used as antigen |
| --- | --- |
| 1 | HEK293 |
| 2 | HEK293 |
| 3 | HEK293 |

FACS Cell Phage Panning (Competitive Selection)

Three rounds of panning were performed by way of applying Fab-pIX phage to a mixture of target cells and background cells at the same time (Table 7). For rounds 1 and 2 the target cells with Fab-pIX phage attached were sorted by use of the GFP signal. To capture the bound Fab-pIX phage from the sorted cells an acid cell lysis was applied followed by an *E. coli* infection. The round 2 amplified Fab-pIX phage and cell mixture were sorted into two populations in the final round, gated for GFP target cells and gated for non-GFP background cells. The bound Fab-pIX phage for both cell populations was captured by acid lysis and *E. coli* infection

TABLE 7

FACS cell phage panning flowchart-competitive selection

| Panning Round | Cells used as antigen |
| --- | --- |
| 1 | Human GPRC5D_GFP HEK293 & HEK 293 |
| 2 | Human GPRC5D_GFP HEK293 & HEK 293 |
| 3 | Human GPRC5D_GFP HEK293 & HEK 293 |

Next Generation Sequencing (NGS) of Phage Panning

The overnight growth under glucose repression was done for the six of the last round panning samples. These cultures were used to make mini-prep DNA, Qiagen QIAspin DNA kit. The six DNA samples were used as PCR template to generate amplicons that measured from HCDR1 to HCDR3. The six amplicons were gel purified and pooled by keeping version 2.1, 3.0 separate for the standard cell panning and completely pooled for FACS cell panning. These pooled gel purified amplicons were provided to Genewiz NGS services to process by MiSeq 1x300 technology. Files were delivered by Genewiz and uploaded into a local server (nas2.0). Within this server the NGS2.0 software application was used to load, read, and analyze the sequence files. The top 88 sequences according to copy number (>50) and ratio of target cell (+) to background cell (−) sequences (ratio>5:1) were selected for IgG conversion. As only variable heavy chain sequence is determined by NGS, the full heavy chain constructs had to be electronically constructed into the appropriate frameworks. In addition, since only heavy chain sequence was known each of the candidates was paired with the four parental light chains (A27, B3, L6, O12). The final conversion for the candidates was done as human IgG4PAA.

ELISA Screen and Standard Sequencing

From the same DNA prep used for NGS, a restriction enzyme digest and self-ligation was done to excise the gene pIX to enable soluble Fab expression. Ninety-two colonies, picked for each of the three panning samples were assessed for Fab expression by ELISA and were sequenced to determine both heavy chain and light chain by Sanger method. The final candidates with diversified sequence within the LCDRs were cloned into mammalian expressions plasmids.

Example 4: Initial Characterization of GPRC5D Antibodies Obtained Through Phage Display Technology GPRC5D Binding:

Whole cell phage panning was completed using the human GPRC5D cells as antigen, as described above. Following NGS analysis, only heavy chain sequence was known for each of the candidates. Consequently, each heavy chain had to be paired with the 4 parental light chains (A27, B3, L6, O12), resulting in 348 mAbs from 87 Hc sequences identified using NGS. These mAbs were initially evaluated for binding to cyno GPRC5D using FACS. The cyno GPRC5D cell line was selected for initial screening to maximize the potential binding signal as the cyno GPRC5D cell line had a higher expression level than did the human GPRC5D cell line. Briefly, FACS screening was performed by normalizing protein concentration to 1 ug/ml and 100 ul of protein was mixed with 200,000 cells per well. The mAb was allowed to incubate with cells for 1 hour at 4° C. The cells were then washed three times with PBS and 0.2% FBS. An anti-human secondary mAb conjugated with PE (Jackson cat #709-116-149) was then added as the detection reagent. The cells and secondary antibody were incubated for 1 hour at 4° C. The cells were then washed three times with PBS and 0.2% FBS. The cells were washed again using PBS and 0.2% FBS and then analyzed on FACSarry.

A large number of the hits were observed to bind to cyno GPRC5D, including 15 mAbs with MFI greater than 100,000, 23 mAbs with MFI less than 100,000 but greater than 10,000 and 63 mAbs with MFI less than 10,000 but greater than 1000. (Table 8).

TABLE 8

FACS binding data for NGS derived mAbs to cyno GPRC5D. Heavy chain sequences identified from NGS analysis were paired with each parental Lc as shown. GC5M29 was used as the control (PH9L3 light chain). mAbs highlighted have an MFI > 1000

| Hc ID | GPRC5D mAb [PH9L1 (A27)] | MFI | GPRC5D mAb [PH9L2 (B3)] | MFI | GPRC5D mAb [PH9L3 (L6)] | MFI | GPRC5D mAb [PH9L4 (O12)] | MFI |
|---|---|---|---|---|---|---|---|---|
| GC5H18 | GC5B22 | 198 | GC5B23 | 230 | GC5B24 | 246 | GC5B25 | 31324 |
| GC5H17 | GC5B66 | 242 | GC5B67 | 272 | GC5B68 | 2682 | GC5B69 | 17416 |
| GC5H20 | GC5B114 | 199 | GC5B115 | 266 | GC5B116 | 253 | GC5B117 | 5037 |
| GC5H15 | GC5B158 | 14407 | GC5B159 | 139766 | GC5B160 | 84111 | GC5B161 | 7856 |
| GC5H13 | GC5B202 | 89948 | GC5B203 | 9173 | GC5B204 | 15203 | GC5MB205 | 52663 |
| GC5H23 | GC5B242 | 242 | GC5B243 | 116641 | GC5B244 | 249 | GC5B245 | 469 |
| GC5H14 | GC5B282 | 487 | GC5B283 | 341 | GC5B284 | 249 | GC5B285 | 87116 |
| GC5H22 | GC5B326 | 195 | GC5B237 | 265 | GC5B328 | 248 | GC5B329 | 292 |
| GC5H24 | GC5B26 | 194 | GC5B27 | 265 | GC5B28 | 229 | GC5B29 | 590 |
| GC5H19 | GC5B70 | 214 | GC5B71 | 229 | GC5B72 | 2013 | GC5B73 | 3827 |
| GC5H33 | GC5B118 | 178 | GC5B119 | 222 | GC5B120 | 880 | GC5B121 | 43924 |
| GC5H36 | GC5B162 | 86773 | GC5B163 | 21970 | GC5B164 | 122043 | GC5B165 | 1870 |
| GC5H31 | GC5B206 | 467 | GC5B207 | 3636 | GC5B208 | 481 | GC5B209 | 1409 |
| GC5H29 | GC5B246 | 202 | GC5B247 | 3037 | GC5B248 | 2835 | GC5B249 | 1373 |
| GC5H34 | GC5B286 | 239 | GC5B287 | 163990 | GC5B288 | 259 | GC5B289 | 271 |
| GC5H35 | GC5B330 | 202 | GC5B331 | 552 | GC5B332 | 191978 | GC5B333 | 1591 |
| GC5H26 | GC5B30 | 204 | GC5B31 | 230 | GC5B32 | 16553 | GC5B33 | 270 |
| GC5H27 | GC5B74 | 238 | GC5B75 | 365 | GC5B76 | 829 | GC5B77 | 317 |
| GC5H25 | GC5B122 | 153 | GC5B123 | 237 | GC5B124 | 6026 | GC5B125 | 6197 |
| GC5H30 | GC5B166 | 1510 | GC5B167 | 6266 | GC5B168 | 32482 | GC5B169 | 327 |
| GC5H47 | GC5B210 | 1730 | GC5B211 | 284 | GC5B212 | 278 | GC5B213 | 727 |
| GC5H42 | GC5B250 | 3969 | GC5B251 | 213233 | GC5B252 | 63295 | GC5B253 | 574 |
| GC5H37 | GC5B290 | 8839 | GC5B291 | 201024 | GC5B292 | 110940 | GC5B293 | 305 |
| GC5H45 | GC5B334 | 160 | GC5B335 | 1434 | GC5B336 | 3228 | GC5B337 | 309 |
| GC5H38 | GC5B34 | 157 | GC5B35 | 283 | GC5B36 | 14936 | GC5B37 | 297 |
| GC5H40 | GC5B78 | 162 | GC5B79 | 309 | GC5B80 | 428 | GC5B81 | 74140 |
| GC5H43 | GC5B126 | 157 | GC5B127 | 265 | GC5B128 | 268 | GC5B129 | 1283 |
| GC5H49 | GC5B170 | 1014 | GC5B171 | 51995 | GC5B172 | 1434 | GC5B173 | 332 |
| GC5H62 | GC5B214 | 2565 | GC5B215 | 274 | GC5B216 | 263 | GC5B217 | 1589 |
| GC5H60 | GC5B254 | 161 | GC5B255 | 5788 | GC5B256 | 460 | GC5B257 | 308 |
| GC5H94 | GC5B294 | 190 | GC5B295 | 2312 | GC5B296 | 745 | GC5B298 | 261 |
| GC5H69 | GC5B338 | 188 | GC5B339 | 260 | GC5B340 | 1798 | GC5B341 | 290 |
| GC5H85 | GC5B38 | 10809 | GC5B39 | 1112 | GC5B40 | 110654 | GC5B41 | 4379 |
| GC5H96 | GC5B82 | 165 | GC5B83 | 272 | GC5B84 | 1547 | GC5B85 | 3563 |
| GC5H97 | GC5B130 | 174 | GC5B131 | 293 | GC5B132 | 306 | GC5B133 | 343 |
| GC5H76 | GC5B174 | 219 | GC5B175 | 3631 | GC5B176 | 244 | GC5B177 | 324 |
| GC5H68 | GC5B218 | 21420 | GC5B219 | 310 | GC5B220 | 777 | GC5B221 | 762 |
| GC5H79 | GC5B256 | 714 | GC5B257 | 1146 | GC5B258 | 456 | GC5B259 | 1129 |
| GC5H71 | GC5B298 | 185 | GC5B299 | 1370 | GC5B300 | 260 | GC5B301 | 292 |
| GC5H93 | GC5B342 | 164 | GC5B343 | 247 | GC5B344 | 401 | GC5B345 | 283 |
| GC5H21 | GC5B42 | 219 | GC5B43 | 307 | GC5B44 | 2694 | GC5B45 | 1022 |
| GC5H39 | GC5B86 | 192 | GC5B87 | 344 | GC5B88 | 470 | GC5B89 | 41027 |
| GC5H50 | GC5B134 | 764 | GC5B135 | 340 | GC5B136 | 600 | GC5B137 | 2087 |
| GC5H28 | GC5B178 | 750 | GC5B179 | 6708 | GC5B180 | 1005 | GC5B181 | 535 |
| GC5H53 | GC5B222 | 284 | GC5B223 | 264 | GC5B224 | 228 | GC5B225 | 605 |
| GC5H51 | GC5B262 | 159 | GC5B263 | 1013 | GC5B267 | 238 | GC5B268 | 309 |
| GC5H64 | GC5B302 | 184 | GC5B303 | 329 | GC5B304 | 240 | GC5B305 | 1571 |
| GC5H16 | GC5B346 | 182 | GC5B347 | 259 | GC5B348 | 332 | GC5B349 | 552 |
| GC5H65 | GC5B46 | 204 | GC5B47 | 327 | GC5B48 | 1320 | GC5B49 | 392 |
| GC5H32 | GC5B90 | 335 | GC5B91 | 340 | GC5B92 | 1848 | GC5B93 | 1780 |
| GC5H54 | GC5B138 | 193 | GC5B139 | 354 | GC5B140 | 323 | GC5B141 | 292 |
| GC5H99 | GC5B182 | 196 | GC5B183 | 6421 | GC5B184 | 309 | GC5B185 | 280 |
| GC5H52 | GC5B226 | 204 | GC5B227 | 298 | GC5B228 | 247 | GC5B229 | 263 |
| GC5H48 | GC5B266 | 268 | GC5B267 | 2160 | GC5B268 | 235 | GC5B269 | 281 |
| GC5H44 | GC5B306 | 204 | GC5B307 | 313 | GC5B308 | 302 | GC5B309 | 621 |
| GC5H46 | GC5B350 | 198 | GC5B351 | 287 | GC5B352 | 4300 | GC5B353 | 1708 |
| GC5H56 | GC5B50 | 229 | GC5B51 | 36679 | GC5B52 | 386 | GC5B53 | 446 |
| GC5H55 | GC5B94 | 255 | GC5B95 | 609 | GC5B96 | 411 | GC5B97 | 350 |
| GC5H98 | GC5B142 | 194 | GC5B143 | 407 | GC5B144 | 284 | GC5B145 | 483 |

TABLE 8-continued

FACS binding data for NGS derived mAbs to cyno GPRC5D. Heavy chain sequences
identified from NGS analysis were paired with each parental Lc as shown. GC5M29 was used as
the control (PH9L3 light chain). mAbs highlighted have an MFI > 1000

| Hc ID | GPRC5D mAb [PH9L1 (A27)] | MFI | GPRC5D mAb [PH9L2 (B3)] | MFI | GPRC5D mAb [PH9L3 (L6)] | MFI | GPRC5D mAb [PH9L4 (O12)] | MFI |
|---|---|---|---|---|---|---|---|---|
| GC5H61 | GC5B186 | 543 | GC5B187 | 1132 | GC5B188 | 376 | GC5B189 | 333 |
| GC5H92 | GC5B320 | 297 | GC5B321 | 294 | GC5B322 | 280 | GC5B323 | 386 |
| GC5H5 | GC5B17 | 243 | GC5B18 | 301 | GC5B19 | 1048 | GC5B20 | 384 |
| GC5H59 | GC5B98 | 272 | GC5B99 | 388 | GC5B100 | 661 | GC5B101 | 528 |
| GC5H66 | GC5B354 | 223 | GC5B355 | 852 | GC5B356 | 374 | GC5B357 | 500 |
| GC5H80 | GC5B54 | 299 | GC5B55 | 415 | GC5B56 | 422 | GC5B57 | 487 |
| GC5H87 | GC5B102 | 383 | GC5B103 | 460 | GC5B104 | 3130 | GC5B105 | 456 |
| GC5H67 | GC5B146 | 325 | GC5B147 | 370 | GC5B148 | 383 | GC5B149 | 487 |
| GC5H73 | GC5B190 | 236 | GC5B191 | 2556 | GC5B192 | 409 | GC5B193 | 387 |
| GC5H86 | GC5B230 | 17885 | GC5B231 | 543 | GC5B232 | 494 | GC5B233 | 620 |
| GC5H70 | GC5B270 | 390 | GC5B271 | 660 | GC5B272 | 389 | GC5B273 | 450 |
| GC5H90 | GC5B314 | 219 | GC5B315 | 334 | GC5B316 | 363 | GC5B317 | 403 |
| GC5H95 | GC5B358 | 211 | GC5B359 | 344 | GC5B360 | 414 | GC5B361 | 449 |
| GC5H74 | GC5B58 | 294 | GC5B59 | 448 | GC5B60 | 477 | GC5B61 | 548 |
| GC5H78 | GC5B106 | 267 | GC5B107 | 440 | GC5B108 | 474 | GC5B109 | 497 |
| GC5H77 | GC5B150 | 312 | GC5B151 | 452 | GC5B152 | 412 | GC5B153 | 709 |
| GC5H91 | GC5B194 | 296 | GC5B195 | 448 | GC5B196 | 491 | GC5B197 | 483 |
| GC5H57 | GC5B234 | 128355 | GC5B235 | 195348 | GC5B236 | 134008 | GC5B237 | 11255 |
| GC5H41 | GC5B274 | 313 | GC5B275 | 7431 | GC5B278 | 435 | GC5B279 | 542 |
| GC5H58 | GC5B318 | 2608 | GC5B319 | 5791 | GC5B320 | 49616 | GC5B321 | 4823 |
| GC5H63 | GC5B362 | 313 | GC5B363 | 392 | GC5B364 | 461 | GC5B365 | 3613 |
| GC5H72 | GC5B62 | 326 | GC5B63 | 463 | GC5B64 | 485 | GC5B65 | 694 |
| GC5H75 | GC5B110 | 208487 | GC5B111 | 692 | GC5B112 | 140269 | GC5B113 | 104136 |
| GC5H81 | GC5B154 | 351 | GC5B155 | 412 | GC5B156 | 440 | GC5B157 | 555 |
| GC5H82 | GC5B198 | 285 | GC5B199 | 593 | GC5B200 | 499 | GC5B201 | 485 |
| GC5H83 | GC5B238 | 3698 | GC5B239 | 4370 | GC5B240 | 4676 | GC5B241 | 825 |
| GC5H88 | GC5B278 | 3659 | GC5B279 | 481 | GC5B280 | 425 | GC5B281 | 633 |
| GC5H89 | GC5B332 | 299 | GC5B333 | 561 | GC5B334 | 4467 | GC5B335 | 494 |
| GC5H84 | GC5B366 | 544 | GC5B367 | 474 | GC5B368 | 6313 | GC5B369 | 26116 |

The 40 mAbs with the highest binding affinity were selected for additional characterization, which consisted of repeating the binding study to cyno GPCR5D cells, as well as, assessment of binding to human GPRC5D expressing cells using FACS (Table 9). These data were analyzed to select 17 mAbs for purification and GPRC5D x CD3 bispecific antibody generation (highlighted). Factors used to select mAbs for purification and GPRC5D x CD3 bispecific antibody generation include specificity of binding to human GPRC5D, cross-reactivity to cyno GPRC5D and diversity in Hc sequence. For example, GC5H36 was paired with three distinct light chains and analyzed for binding (GC5B162, GC5B163, GC5B164). Only GC5B164 was advanced as this mAb was observed to have the higher MFI to human GPRC5D than GC5B162 or GC5B163.

TABLE 9

FACS binding data for NGS derived mAbs to cyno and
human GPRC5D expressing HEK293F cells. Non-transfected
HEK293F cells were used to evaluate binding specificity
for GPRC5D. TF7M1636 was used as the isotype control.
mAbs highlighted were selected for further analysis.

| Protein ID | HC Peptide ID | cyno GPRC5D MFI | human GPRC5D MFI | 293F MFI |
|---|---|---|---|---|
| GC5B38 | GC5H85 | 6,864 | 280 | 215 |
| GC5B110 | GC5H75 | 142,277 | 2,543 | 235 |
| GC5B158 | GC5H15 | 4,923 | 285 | 235 |
| GC5B162 | GC5H36 | 75,139 | 2,981 | 230 |
| GC5B202 | GC5H13 | 30,470 | 2,152 | 256 |
| GC5B218 | GC5H68 | 10,451 | 277 | 263 |
| GC5B230 | GC5H86 | 19,103 | 364 | 290 |
| GC5B234 | GC5H57 | 134,258 | 1,657 | 261 |
| GC5B51 | GC5H56 | 22,661 | 667 | 480 |
| GC5B159 | GC5H15 | 129,370 | 1,987 | 258 |
| GC5B163 | GC5H36 | 7,605 | 840 | 310 |
| GC5B171 | GC5H49 | 24,133 | 1,144 | 1,321 |
| GC5B235 | GC5H57 | 158,011 | 2,643 | 254 |
| GC5B243 | GC5H23 | 67,848 | 20,458 | 221 |
| GC5B251 | GC5H42 | 74,510 | 11,418 | 235 |
| GC5B281 | GC5H34 | 109,418 | 5,317 | 570 |
| GC5B291 | GC5H37 | 77,798 | 10,427 | 880 |
| GC5B32 | GC5H26 | 3,597 | 14,656 | 358 |
| GC5B36 | GC5H38 | 5,353 | 2,002 | 352 |
| GC5B40 | GC5H85 | 67,279 | 4,510 | 310 |
| GC5B112 | GC5H75 | 104,875 | 470 | 433 |
| GC5B160 | GC5H15 | 40,881 | 635 | 276 |
| GC5B164 | GC5H36 | 78,672 | 12,664 | 343 |
| GC5B168 | GC5H30 | 41,779 | 28,885 | 1,238 |
| GC5B204 | GC5H13 | 5,090 | 390 | 212 |
| GC5B236 | GC5H57 | 78,546 | 1,442 | 192 |
| GC5B252 | GC5H42 | 22,010 | 1,498 | 204 |
| GC5B292 | GC5H37 | 63,366 | 1,872 | 480 |
| GC5B320 | GC5H58 | 63,345 | 22,891 | 231 |
| GC5B332 | GC5H35 | 106,515 | 13,348 | 253 |
| GC5B25 | GC5H18 | 22,079 | 705 | 431 |
| GC5B69 | GC5H17 | 1,593 | 851 | 284 |
| GC5B81 | GC5H40 | 62,756 | 9,986 | 288 |
| GC5B89 | GC5H39 | 31,613 | 1,068 | 251 |
| GC5B113 | GC5H75 | 66,475 | 550 | 323 |
| GC5B121 | GC5H33 | 35,493 | 3,061 | 299 |
| GC5B205 | GC5H13 | 63,610 | 25,199 | 260 |
| GC5B237 | GC5H57 | 2,579 | 267 | 248 |
| GC5B285 | GC5H14 | 81,405 | 19,870 | 225 |

TABLE 9-continued

FACS binding data for NGS derived mAbs to cyno and human GPRC5D expressing HEK293F cells. Non-transfected HEK293F cells were used to evaluate binding specificity for GPRC5D. TF7M1636 was used as the isotype control. mAbs highlighted were selected for further analysis.

| Protein ID | HC Peptide ID | cyno GPRC5D MFI | human GPRC5D MFI | 293F MFI |
|---|---|---|---|---|
| GC5B369 | GC5H84 | 16,241 | 559 | 252 |
|  | TF7M1636 | 956 | 2,621 | 1,538 |
|  | human 2nd | 209 | 316 | 228 |
|  | anti hGPRC5D | 9,001 | 379 | 70 |
|  | mouse anti | 60 | 82 | 65 |
|  | isotype unstained | 44 | 50 | 33 |

The concentration dependent binding profile of each of the selected mAbs against human GPRC5D expressing HEK293 cells and non-transfected HEK293 cells was determined using FACS (FIG. 1). All mAbs were observed to bind to human GPRC5D in a dose dependent manner. Three mAbs, GC5B36, GC5B168, and GC5B205 were also observed to bind to the non-transfected (GPRC5D null) HEK293 cells and were deprioritized due to this non-specific interaction with the cells.

The remaining 14 mAbs were selected for bispecific antibody generation with an anti-CD3 arm CD3B219 and anti-RSV null arm B23M46 (Table 10).

TABLE 10

The relationship between GPRC5D mAb IDs and bispecific IDs.

| GPRC5D mAb Protein ID | x CD3 bispecific ID | x B23Null bispecific ID |
|---|---|---|
| GC5B320 | GCDB44 | GCDB30 |
| GC5B243 | GCDB40 | GCDB26 |
| GC5B285 | GCDB43 | GCDB29 |
| GC5B332 | GCDB45 | GCDB31 |
| GC5B164 | GCDB35 | GCDB21 |
| GC5B251 | GCDB41 | GCDB27 |
| GC5B81 | GCDB32 | GCDB18 |
| GC5B235 | GCDB38 | GCDB24 |
| GC5B110 | GCDB34 | GCDB20 |
| GC5B202 | GCDB36 | GCDB22 |
| GC5B234 | GCDB37 | GCDB23 |
| GC5B252 | GCDB42 | GCDB28 |
| GC5B236 | GCDB39 | GCDB25 |
| GC5B89 | GCDB33 | GCDB19 |

Figure 2:
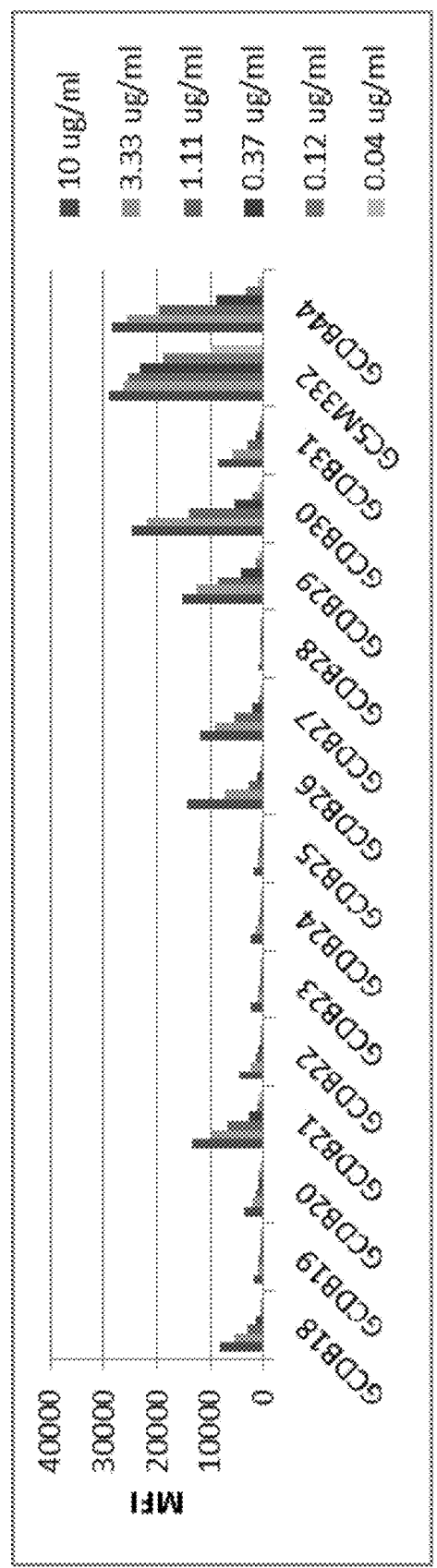
FIG. 2. Dose dependent binding of anti-GPCRSD x CD3 bispecific antibodies to human GPRC5D HEK293F cells.

One bispecific antibody, GCDB38, precipitated during recombination and another, GCDB36, contained >10% aggregate. All other bispecific antibodies passed the standard release criteria and the null arm bispecific antibodies were analyzed for concentration dependent binding to human GPRC5D expressing HEK293 cells (FIG. 2).

All bispecific antibodies were observed to bind in a dose dependent manner. GC5B320 was included as a binding comparator to understand binding differences between bivalent mAbs and monovalent bispecific antibodies. GCDB44 was included as a binding comparator to understand binding differences between anti-CD3 bispecific antibodies and anti-RSV null arm mAbs. The expected decrease in apparent binding affinity was observed when comparing the mAb GC5B320 to bispecific antibodies GCDB30 and GCDB44. In addition, the GCDB44 (anti-CD3 bispecific Ab) was observed to have slightly higher binding affinity to the anti-human GPRC5D cells compared with the GCDB30 (anti-RSV null arm bispecific Ab), demonstrating that the anti-CD3 arm is positively impacted binding to this cell line.

Figure 3:
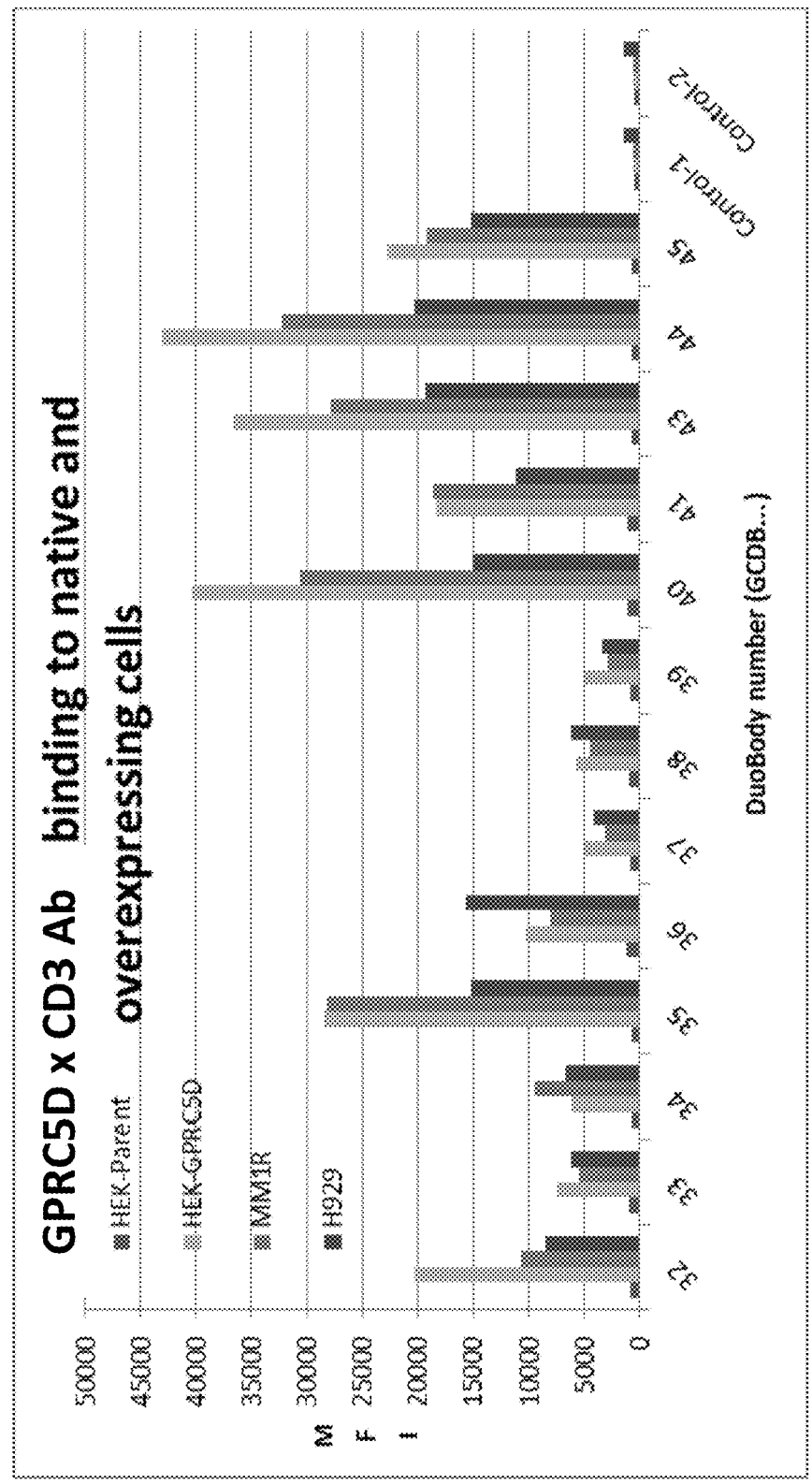
FIG. 3. The binding profile of the bispecific antibodies on MM1R and H929 cells was compared with the overexpressed human GPCR5D HEK293 cells and non-transfected HEK293 cells using FACS.

The panel of bispecific antibodies was also profiled for binding against MM1R and H929 cells, which endogenously express GPRC5D (FIG. 3). The binding profile of the bispecific antibodies on MM1R and H929 cells was compared with the overexpressed human GPCRSD HEK293 cells and non-transfected HEK293 cells using FACS. The bispecific antibodies were observed to bind to GPRC5D as expressed endogenously on MM1R and H929 cells with a range of affinity. The highest binding was observed to the human GPRC5D HEK cells, which as an overexpressed stable cell line, has a much higher receptor density than either MM1R or H929 cells. GCDB37, GCDB38, GCDB39 and GCDB41 were not advanced due to the low binding affinity observed for H929 and MM1R cells.

In vitro T-Cell Dependent Cytotoxicity

Figure 4A:
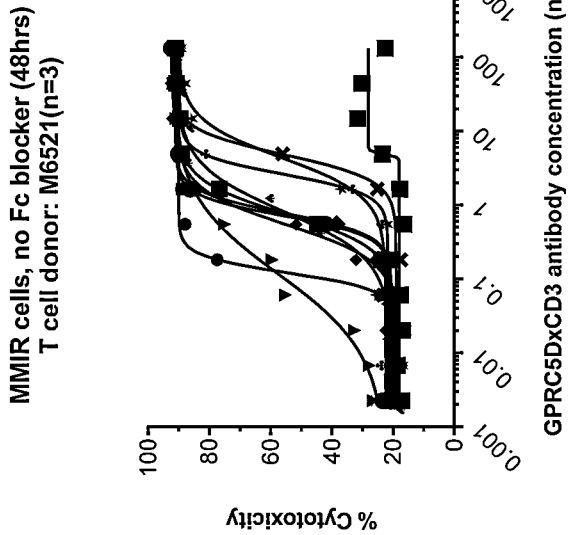
FIGS. 4A and 4B. T-cell mediated cytotoxicity and T cell activation of anti-GPCR5D x CD3 antibodies against human GPRC5D-expressing cells.
Figure 4B:
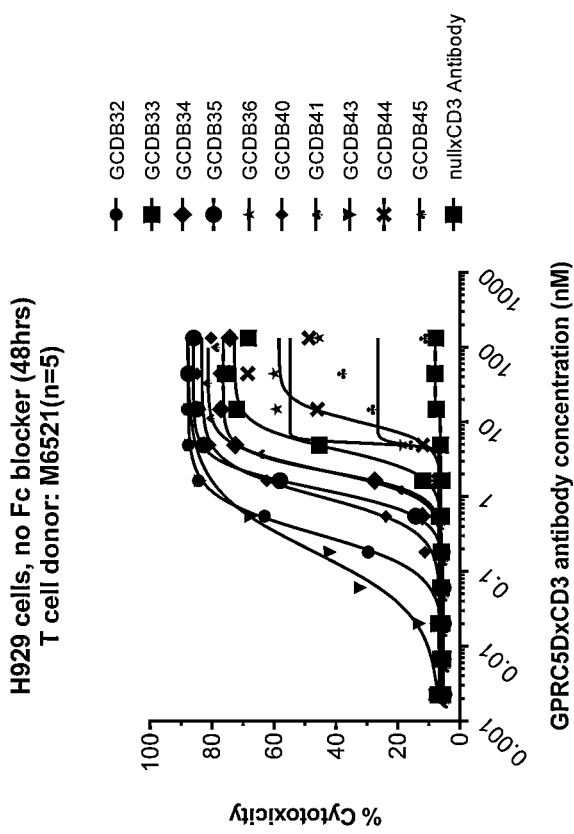

The panel of bispecific antibodies were then profiled for potency in a T-cell mediated cytotoxicity assay using H929 and MM1R target cells (FIGS. 4A and B, Table 11). Briefly, target cells (H929, MM1.R, OPM2, LP-1 and Daudi or HEK parent and HEK+GPRC5D cells) were counted and 10 million cells were centrifuged at 1350 rpm for 3 minutes and cell pellets were resuspended in 1 ml of diluted CFSE solution (CellTrace CFSE proliferation stain was reconstituted in 18 µl of sterile DMSO and 1 µl of the solution was diluted in 10 ml of sterile PBS) and incubated at room temperature for 8 minutes in dark. After the incubation, 1 ml of HI FBS was added to cell suspension to quench the surplus CFSE. Cells were washed twice in RPMI-1640 with 10% FBS. After reconstitution in 10 ml of RPMI, cells were counted and cell viability was recoded in a spreadsheet. Cells were diluted to $2.2 \times 10^5$/ml and incubated at 37° C. until use.

Pan T cells from normal donors were thawed in 37° C. water bath, and cells were then centrifuged at 1350 rpm at 4° C. for 3 minutes. The supernatants were discarded and reconstituted in culture medium at $1.1 \times 10^6$/ml concentration. $2 \times 10^5$ target cells were added to wells of a 96-well U-bottom plate, followed by Fc blocker (to final concentration of 2 mg/ml). All cell lines were incubated at room temperature for 10 minutes to block Fc receptor activity. $1 \times 10^5$ T cells were added to the wells (5:1 Effector:Target ratio). After target and T cells were mixed, 20 µl of GPRC5D x CD3 bispecific Ab dilutions were added to each well. GPRC5D x CD3 bispecific antibodies were diluted to 800 µg/ml (10X) in PBS. The titration was prepared in 4-fold serial dilutions in PBS in a 96-well U-bottom plate. The last column was left as PBS alone (vehicle control). The plates were incubated at 37° C. with 5% $CO_2$ for 48 hours.

Two days later (48 hours), the plates were centrifuged and 100 µl of supernatants were stored at −80° C. for cytokine release assay. Cells were washed in 200 µl of PBS and incubated in 50 µl of near-IR Live/Dead stain (1:200 dilution) and anti-CD25 PE antibody (1:50 dilution) for 20 minutes at room temperature. Then, the cells were washed once in 200 µl of FACS buffer and finally reconstituted in 150 µl of FACS buffer. Cells were analyzed using FACSCanto II and FlowJo 7.6 for target cytotoxicity (% target) and T cell activation CD25+(% live T cells). Graphing and fitting of data were done in GraphPad Prism 6 using nonlinear regression with variable slope (four parameters) function using least squares method.

TABLE 11

Average EC$_{50}$ calculated from T-cell mediated cytotoxicity assessment of GPRC5D × CD3 bispecific antibodies using H929 and MM1R target cells.
GPRC5D × CD3 EC50 (nM)

| Bispecific ID | H929 (n = 5) | MM1R (n = 3) | Ranking (Average) H929/MM1R |
|---|---|---|---|
| GCDB32 | 0.39 ± 0.3 | 0.12 ± 0.1 | 2/1 |
| GCDB33 | 4.29 ± 1.28 | 0.8 ± 0.18 | 7/6 |
| GCDB34 | 2.13 ± 0.93 | 0.77 ± 0.24 | 5/5 |
| GCDB35 | 1.39 ± 0.84 | 0.74 ± 0.32 | 4/4 |
| GCDB36 | 5.2 ± 0.93 | 4.22 ± 0.55 | 8/9 |
| GCDB40 | 1.2 ± 0.92 | 0.52 ± 0.38 | 3/3 |
| GCDB41 | NA | 2.58 ± 0.15 | 10/8 |
| GCDB43 | 0.36 ± 0.41 | 0.21 ± 0.29 | 1/2 |
| GCDB44 | 10.29 ± 2.65 | 4.41 ± 0.29 | 9/10 |
| GCDB45 | 2.25 ± 1 | 0.91 ± 0.93 | 6/7 |

All bispecific antibodies are active in T-cell mediated H929 cell killing, with a range of potencies observed (Table 11). Similar rank order was observed for both cell lines. However a lower EC$_{50}$ was observed in MM1R cells. Interestingly, binding affinity was not necessarily correlative of potency in T-cell mediated cytotoxicity assay. For example, GCDB44 was the highest affinity binding bispecific antibody but the least potent in the cytotoxicity assay. While GCDB43, with similar, albeit slightly lower, binding affinity was the most potent in the cytotoxicity assay.

Figures 5A, 5B:
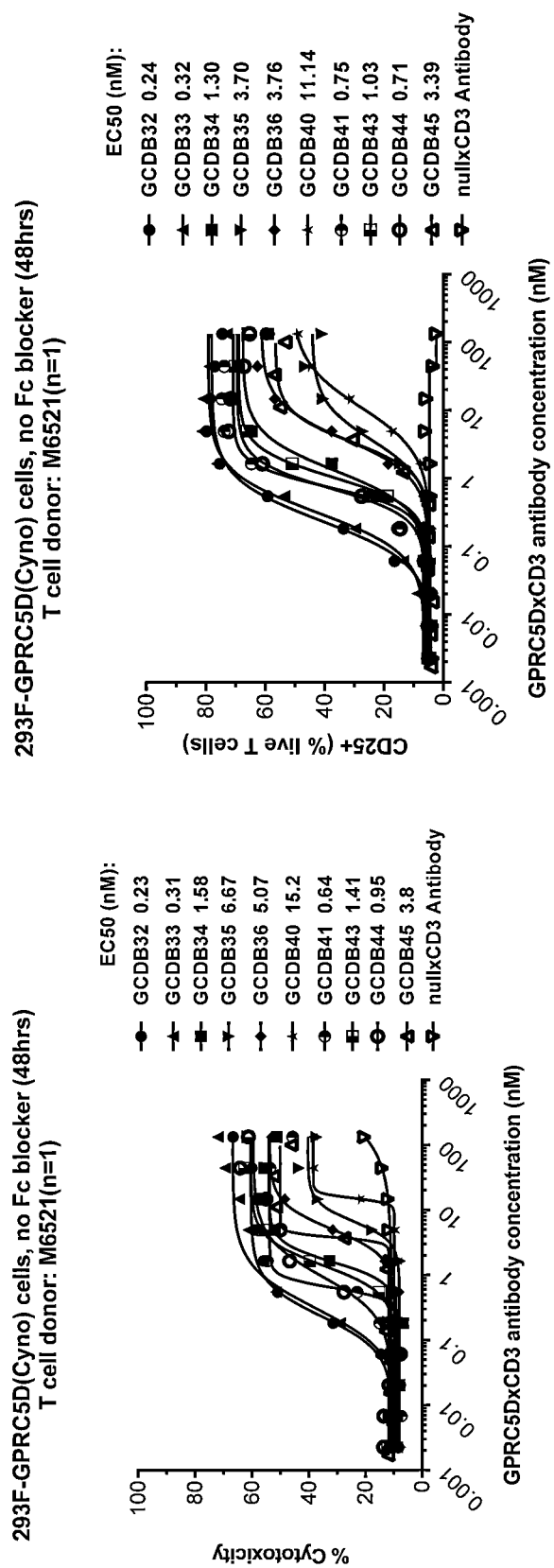
FIGS. 5A and 5B T-cell mediated cytotoxicity and T cell activation of anti-GPCR5D x CD3 antibodies against cyno GPRC5D-expressing cells.

To assess the functional cross-reactivity with cyno GPRC5D, the panel of bispecific antibodies was then profiled for T-cell mediated cytotoxicity and T cell activation using cyno GPRC5D HEK293 cells (FIGS. 5A and B). All bispecific antibodies were active in this assay though a range of potency was observed against the cyno GPRC5D+expressing cells.

In Vivo Efficacy

Figure 6A:
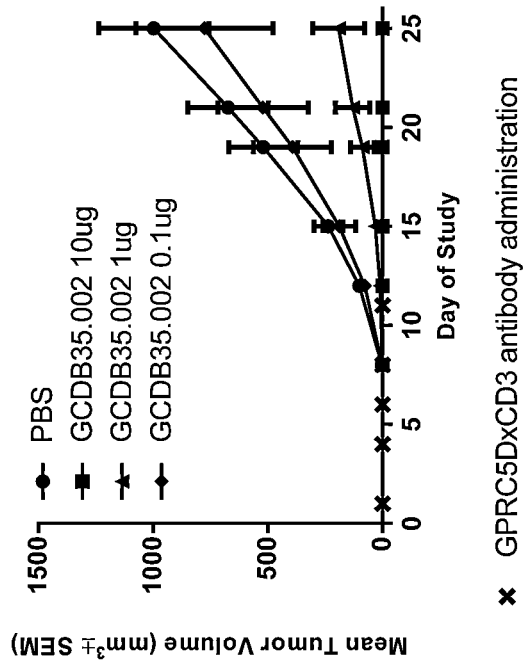
FIGS. 6A and 6B. GPRC5DxCD3 Abs efficiently kill H929 cells in prophylactic NSG mice model. GCDB32 (6A) and GCDB35 (6B) resulted in complete tumor growth inhibition at the 10 ug doses, with GCDB32 also capable of 100% tumor growth inhibition at the 1 ug dose.
Figure 6B:
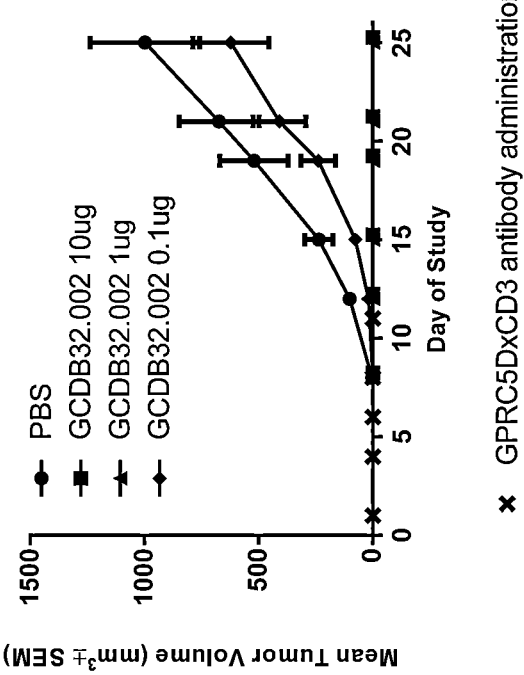

A benchmarking in vivo study was then completed to understand the in vivo potency of these GPRC5D X CD3 bispecific antibodies. GCDB32 and GCDB35 (FIGS. 5A & B) were selected to test in a H929 prophylactic tumor model. H929 cells were implanted into NSG mice, one week following injection of human PBMCs. Treatment of the bispecific antibodies was initiated at the same time that the H929 cells were implanted and continued every 2 or 3 days (q2d or q3d) at 10 ug, 1 ug, and 0.1 ug/animal doses for a total of five treatments. Ten mice were used in each group and PBS included as the vehicle control. Treatment was stopped at day 11 and the study was terminated on day 25 (FIGS. 6A and B) or day 26 (FIG. 12A-D). All the GPRC5D x CD3 antibodies tested in this prophylactic model showed 100% tumor growth inhibition at the 10 and 1 ug/animal dose except for GCDB35 which showed round 80% tumor growth inhibition at 1 ug/animal dose. At tenfold lower dose (0.1 ug/animal) these bispecific antibodies showed varying degree of efficacy ranging from 10 to 80% tumor growth inhibition.

In Vitro T-Cell Dependent Cytotoxicity in Presence of Fc Blocker

Figure 7A:
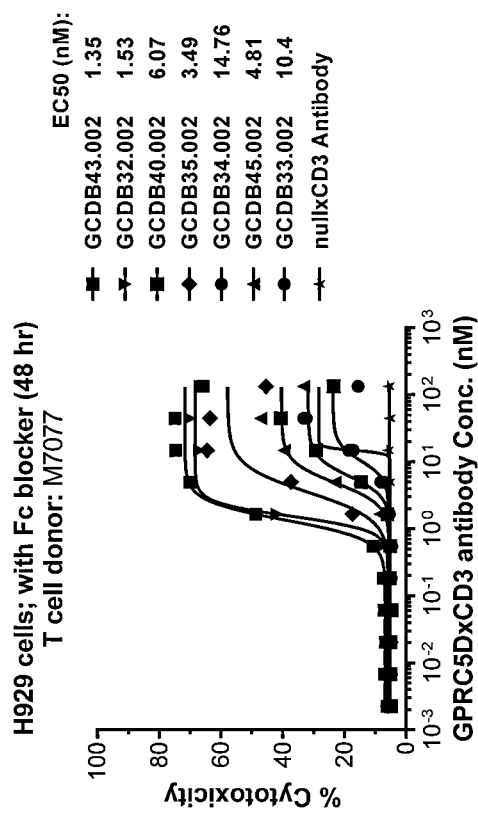
FIGS. 7A and 7B. Comparison of potency in the absence (7A) and presence (7B) of Fc block.
Figure 7B:
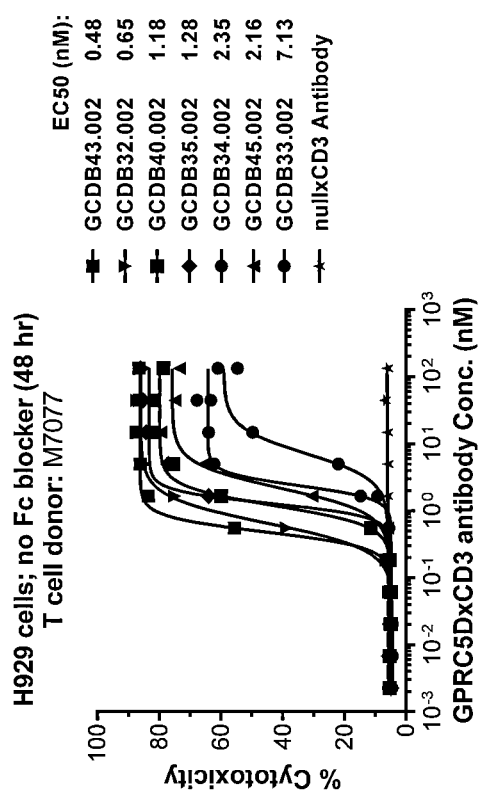

To gain an understanding of the specificity of the GPRC5D targeting arm, the panel of GPRC5D x CD3 bispecific antibodies was then assessed in a T-cell redirection cytotoxicity assay in the presence of Fc block. This experiment was critical to understanding specificity as the target cells for bispecific antibodies are B-cells expressing Fcγ receptors capability of interacting with the Fc portion of the bispecific antibody in the in vitro assay. A shift in potency was observed in the T-cell mediated cytotoxicity assay for a number of the bispecific antibodies, with the greatest shift observed for GCDB40 and GCDB34 (FIG. 7A-7B).

Direct measurement of binding interactions between the four most potent bispecific antibodies (GCDB32, GCDB35, GCDB40, and GCDB43) and Fcγ receptors was then completed (FIG. 8A-8D). One round of Alpha Screen analysis was carried out for each of the Fcγ receptors and bispecific antibodies listed above. All samples were assayed in duplicate. On FcγRI, the four bispecific antibodies behave like B21M hIgG4 PAA. That is, they are no more competitive than matched isotype control. Similar differences were also observed between the hIgG1 WT control and the four bispecific antibodies on FcγRIIIa, with GCD43 most like the IgG4PAA isotype control and the other bispecific antibodies having slightly higher affinity for FcγRIIIa. On both FcγRIIa and FcγRIIb, the four bispecific antibodies compete in the following order: GCDB40>GCDB32>GCDB43>GCDB35. GCDB40 is the most competitive or binds with highest affinity to FcγRIIa and FcγRIIb. In fact GCDB40 competes on FcγRIIa and FcγRIIb to the same extent as hIgG1 WT, corroborating the observed shift in potency observed in the T-cell mediated cytotoxicity assay when Fc block was included. Due to the unexpected interactions with FcγRIIa and FcγRIIb, GCDB40 was not advanced.

Competition Binning Assay

Anti-GPRC5D mAbs were assessed for competition binding with each other to the human GPCR5D cells. Briefly, cells were plated at 50,000 cells/well in 50 uL of media and allowed to settle for 90 minutes at 37° C. Wells were then blocked using 3% BSA for 1 hour at room temperature. mAbs were labeled with ruthenium (II) tris-bipyridine, N-hydroxysuccinimide (Ru-label) following standard procedures. In a separate 96 well plate, 5 uM of competitor mAb was incubated with 50 nM of Ru-labeled mAb. The blocking solution was removed from the cell plate and 25 uL of mAb solution added. Plates were incubated for 1 hour at room temperature with shaking. After washing the plates thrice with PBS, 150 uL of MSD read buffer (without surfactant) was added and the binding of the Ru-labeled antibody detected using a MSD plate reader.

All mAbs belong to the same competition group, with only GC5B420 and GC5B421 not fully competed by GC5B81, GC5B285, and/or GC5B332 (Blocked<70%) (Table 12). It is hypothesized that simultaneous binding of two mAbs to GPRC5D may be sterically impossible given the small size of the extracellular domain of GPRC5D compared to the size of a mAb.

TABLE 12

Competition binding epitope binning of anti-GPRC5D mAbs. Anti-GPRC5D mAbs were assessed for competition binding with each other to the human GPCR5D cells (+/− = Blocked < 70%).

| mAb ID | GC5B81 | GC5B164 | GC5B285 | GC5B332 | GC5B420 | GC5B421 |
|---|---|---|---|---|---|---|
| GC5B81 | + | + | + | + | +/− | +/− |
| GC5B164 | + | + | + | + | + | + |

TABLE 12-continued

Competition binding epitope binning of anti-GPRC5D mAbs. Anti-GPRC5D mAbs were assessed for competition binding with each other to the human GPCR5D cells (+/− = Blocked < 70%).

| mAb ID | GC5B81 | GC5B164 | GC5B285 | GC5B332 | GC5B420 | GC5B421 |
|---|---|---|---|---|---|---|
| GC5B285 | + | + | + | + | + | +/− |
| GC5B332 | + | + | + | + | +/− | + |
| GC5B420 | + | + | + | + | + | + |
| GC5B421 | + | + | + | + | + | + |
| GC5B243 | + | + | + | + | + | + |

Example 4: Generation of GPRC5D Antibodies Using Hydridoma Technology

Three Balb/c mice were immunized intradermally-base of tail with pCMV6-neo (CMV promoter) plasmid DNA expressing full length human GPRC5D on days 0, 10, and 20. Mice received final intraperitoneal and intravenous immunizations on day 59 with Rat Basophilic Leukemia (RBL) cells over-expressing full length human GPRC5D. On day 63, lymph nodes and spleens were harvested, enrichment of B cells was performed, and the cells were used to generate ~3500 mAb secreting hybridomas.

Figure 8A:
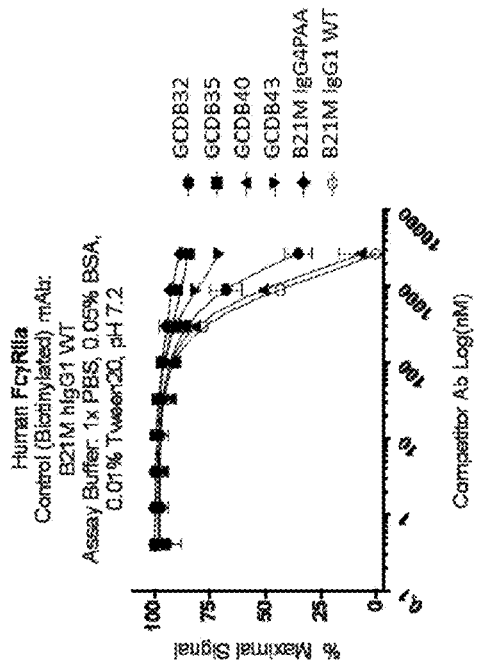
FIG. 8A-8D. Binding of GCDB32 GCDB35, GCDB40 and GCDB43 to Fcγ receptors.
Figure 8B:
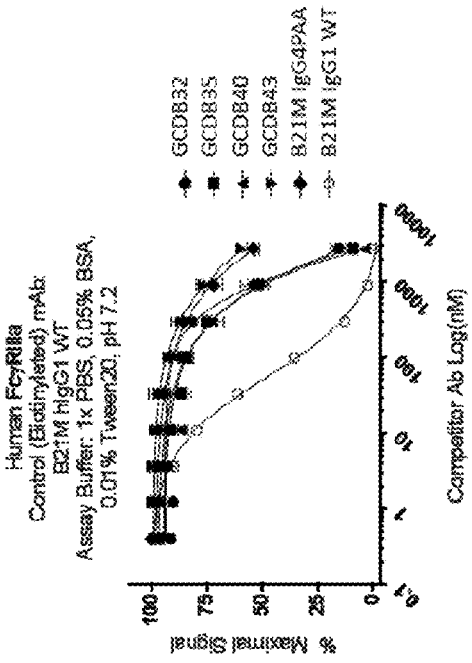
Figure 8C:
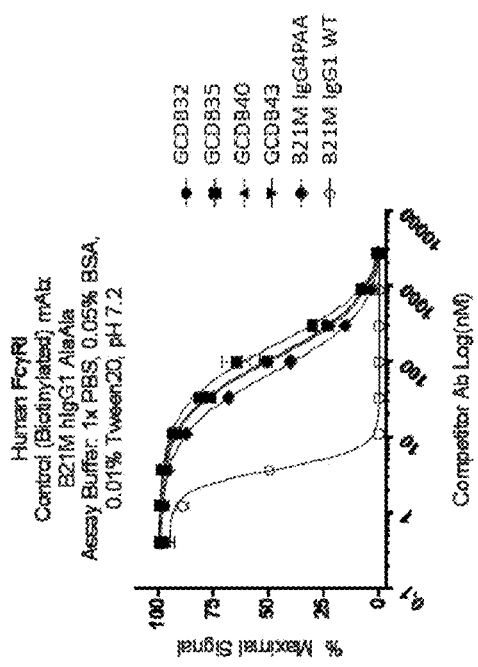
Figure 8D:
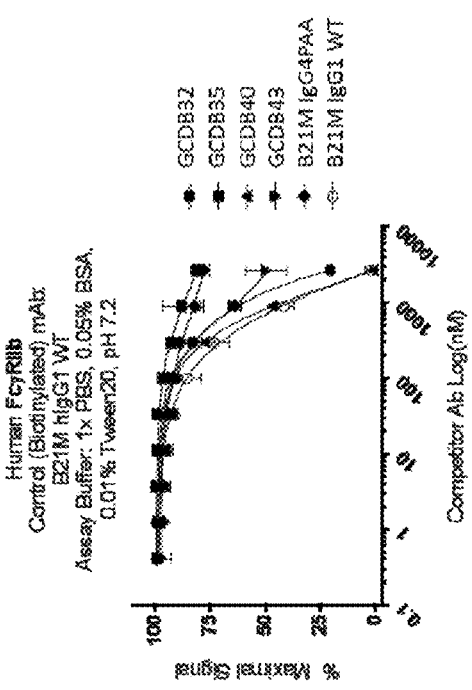
Figures 9A, 9B:
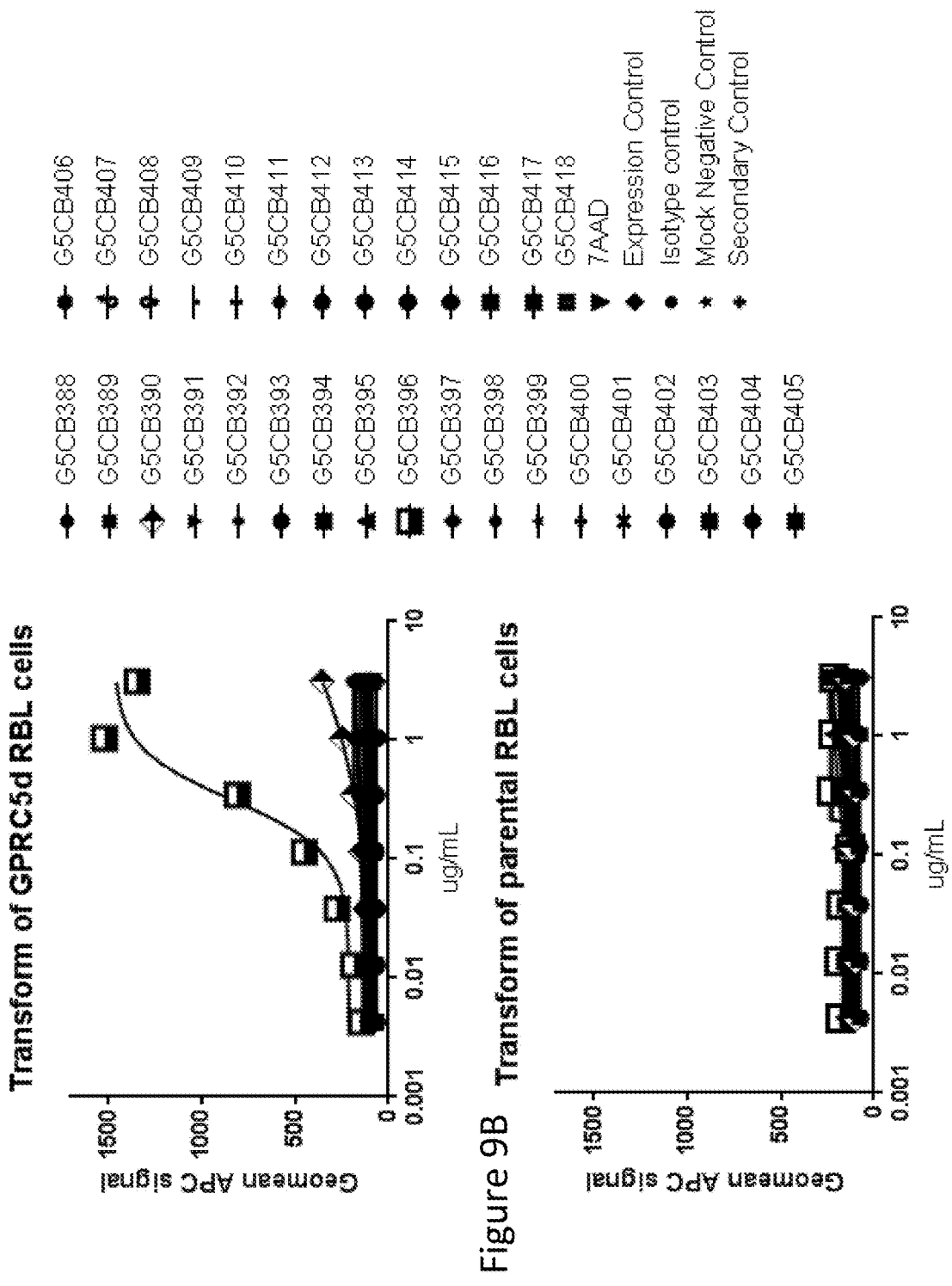
FIGS. 9A and 9B. FACS binding assessment of hybridoma derived mAbs.

Example 5: Initial Characterization of GPRC5D Antibodies Obtained Through Hyrbridoma Technology GPRC5D Binding The hybridomas were screened using FACS for binding to both RBL and human GPRC5D expressing RBL cells. The ratio of background adjusted MFI of each mAb binding to the GPRC5D RBL cells relative to the non-transfected RBL cells was calculated and any sample with a binding ratio greater than 3 were considered potentially positive. Ninety nine hybridomas had a ratio greater than 3 and were advanced for v-region cloning. Thirty one mAbs sequences were identified, synthesized, expressed and purified. Two of the 31 mAbs exhibited binding to RBL_GPRC5D cells above background (FIGS. 9A and 8B). GCDB390 and GCDB396 were selected for expression, purification and bispecific antibody generation with anti-CD3 arm CD3B219 to generate the bispecific antibodies GCDB46 and GCDB47, respectively.

T-Cell Dependent Cytotoxicity

Figures 10A, 10B:
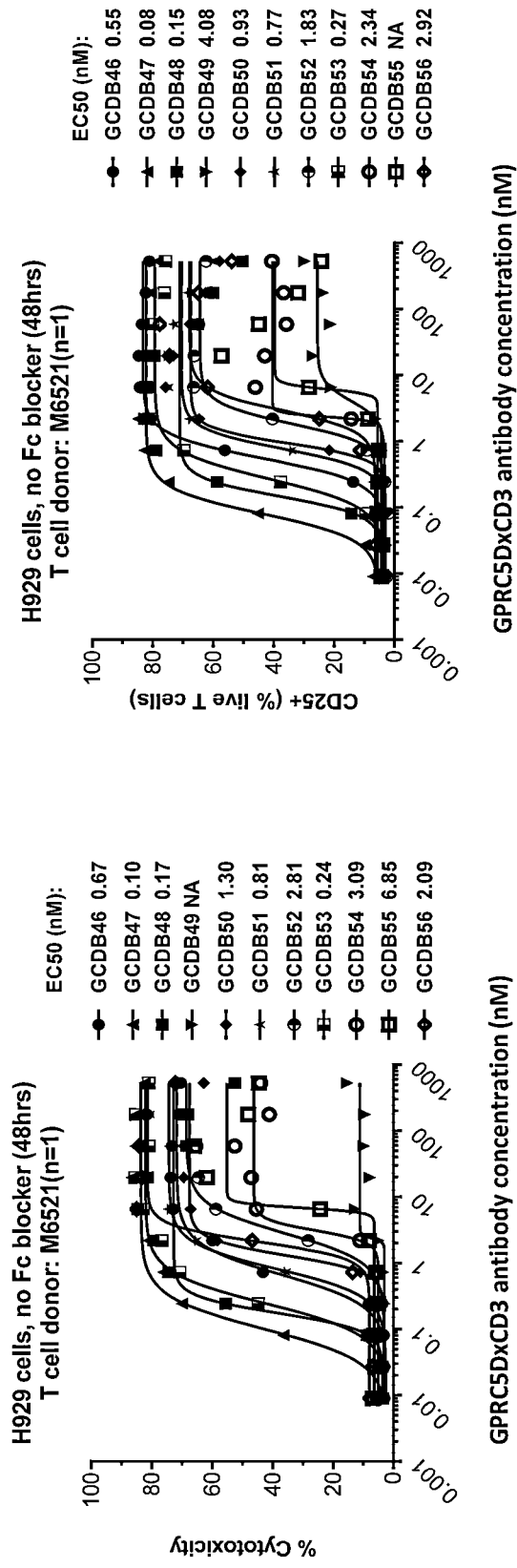
FIGS. 10A and 10B. T-cell mediated cytotoxicity of GPRC5D x CD3 bispecific antibodies against H929 cells.
Figure 12A:
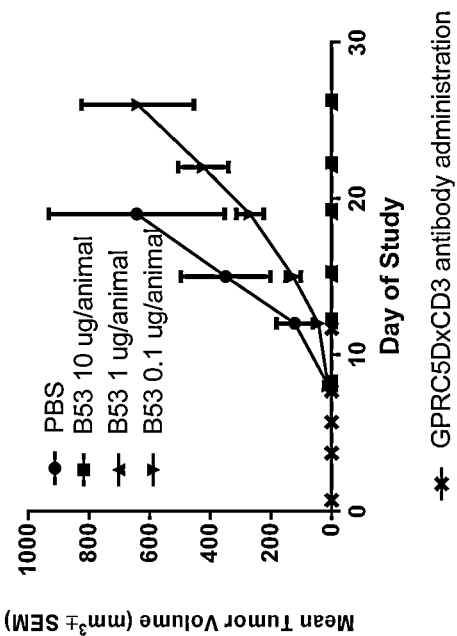
FIG. 12A-12D. GPRC5DxCD3 bispecific Abs are potent tumor inhibitors in vivo. All GPRC5D x CD3 bispecific Abs (GCDB32 shown in 12A, GCDB53 shown in 12B, GCDB61 shown in 12C, and GCDB72 shown in 12D) completely inhibited multiple myeloma cell (H929) tumor growth at the 10 ug and 1 ug doses. Differentiation was observed at the 0.1 ug dose with GCDB72 observed to have 80% tumor growth inhibition
Figure 12B:
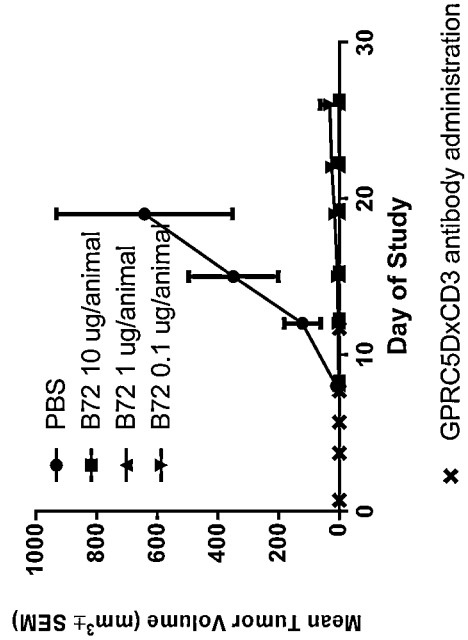
Figure 12C:
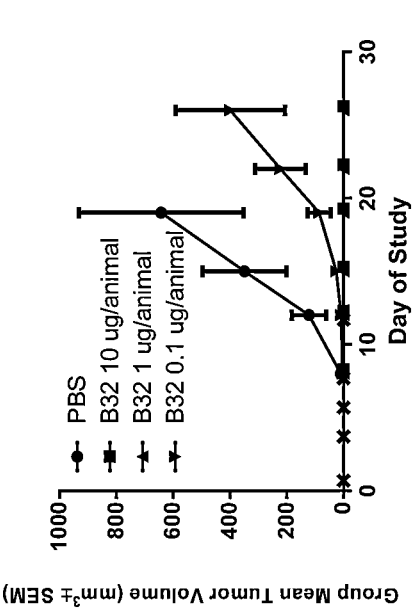
Figure 12D:
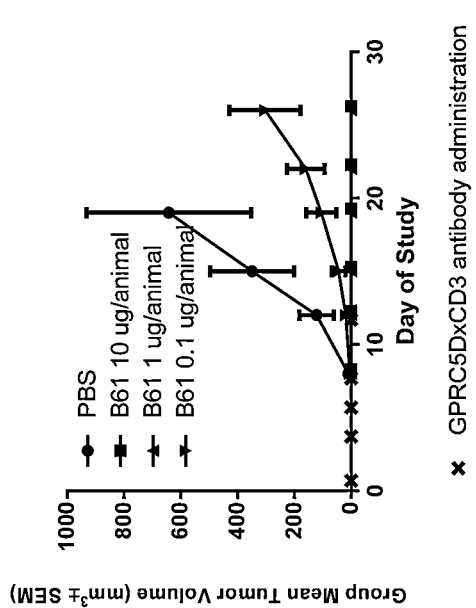

GCDB46 and GCDB47were assessed in the T-cell mediated cytotoxicity assay (FIGS. 10A and 10B). Both bispecific antibodies were observed to be potent, with reported $EC_{50}$ of 0.67 and 0.1 nM respectively. On the basis of these data both mAbs were advanced to lead optimization along with the three phage derived mAbs.

Example 6: Hit Evaluation, Selection and Optimization

Five GPRC5D bispecific antibodies were selected for lead optimization (GCDB32, GCDB43, GCDB35, GCDB46, GCDB47) based on binding, function, cross-reactivity and selectivity data summarized in Table 13.

TABLE 13

Lead optimization data for GPRC5D × CD3 bispecific antibodies. Bispecific antibodies were assessed for binding, function, cross-reactivity and selectivity.

| | Selectivity | T cell mediated Target cell killing | | | |
|---|---|---|---|---|---|
| GPRC5D × CD3 ID | Binding to GPRC5A, B, C | H929 EC50 ± SD (nM) | MM1R EC50 ± SD (nM) | H929 No Fc vs Fc Block | Cyno GPRC5D EC50 (nM) |
| GCDB32 | No Binding | 0.43 ± 0.29 | 0.12 ± 0.01 | 2.4 | 0.19 |
| GCDB43 | No Binding | 0.39 ± 0.07 | 0.54 | 2.8 | 0.95 |
| GCDB40 | No Binding | 1.2 ± 0.83 | 0.52 ± 0.31 | 5.1 | 10.61 |
| GCDB35 | Low | 1.39 ± 0.75 | 0.74 ± 0.26 | 2.7 | 4.65 |
| GCDB34 | No Binding | 2.01 ± 0.74 | 0.77 ± 0.09 | 6.3 | 1.14 |
| GCDB45 | No Binding | 2.36 ± 0.84 | 0.91 ± 0.76 | 2.2 | 2.82 |
| GCDB33 | No Binding | 5.21 ± 1.21 | 0.8 ± 0.15 | 1.5 | 0.2 |
| GCDB36 | Low | 5.57 ± 0.47 | 4.22 ± 0.29 | | 3.35 |
| GCDB46 | No Binding | 0.67 | | | |
| GCDB47 | No Binding | 0.1 | | | |
| GCDB48 | No Binding | 0.17 | | | Not Active |

Lead optimization was aimed at addressing potential post-translation modification (PTM) sequence risks for GCDB32 (GC5B81 parent mAb), GCDB43 (GC5B285 parent mAb) and GCDB35 (GC5B164 parent mAb) as outlined in Table 14.

TABLE 14

PTM mitigation sequence potential liabilities for Phage derived hits. The Hc CDR sequences are shown with potential PTM sequence liabilities are underlined. (SEQ ID NOs for each listed sequenceare provided in parenthesis)

| GPCR5D ID | GPRC5D Hc ID | Hc CDR1 | Hc CDR2 | HcCDR3 |
|---|---|---|---|---|
| GC5B81 | GC5H40 | SYAIS (1) | GIIPIFGTANYAQKFQG (5) | ESRWRGYKLD (9) |

TABLE 14-continued

PTM mitigation sequence potential liabilities for Phage derived hits. The Hc CDR sequences are shown with potential PTM sequence liabilities are underlined. (SEQ ID NOs for each listed sequenceare provided in parenthesis)

| GPCR5D ID | GPRC5D Hc ID | Hc CDR1 | Hc CDR2 | HcCDR3 |
|---|---|---|---|---|
| GC5B285 | GC5H14 | NYWMS (2) | GISYSGGSKYY ADSVKG (28) | AAWDFGRRAV RLDY (30) |
| GC5B164 | GC5H36 | SYWIG (27) | IIYPGDSDTRY SPSFQG (29) | VYSFGGRHKA LFDY (11) |

All of the PTM variants assayed for GC5B81 had a substantial reduction in binding affinity, demonstrating the criticality of this residue (HC W102) to the paratope (Table 15).

TABLE 15

CDR sequences and binding data of the GC5B81 PTM library. The site of mutation is underlined. Binding was classified as MFI >10,000 = ++; MFI >1,000 = +; MFI <1,000 (SEQ ID NOs for each listed sequence are provided in parenthesis)

| GPRC5D ID | Heavy Chain ID | Mutation | Hc CDR1 | Hc CDR2 | Hc CDR3 | Human GPRC5D (FACS) |
|---|---|---|---|---|---|---|
| GC5B427 | GC5H199 | W102Y | SYAIS (1) | GIIPIFGTANYAQKFQG (5) | ESRYRGYKLDY (31) | − |
| GC5B428 | GC5H198 | W102V | SYAIS (1) | GIIPIFGTANYAQKFQG (5) | ESRVRGYKLDY (32) | − |
| GC5B430 | GC5H196 | W102G | SYAIS (1) | GIIPIFGTANYAQKFQG (5) | ESRGRGYKLDY (33) | − |
| GC5B431 | GC5H195 | W102A | SYAIS (1) | GIIPIFGTANYAQKFQG (5) | ESRARGYKLDY (34) | − |
| GC5B429 | GC5H197 | W102F | SYAIS (1) | GIIPIFGTANYAQKFQG (5) | ESRFRGYKLDY (35) | − |

Binding studies identified a number of mutations for both GC5B285 and GC5B164 which retained binding to human GPRC5D (Tables 16 and 17).

TABLE 16

CDR sequences and binding data of the GC5B164 PTM library. Site of mutation is underlined. Binding was classified as MFI >10,000 = ++; MFI >1,000 = +; MFI <1,000. (SEQ ID NOs for each listed sequence are provided in parenthesis)

| GPRC5D ID | Heavy Chain ID | Mutation | Hc CDR1 | Hc CDR2 | Hc CDR3 | Human GPR5D Binding (FACS) |
|---|---|---|---|---|---|---|
| GC5B471 | GC5H278 | D55A, W33Y | SYYIG (36) | IIYPGASDTRYSPSFQG (40) | VYSFGGRHKALFDY (11) | ++ |
| GC5B472 | GC5H277 | D55A, W33V | SYVIG (37) | IIYPGASDTRYSPSFQG (40) | VYSFGGRHKALFDY (11) | + |
| GC5B473 | GC5H276 | D55A, W33F | SYFIG (3) | IIYPGASDTRYSPSFQG (40) | VYSFGGRHKALFDY (11) | ++ |
| GC5B474 | GC5H275 | D55A, W33G | SYGIG (38) | IIYPGASDTRYSPSFQG (40) | VYSFGGRHKALFDY (11) | + |
| GC5B475 | GC5H274 | D55A, W33A | SYAIG (39) | IIYPGASDTRYSPSFQG (40) | VYSFGGRHKALFDY (11) | + |

TABLE 16-continued

CDR sequences and binding data of the GC5B164 PTM library. Site of mutation is underlined. Binding was classified as MFI >10,000 = ++; MFI >1,000 = +; MFI <1,000. (SEQ ID NOs for each listed sequence are provided in parenthesis)

| GPRC5D ID | Heavy Chain ID | Mutation | Hc CDR1 | Hc CDR2 | Hc CDR3 | Human GPR5D Binding (FACS) |
|---|---|---|---|---|---|---|
| GC5B476 | GC5H273 | D55S, W33Y | SYYIG (36) | IIYPGSSDTRYSPSFQG (41) | VYSFGGRHKALFDY (11) | ++ |
| GC5B477 | GC5H272 | D55S, W33V | SYVIG (37) | IIYPGSSDTRYSPSFQG (41) | VYSFGGRHKALFDY (11) | + |
| GC5B478 | GC5H271 | D55S, W33F | SYFIG (3) | IIYPGSSDTRYSPSFQG (41) | VYSFGGRHKALFDY (11) | ++ |
| GC5B479 | GC5H270 | D55S, W33G | SYGIG (38) | IIYPGSSDTRYSPSFQG (41) | VYSFGGRHKALFDY (11) | + |
| GC5B480 | GC5H269 | D55S, W33A | SYAIG (39) | IIYPGSSDTRYSPSFQG (41) | VYSFGGRHKALFDY (11) | + |
| GC5B481 | GC5H268 | D55K, W33Y | SYYIG (36) | IIYPGKSDTRYSPSFQG (7) | VYSFGGRHKALFDY (11) | ++ |
| GC5B482 | GC5H267 | D55K, W33V | SYVIG (37) | IIYPGKSDTRYSPSFQG (7) | VYSFGGRHKALFDY (11) | ++ |
| GC5B483 | GC5H266 | D55K, W33F | SYFIG (3) | IIYPGKSDTRYSPSFQG (7) | VYSFGGRHKALFDY (11) | ++ |
| GC5B484 | GC5H265 | D55K, W33G | SYGIG (38) | IIYPGKSDTRYSPSFQG (7) | VYSFGGRHKALFDY (11) | + |
| GC5B485 | GC5H264 | D55K, W33A | SYAIG (39) | IIYPGKSDTRYSPSFQG (7) | VYSFGGRHKALFDY (11) | + |
| GC5B486 | GC5H263 | D55E, W33Y | SYYIG (36) | IIYPGESDTRYSPSFQG (42) | VYSFGGRHKALFDY (11) | ++ |
| GC5B487 | GC5H262 | D55E, W33V | SYVIG (37) | IIYPGESDTRYSPSFQG (42) | VYSFGGRHKALFDY (11) | + |
| GC5B488 | GC5H261 | D55E, W33F | SYFIG (3) | IIYPGESDTRYSPSFQG (42) | VYSFGGRHKALFDY (11) | ++ |
| GC5B489 | GC5H260 | D55E, W33G | SYGIG (38) | IIYPGESDTRYSPSFQG (42) | VYSFGGRHKALFDY (11) | − |
| GC5B490 | GC5H259 | D55E, W33A | SYAIG (39) | IIYPGESDTRYSPSFQG (42) | VYSFGGRHKALFDY (11) | + |
| GC5B491 | GC5H258 | D55Y, W33Y | SYYIG (36) | IIYPGYSDTRYSPSFQG (43) | VYSFGGRHKALFDY (11) | ++ |
| GC5B492 | GC5H257 | D55Y, W33V | SYVIG (37) | IIYPGYSDTRYSPSFQG (43) | VYSFGGRHKALFDY (11) | ++ |
| GC5B493 | GC5H256 | D55Y, W33F | SYFIG (3) | IIYPGYSDTRYSPSFQG (43) | VYSFGGRHKALFDY (11) | ++ |
| GC5B494 | GC5H255 | D55Y, W33G | SYGIG (38) | IIYPGYSDTRYSPSFQG (43) | VYSFGGRHKALFDY (11) | + |
| GC5B495 | GC5H254 | D55Y, W33A | SYAIG (39) | IIYPGYSDTRYSPSFQG (43) | VYSFGGRHKALFDY (11) | + |
| GC5B496 | GC5H253 | W33Y | SYYIG (36) | IIYPGDSDTRYSPSFQG (29) | VYSFGGRHKALFDY (11) | ++ |
| GC5B497 | GC5H252 | W33V | SYVIG (37) | IIYPGDSDTRYSPSFQG (29) | VYSFGGRHKALFDY (11) | ++ |
| GC5B498 | GC5H251 | W33F | SYFIG (3) | IIYPGDSDTRYSPSFQG (29) | VYSFGGRHKALFDY (11) | ++ |

TABLE 16-continued

CDR sequences and binding data of the GC5B164 PTM library. Site of mutation is underlined. Binding was classified as MFI >10,000 = ++; MFI >1,000 = +; MFI <1,000. (SEQ ID NOs for each listed sequence are provided in parenthesis)

| GPRC5D ID | Heavy Chain ID | Mutation | Hc CDR1 | Hc CDR2 | Hc CDR3 | Human GPR5D Binding (FACS) |
|---|---|---|---|---|---|---|
| GC5B499 | GC5H250 | W33G | SYGIG (38) | IIYPGDSDTRYSPSFQG (29) | VYSFGGRHKALFDY (11) | − |
| GC5B500 | GC5H249 | W33A | SYAIG (39) | IIYPGDSDTRYSPSFQG (29) | VYSFGGRHKALFDY (11) | − |
| GC5B501 | GC5H248 | D55A | SYWIG (27) | IIYPGASDTRYSPSFQG (40) | VYSFGGRHKALFDY (11) | ++ |
| GC5B502 | GC5H247 | D55S | SYWIG (27) | IIYPGSSDTRYSPSFQG (41) | VYSFGGRHKALFDY (11) | ++ |
| GC5B503 | GC5H246 | D55K | SYWIG (27) | IIYPGKSDTRYSPSFQG (7) | VYSFGGRHKALFDY (11) | ++ |
| GC5B504 | GC5H245 | D55E | SYWIG (27) | IIYPGESDTRYSPSFQG (42) | VYSFGGRHKALFDY (11) | ++ |
| GC5B505 | GC5H244 | D55Y | SYWIG (27) | IIYPGYSDTRYSPSFQG (43) | VYSFGGRHKALFDY (11) | ++ |

TABLE 17

CDR sequences and binding data of the GC5B285 PTM library. Site of mutation is underlined. Binding was classified as MFI >10,000 = ++; MFI >1,000 = +; MFI <1,000. (SEQ ID NOs for each listed sequence are provided in parenthesis)

| GPRC5D ID | Heavy Chain ID | Mutation | Hc CDR1 | Hc CDR2 | Hc CDR3 | Human GPRC5D (FACS) |
|---|---|---|---|---|---|---|
| GC5B463 | GC5H234 | D62A, W101Y | NYWMS (2) | GISYSGGSKYYAASVKG (44) | AAYDFGRRAVRLDY (48) | ++ |
| GC5B432 | GC5H228 | D62S, W101V | NYWMS (2) | GISYSGGSKYYASSVKG (6) | AAVDFGRRAVRLDY (49) | ++ |
| GC5B465 | GC5H227 | D62S, W101F | NYWMS (2) | GISYSGGSKYYASSVKG (6) | AAFDFGRRAVRLDY (97) | ++ |
| GC5B433 | GC5H223 | D62K, W101V | NYWMS (2) | GISYSGGSKYYAKSVKG (45) | AAVDFGRRAVRLDY (49) | ++ |
| GC5B434 | GC5H222 | D62K, W101F | NYWMS (2) | GISYSGGSKYYAKSVKG (45) | AAFDFGRRAVRLDY (97) | ++ |
| GC5B435 | GC5H219 | D62E, W101Y | NYWMS (2) | GISYSGGSKYYAESVKG (46) | AAYDFGRRAVRLDY (48) | + |
| GC5B436 | GC5H217 | D62E, W101F | NYWMS (2) | GISYSGGSKYYAESVKG (46) | AAFDFGRRAVRLDY (97) | + |
| GC5B461 | GC5H216 | D62E, W101G | NYWMS (2) | GISYSGGSKYYAESVKG (46) | AAGDFGRRAVRLDY (50) | − |
| GC5B462 | GC5H215 | D62E, W101A | NYWMS (2) | GISYSGGSKYYAESVKG (46) | AAADFGRRAVRLDY (51) | ++ |
| GC5B437 | GC5H214 | D62Y, W101Y | NYWMS (2) | GISYSGGSKYYAYSVKG (47) | AAYDFGRRAVRLDY (48) | + |
| GC5B438 | GC5H213 | D62Y, W101V | NYWMS (2) | GISYSGGSKYYAYSVKG (47) | AAVDFGRRAVRLDY (49) | + |
| GC5B439 | GC5H212 | D62Y, W101F | NYWMS (2) | GISYSGGSKYYAYSVKG (47) | AAFDFGRRAVRLDY (97) | + |

TABLE 17-continued

CDR sequences and binding data of the GC5B285 PTM library. Site of mutation is underlined. Binding was classified as MFI >10,000 = ++; MFI >1,000 = +; MFI <1,000. (SEQ ID NOs for each listed sequence are provided in parenthesis)

| GPRC5D ID | Heavy Chain ID | Mutation | Hc CDR1 | Hc CDR2 | Hc CDR3 | Human GPRC5D (FACS) |
|---|---|---|---|---|---|---|
| GC5B440 | GC5H211 | D62Y, W101G | NYWMS (2) | GISYSGGSKYYAYSVKG (47) | AAGDFGRRAVRLDY (50) | − |
| GC5B441 | GC5H210 | D62Y, W101A | NYWMS (2) | GISYSGGSKYYAYSVKG (47) | AAADFGRRAVRLDY (51) | + |
| GC5B442 | GC5H209 | W101Y | NYWMS (2) | GISYSGGSKYYADSVKG (28) | AAYDFGRRAVRLDY (48) | + |
| GC5B443 | GC5H208 | W101V | NYWMS (2) | GISYSGGSKYYADSVKG (28) | AAVDFGRRAVRLDY (49) | + |
| GC5B444 | GC5H207 | W101F | NYWMS (2) | GISYSGGSKYYADSVKG (28) | AAFDFGRRAVRLDY (97) | + |
| GC5B464 | GC5H206 | W101G | NYWMS (2) | GISYSGGSKYYADSVKG (28) | AAGDFGRRAVRLDY (50) | + |
| GC5B445 | GC5H205 | W101A | NYWMS (2) | GISYSGGSKYYADSVKG (28) | AAADFGRRAVRLDY (51) | + |
| GC5B446 | GC5H204 | D62A | NYWMS (2) | GISYSGGSKYYAASVKG (44) | AAWDFGRRAVRLDY (30) | + |
| GC5B447 | GC5H203 | D62S | NYWMS (2) | GISYSGGSKYYASSVKG (6) | AAWDFGRRAVRLDY (30) | + |
| GC5B448 | GC5H202 | D62K | NYWMS (2) | GISYSGGSKYYAKSVKG (45) | AAWDFGRRAVRLDY (30) | + |
| GC5B449 | GC5H201 | D62E | NYWMS (2) | GISYSGGSKYYAESVKG (46) | AAWDFGRRAVRLDY (30) | + |
| GC5B450 | GC5H200 | D62Y | NYWMS (2) | GISYSGGSKYYAYSVKG (47) | AAWDFGRRAVRLDY (30) | + |

On the basis of this binding data, selected mAbs were generated as GPRC5D x CD3 bispecific antibodies and assessed for T-cell mediated cytotoxicity of H929 cells (Table 18).

TABLE 18

Functional Activity of selected GPRC5D PTM variants for GCDB164 and GCDB285

| Parent GPRC5D mAb ID | GPRC5D Protein AA ID | GPRC5D x CD3 ID | H929 $EC_{50}$ (nM) | Selected as Lead |
|---|---|---|---|---|
| GC5B285 | GC5B432 | GCDB50 | 1.3 | |
| | GC5B433 | GCDB51 | 0.81 | |
| | GC5B434 | GCDB52 | 2.81 | |
| | GC5B465 | GCDB53 | 0.24 | XX |
| | GC5B463 | GCDB54 | 3.09 | |
| GC5B164 | GC5B471 | GCDB57 | 3.87 | |
| | GC5B476 | GCDB58 | 1.24 | |
| | GC5B478 | GCDB59 | 1.54 | |
| | GC5B481 | GCDB60 | 2.94 | |
| | GC5B483 | GCDB61 | 1.51 | XX |
| | GC5B493 | GCDB62 | 3.1 | |

A range of potency was observed it the T-cell mediated cytotoxicity assay that was not necessarily predicted by the observed binding affinity. For example, GC5B465 and GC5B463 bound with similar affinity to human GPRC5D differ only in the sequence of 2 amino acids (Table 17) and were observed to have a 12.5 fold difference in potency as GPRC5D x CD3 bispecific Abs (Table 18). On the basis of the functional data GC5B465 and GC5B483 were selected as optimized sequences for GC5B285 (GCDB43 as CD3 bispecific) and GC5B164 (GCDB35 as CD3 bispecific).

Human framework adaptation was also completed for the murine hybridoma derived GPCR5D mAbs (GC5B390 and GC5B396, or GCDB46 and 47 as CD3 bispecific, respectively). Binding studies identified a number of frameworks for GC5B396 and one framework for GC5B390 which retained binding to human GPRC5D (Table 19).

TABLE 19

Binding and functional data for the human framework adaptation of hybridoma derived anti-GPRC5D mAb libraries.
Binding was classified as MFI > 10,000 = +++; MFI > 5,000 = ++; MFI > 1,000 = +; MFI < 1,000.

| GPRC5D Parent mAb ID | GPRC5D mAb AA ID | Heavy Chain ID | Light Chain ID | Human GPRC5D (FACS) | GPRC5D x CD3 ID | H929 EC50 (nM) |
|---|---|---|---|---|---|---|
| GPRC5D B396 | GC5B541 | GC5H241 | GC5L58 | + | | |
| | GC5B540 | GC5H240 | GC5L58 | +++ | GCDB69 | 0.58 |
| | GC5B539 | GC5H242 | GC5L58 | ++ | | |
| | GC5B538 | GC5H243 | GC5L58 | ++ | | |
| | GC5B537 | GC5H241 | GC5L57 | + | | |
| | GC5B536 | GC5H240 | GC5L57 | +++ | GCDB68 | 2.51 |
| | GC5B535 | GC5H242 | GC5L57 | + | | |
| | GC5B534 | GC5H243 | GC5L57 | ++ | | |
| | GC5B533 | GC5H241 | GC5L56 | + | | |
| | GC5B532 | GC5H240 | GC5L56 | +++ | GCDB67 | 0.61 |
| | GC5B531 | GC5H242 | GC5L56 | ++ | | |
| | GC5B530 | GC5H243 | GC5L56 | +++ | GCDB66 | 1.41 |
| | GC5B529 | GC5H241 | GC5L55 | ++ | | |
| | GC5B528 | GC5H240 | GC5L55 | +++ | GCDB65 | 1.01 |
| | GC5B527 | GC5H242 | GC5L55 | − | | |
| | GC5B526 | GC5H243 | GC5L55 | ++ | GCDB64 | 1.5 |
| GPRC5D B390 | GC5B525 | GC5H279 | GC5L53 | − | | |
| | GC5B524 | GC5H237 | GC5L53 | − | | |
| | GC5B523 | GC5H238 | GC5L53 | − | | |
| | GC5B522 | GC5H236 | GC5L53 | − | | |
| | GC5B521 | GC5H279 | GC5L52 | − | | |
| | GC5B520 | GC5H237 | GC5L52 | − | | |
| | GC5B519 | GC5H238 | GC5L52 | − | | |
| | GC5B518 | GC5H236 | GC5L52 | − | | |
| | GC5B517 | GC5H279 | GC5L51 | + | | |
| | GC5B516 | GC5H237 | GC5L51 | + | | |
| | GC5B515 | GC5H238 | GC5L51 | ++ | GCDB63 | 0.52 |
| | GC5B514 | GC5H236 | GC5L51 | + | | |
| | GC5B513 | GC5H279 | GC5L50 | − | | |
| | GC5B512 | GC5H237 | GC5L50 | + | | |
| | GC5B511 | GC5H238 | GC5L50 | + | | |
| | GC5B510 | GC5H236 | GC5L50 | + | | |
| | GC5B509 | GC5H279 | GC5L49 | − | | |
| | GC5B508 | GC5H237 | GC5L49 | + | | |
| | GC5B507 | GC5H238 | GC5L49 | + | | |
| | GC5B506 | GC5H236 | GC5L49 | + | | |

On the basis of the binding data several anti-GPCR5D mAbs were generated as CD3 bispecific antibodies and assessed for T-cell mediated cytotoxicity of H929 cells (Table 18). Functional analysis identified GCDB63, GCDB67, and GCDB69 as potent fully humanized GPRC5D x CD3 bispecific antibodies. On the basis of these data, the corresponding anti-GPRC5D mAbs, GC5B515, GC5B532, and GC5B540 were selected as the fully humanized sequences for GC5B390 and GC5B391.

Additional lead optimization of the fully humanized sequences was then completed aimed at addressing potential post-translation modification sequence risks for GC5B515, GC5B532, and GCDB540. A G56S mutation was generated in the heavy chain sequence to remove a potential deamidation risk for GC5B515 (Table 20).

TABLE 20

Binding and Functional Activity of selected GPRC5D PTM variants for GC5B532, GC5B540 and GCDB515.

| GPRC5D Parent mAb ID | GPRC5D mAb AA ID | Mutation | Human GPRC5D (FACS) | GPRC5D x CD3 ID | H929 EC50 (nM) |
|---|---|---|---|---|---|
| GC5B540 | GC5B590 | M64K | +++ | | |
| | GC5B592 | G99A | + | | |
| | GC5B594 | M64K, G99A | + | | |

TABLE 20-continued

Binding and Functional Activity of selected GPRC5D PTM variants for GC5B532, GC5B540 and GCDB515.

| GPRC5D Parent mAb ID | GPRC5D mAb AA ID | Mutation | Human GPRC5D (FACS) | GPRC5D x CD3 ID | H929 EC50 (nM) |
|---|---|---|---|---|---|
| GC5 B532 | GC5B591 | M64K | +++ | | |
| | GC5B593 | G99A | + | | |
| | GC5B595 | M64K, G99A | + | | |
| GC5 B515 | GC5B596 | G56S | ++ | GCDB72 | 0.15 |

The heavy chains for GC5B532 and GC5B540 contained both a potential isomerization and an oxidation risk. M64K and G99A mutations were generated to ameliorate this risk (Table 20). All of the variants tested with the G99A mutation had a substantial reduction in binding affinity, while the M64K and G56A variants were not impacted. Based on the binding data alone GC5B596 was progressed to functional assessment and demonstrated potency as a CD3 bispecific (GCDB72) in T-cell mediated cytotoxicity assays.

Thus, four GPRC5D bispecific mAbs were selected for additional characterization: GCDB32, GCDB53, GCDB61, and GCDB72. Depicted below in Tables 21 and 22 are the CDR and heavy and light chain sequences of the GPRC5D mAbs used for the generation of the bispecific molecules.

TABLE 21

CDR sequences of 4 GPRC5D mAb candidates that showed binding against human and cyno GPRC5D and that were functional when generated as CD3 bispecifics.

| ID | HC-CDR1 | HC-CDR2 | HC-CDR3 | LC-CDR1 | LC-CDR2 | LC-CDR3 |
|---|---|---|---|---|---|---|
| GC5B81 | SYAIS (SEQ ID NO 1) | GIIPIFGTANYAQKFQG (SEQ ID NO 5) | ESRWRGYKLD (SEQ ID NO 9) | RASQSISSYLN (SEQ ID NO 13) | AASSLQS (SEQ ID NO 16) | QQSYSTPLT (SEQ ID NO 19) |
| GC5B465 | NYWMS (SEQ ID NO 2) | GISYSGGSKYYASSVKG (SEQ ID NO 6) | AAFDFGRRAVRLD (SEQ ID NO 10) | RASQSISSYLN (SEQ ID NO 13) | AASSLQS (SEQ ID NO 16) | QQSYSTPLT (SEQ ID NO 19) |
| GC5B483 | SYFIG (SEQ ID NO 3) | IIYPGKSDTRYSPSFQG (SEQ ID NO 7) | VYSFGGRHKALFDY (SEQ ID NO 11) | RASQSVSSYLA (SEQ ID NO 14) | DASNRAT (SEQ ID NO 17) | QQRSNWPLT (SEQ ID NO 20) |
| GC5B596 | GYTMN (SEQ ID NO 4) | LINPYNSDTNYAQKLQG (SEQ ID NO 8) | VALRVALDY (SEQ ID NO 12) | KASQNVATHVG (SEQ ID NO 15) | SASYRYS (SEQ ID NO 18) | QQYNRYPYT (SEQ ID NO 21) |

TABLE 22

Heavy and light chain variable region sequences of 4 GPRC5D mAb candidates that showed binding against human and cyno GPRC5D and that were functional when generated as CD3 bispecifics.

| mAb AA ID | VH Amino Acid Sequence | SEQ ID NO: | VL Amino Acid Sequence | SEQ ID NO |
|---|---|---|---|---|
| GC5B81 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARESRWRGYKLDYWGQGTLVTVSS | 52 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 56 |
| GC5B465 | EVQLLESGGGLVQPGGSLRLSCAASGFTFSNYWMSWVRQAPGKGLEWVSGISYSGSKYYASSVKGRFTISRDNSKNTLYLQMNSLRAEDTAVYYCAKAAFDFGRRAVRLDYWGQGTLVTVSS | 53 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 56 |
| GC5B483 | EVQLVQSGAEVKKPGESLKISCKGSGYSFTSYFIGWVRQMPGKGLEWMGIIYPGKSDTRYSPSFQGQVTISADKSISTAYLQWSSLKASDTAMYYCARVYSFGGRHKALFDYWGQGTLVTVSS | 54 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIK | 57 |
| GC5B596 | QVQLVQSGAEVKKPGASVKVSCKASGYSFTGYTMNWVRQAPGQGLEWMGLINPYNSDTNYAQKLQGVTMTTDTSTSTAYMELRSLRSDDTAVYYCARVALRVALDYWGQGTLVTVSS | 55 | DIQMTQSPSSLSASVGDRVTITCKASQNVATHVGWYQQKPGKAPKRLIYSASYRYSGVPSRFSGSGSGTEFTLTISNLQPEDFATYYCQQYNRYPYTFGQGTKLEIK | 58 |

Example 7: Preparation of GPRC5D and CD3 Antibodies in A Bispecific Format in IgG4 S228P, L234A, L235A The four monospecific GPRC5D antibodies (see table 21) were expressed as IgG4, having Fc substitutions S228P, L234A, and L235A or S228P, L234A, L235A, F405L, and R409K (CD3 arm) (numbering according to EU index). A monospecific anti-CD3 antibody CD3B219 was also generated comprising the VH and VL regions having the heavy chain of SEQ ID NO: 25 and the light chain of SEQ ID NO: 26 and IgG4 constant region with S228P, L234A, L235A, F405L, and R409K substitutions.

The monospecific antibodies were purified using standard methods using a Protein A column (HiTrap MabSelect SuRe column). After elution, the pools were dialyzed into D-PBS, pH 7.2.

Bispecific GPRC5D x CD3 antibodies were generated by combining a monospecific CD3 mAb and a monospecific GPRC5D mAb in in-vitro Fab arm exchange (as described in WO2011/131746). Briefly, at about 1-20 mg/mL at a molar ratio of 1.08:1 of anti-GPRC5D/anti-CD3 antibody in PBS, pH 7-7.4 and 75 mM 2-mercaptoethanolamine (2-MEA) was mixed together and incubated at 25-37° C. for 2-6 hours, followed by removal of the 2-MEA via dialysis, diafiltration, tangential flow filtration and/or spin cell filtration using standard methods.

Heavy and Light chains for the GPRC5D x CD3 bispecific Abs are shown below in Table 23.

TABLE 23

Heavy and Light Chain Sequences for bispecific Abs IgG4-PAA

| Ab | | Amino Acid Sequence |
|---|---|---|
| GCDB32 | Heavy chain 1 CD3B219 (SEQ ID NO: 25) | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS |
| | Light Chain 1 CD3B219 (SEQ ID NO: 26) | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL |
| | Heavy chain 2 GC5B81 (SEQ ID NO: 52) | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARESRWRGYKLDYWGQGTLVTVSS |
| | Light Chain 2 GC5B81 (SEQ ID NO: 56) | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK |
| GCDB53 | Heavy chain 1 CD3B219 (SEQ ID NO: 25) | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS |

TABLE 23-continued

Heavy and Light Chain Sequences for bispecific Abs IgG4-PAA

| Ab | | Amino Acid Sequence |
|---|---|---|
| | Light Chain 1 CD3B219 (SEQ ID NO: 26) | QTVVTQEPSLTVSPGGTVTLTCRSSTGAVTTS NYANWVQQKPGQAPRGLIGGTNKRAPGTPA RFSGSLLGGKAALTLSGVQPEDEAEYYCALW YSNLWVFGGGTKLTVL |
| | Heavy chain 2 GC5B465 (SEQ ID NO: 53) | EVQLLESGGGLVQPGGSLRLSCAASGFTFSNY WMSWVRQAPGKGLEWVSGISYSGGSKYYAS SVKGRFTISRDNSKNTLYLQMNSLRAEDTAV YYCAKAAFDFGRRAVRLDYWGQGTLVTVSS |
| | Light Chain 2 GC5B465 (SEQ ID NO: 56) | DIQMTQSPSSLSASVGDRVTITCRASQSISSYL NWYQQKPGKAPKLLIYAASSLQSGVPSRFSG SGSGTDFTLTISSLQPEDFATYYCQQSYSTPL TFGQGTKVEIK |
| GCD B61 | Heavy chain 1 CD3B219 (SEQ ID NO: 25) | EVQLVESGGGLVQPGGSLRLSCAASGFTFNT YAMNWVRQAPGKGLEWVARIRSKYNNYAT YYAASVKGRFTISRDDSKNSLYLQMNSLKTE DTAVYYCARHGNFGNSYVSWFAYWGQGTL VTVSS |
| | Light Chain 1 CD3B219 (SEQ ID NO: 26) | QTVVTQEPSLTVSPGGTVTLTCRSSTGAVTTS NYANWVQQKPGQAPRGLIGGTNKRAPGTPA RFSGSLLGGKAALTLSGVQPEDEAEYYCAL WYSNLWVFGGGTKLTVL |
| | Heavy chain 2 GC5B483 (SEQ ID NO: 54) | EVQLVQSGAEVKKPGESLKISCKGSGYSFTS YFIGWVRQMPGKGLEWMGIIYPGKSDTRYS PSFQGQVTISADKSISTAYLQWSSLKASDTA MYYCARVYSFGGRHKALFDYWGQGTLVT VSS |
| | Light Chain 2 GC5B483 (SEQ ID NO: 57) | EIVLTQSPATLSLSPGERATLSCRASQSVSSY LAWYQQKPGQAPRLLTYDASNRATGIPARF SGSGSGTDFTLTISSLEPEDFAVYYCQQRSN WPLTFGQGTKVEIK |
| GCD B72 | Heavy chain 1 CD3B219 (SEQ ID NO: 25) | EVQLVESGGGLVQPGGSLRLSCAASGFTFNT YAMNWVRQAPGKGLEWVARIRSKYNNYAT YYAASVKGRFTISRDDSKNSLYLQMNSLKTE DTAVYYCARHGNFGNSYVSWFAYWGQGTL VTVSS |
| | Light Chain 1 CD3B219 (SEQ ID NO: 26) | QTVVTQEPSLTVSPGGTVTLTCRSSTGAVTTS NYANWVQQKPGQAPRGLIGGTNKRAPGTPA RFSGSLLGGKAALTLSGVQPEDEAEYYCAL WYSNLWVFGGGTKLTVL |
| | Heavy chain 2 GC5B596 (SEQ ID NO: 55) | QVQLVQSGAEVKKPGASVKVSCKASGYSFT GYTMNWVRQAPGQGLEWMGLINPYNSDTN YAQKLQGRVTMTTDTSTSTAYMELRSLRSD DTAVYYCARVALRVALDYWGQGTLVTVSS |
| | Light Chain 2 GC5B596 (SEQ ID NO: 58) | DIQMTQSPSSLSASVGDRVTITCKASQNVAT HVGWYQQKPGKAPKRLIYSASYRYSGVPSR FSGSGSGTEFTLTISNLQPEDFATYYCQQYN RYPYTFGQGTKLEIK |

Example 8: Functional Characterization of GCDB32, GCDB53, GCDB61, and GCDB72

GCDB32, GCDB53, GCDB61, and GCDB72 were assessed for binding to murine GPRC5D (Table 24). All four bispecific antibodies bound to murine GPRC5D, with a range of binding affinities observed.

TABLE 24

Binding of anti-GPCR5D × CD3 antibodies to murine GPRC5D

| GPRC5D × CD3 ID | Murine GPRC5D FACS binding (MFI) |
|---|---|
| GCDB32 | 1151 |
| GCDB53 | 2658 |
| GCDB61 | 3552 |
| GCDB72 | 481 |

Cross-reactivity with cyno GPRC5D was also assessed using the T-cell redirection cytotoxicity assay of overexpressed human and cyno GPRC5D cell lines (Table 25). One GPRC5D × CD3 bispecific antibody was equipotent against human and cyno GPRC5D (GCDB32), while the other bispecifics tested were less potent at inducing cytotoxicity of cyno GPRC5D than human GPRC5D.

TABLE 25

Functional activity of lead GPRC5D × CD3 antibodies against human and cyno GPRC5D-expressing HEK cells.

| GPRC5D × CD3 ID | Human GPRC5D HEK cells ($EC_{50}$ nM) | Cyno GPRC5D HEK cells ($EC_{50}$ nM) |
|---|---|---|
| GCDB32 | 0.04 | 0.07 |
| GCDB53 | 0.08 | 0.36 |
| GCDB61 | 0.03 | 1.22 |
| GCDB72 | 0.03 | 3.41 |

Additional characterization was aimed at understanding in vitro binding (FIG. 11A-11E) and potency (Table 26).

TABLE 26

T-cell mediated cytotoxicity of several human GPRC5D-expressing B cell lines by lead GPRC5D × CD3 antibodies.

| GPRC5D × CD3 ID | H929 cells $EC_{50}$ nM (Rank order) | MM1R $EC_{50}$ nM (Rank order) | OPM2 $EC_{50}$ nM (Rank order) | LP-1 $EC_{50}$ nM (Rank Order) |
|---|---|---|---|---|
| GCDB32 | 0.45 (3) | 0.04 (1) | 0.98 (2) | 1.02 (2) |
| GCDB53 | 0.69 (4) | 0.28 (4) | 2.83 (4) | 1.58 (3) |
| GCDB61 | 0.39 (2) | 0.06 (3) | 1.46 (3) | 1.67 (4) |
| GCDB72 | 0.22 (1) | 0.04 (1) | 0.77 (1) | 0.7 (1) |

Figure 15A:
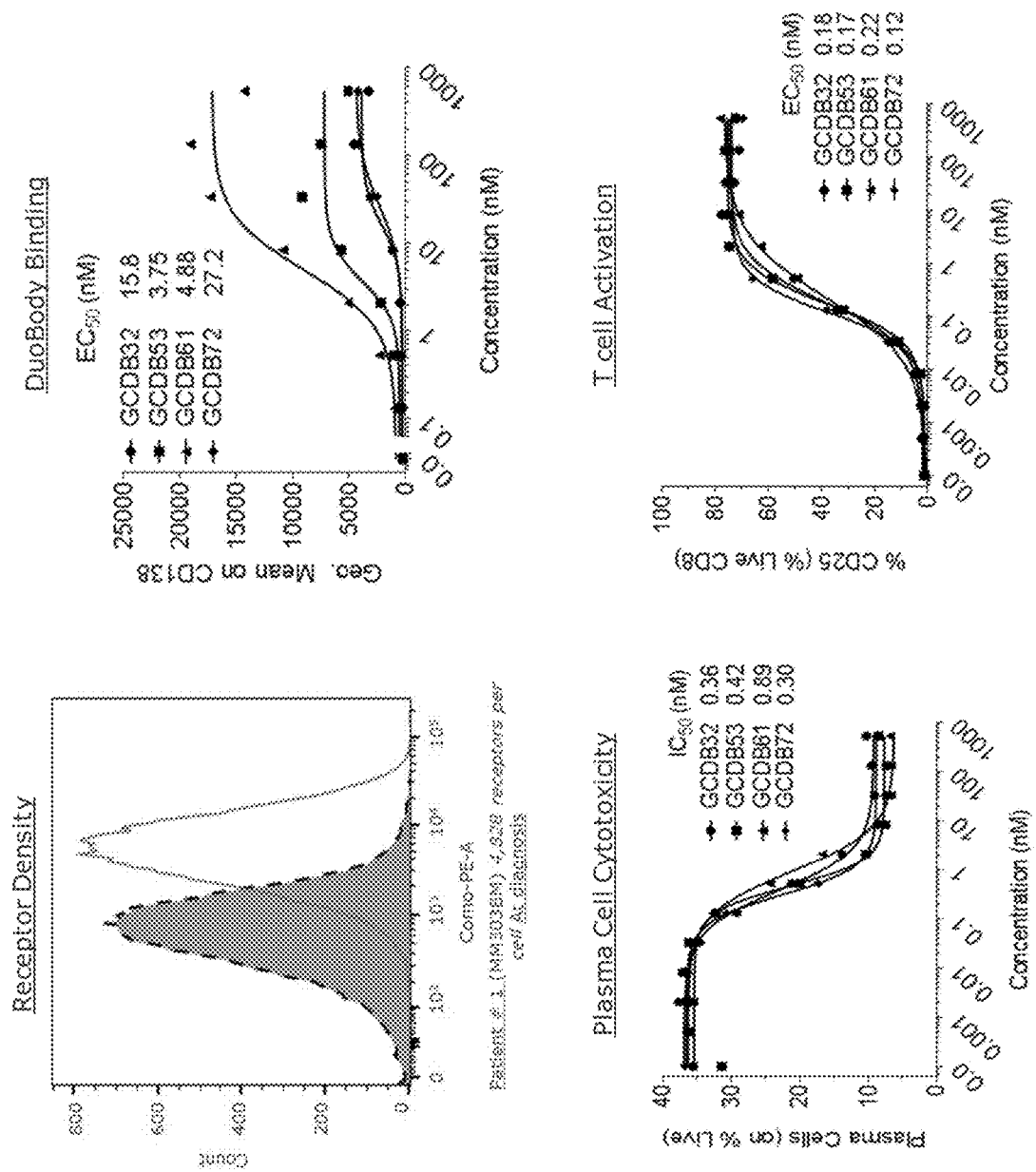
FIGS. 15A and 15B. Frozen bone marrow-derived mononuclear cells from two different MM patients were used to assess GPRC5D x CD3 bispecific antibody binding, compared to IgG4 isotype control, plasma cell cytotoxicity and T-cell activation. For the cytotoxicity assay, T cells from the normal healthy donor were exogenously added to patient BM MNC samples and incubated with four lead molecules for 48 hours. GPRC5D x CD3 bispecific antibody binds to plasma cells in a dose dependent manner to all donor samples and the mean fluorescence intensities were recorded on the Y-axis. Note the loss of live plasma cells (CD138$^+$) and the concomitant upregulation of CD25 on T cells in response to GPRC5D x CD3 bispecific antibody treatment.
Figure 15B:
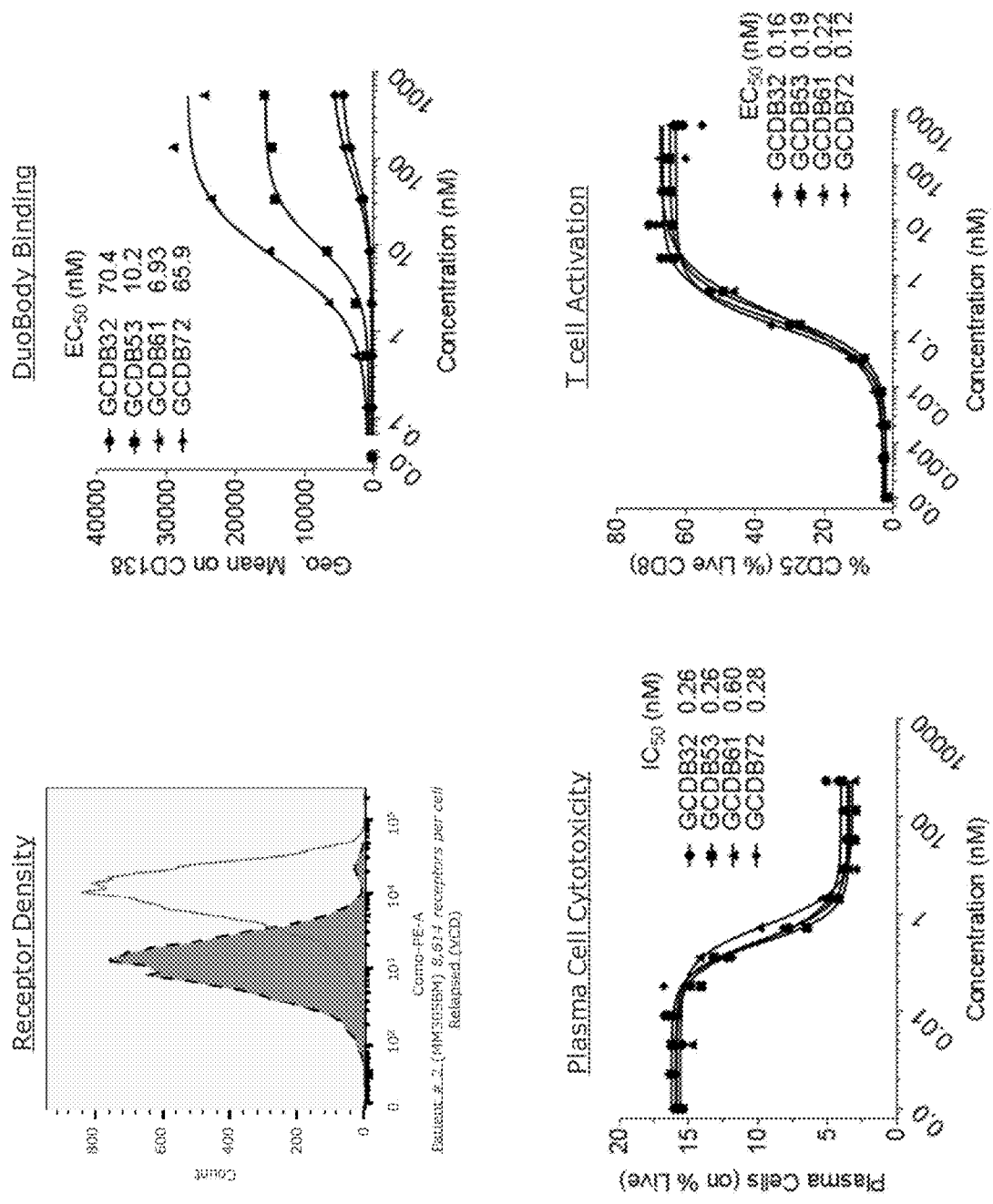

While a range of binding affinities were observed, with GCDB61 the strongest binder and GCDB72 & GCDB32 the weakest binders, the in vitro potencies were very similar for the panel of bispecific antibodies. However, based on rank order analysis GCDB72 was the most potent across the various B cell lines analyzed. Ex vivo binding and potency experiments using patient derived MNCs yielded larger similar results to the in vitro assays (Table 27 and FIGS. 15A and 15B).

TABLE 27

GPCR5D × CD3 bispecific antibody binding, T-cell mediated cytotoxicity, and T-cell activation of MM patient derived MNCs.

| Patient | GPRC5D × CD3 AA ID | Binding $EC_{50}$ nM | Cytotoxicity $EC_{50}$ nM | T cell activation $EC_{50}$ nM |
|---|---|---|---|---|
| MM303BM | GCDB32 | 16.1 | 0.36 | 0.18 |
| | GCDB53 | 3.98 | 0.42 | 0.17 |
| | GCDB61 | 5.53 | 0.89 | 0.22 |
| | GCDB72 | 27.5 | 0.30 | 0.12 |
| MM305BM | GCDB32 | 70.4 | 0.26 | 0.16 |
| | GCDB53 | 10.2 | 0.26 | 0.19 |
| | GCDB61 | 6.93 | 0.6 | 0.22 |
| | GCDB72 | 65.9 | 0.28 | 0.12 |

GCDB61 had the highest binding affinity to patient MNCs while GCDB72 & GCDB32 were the weakest binders. Again, even though differences in binding affinity were observed, all bispecific antibodies demonstrated sub-nanomolar efficacy in T-cell redirected cytotoxicity assays. The molecules were virtually indistinguishable on the basis of in vitro and ex vivo potency however, in vivo data provided differentiation (FIG. 12A-12D).

H929 cells were implanted into NSG mice, one week following injection of human PBMCs. Treatment of the bispecific antibodies was initiated at the same time that the H929 cells were implanted and continued every 2 or 3 days (q2d or q3d) at 10 ug, 1 ug, and 0.1 ug/animal doses for a total of five treatments. Ten mice were used in each group and PBS included as the vehicle control. Treatment was stopped at day 11 and the study was terminated on day 26 (FIG. 12 A-D). All the GPRC5D x CD3 bispecific molecules tested in this prophylactic model showed 100% tumor growth inhibition at the 10 and 1 ug/animal dose. Differentiation was observed at the lowest dose, 0.1 ug/animal, with GCDB72 demonstrating superiority to the other bispecific antibodies tested with 80% tumor growth inhibition observed.

Example 9: GPRC5D Antibody Binding Profile on GPRC5D+Mm1.R Cell Line

Figure 13:
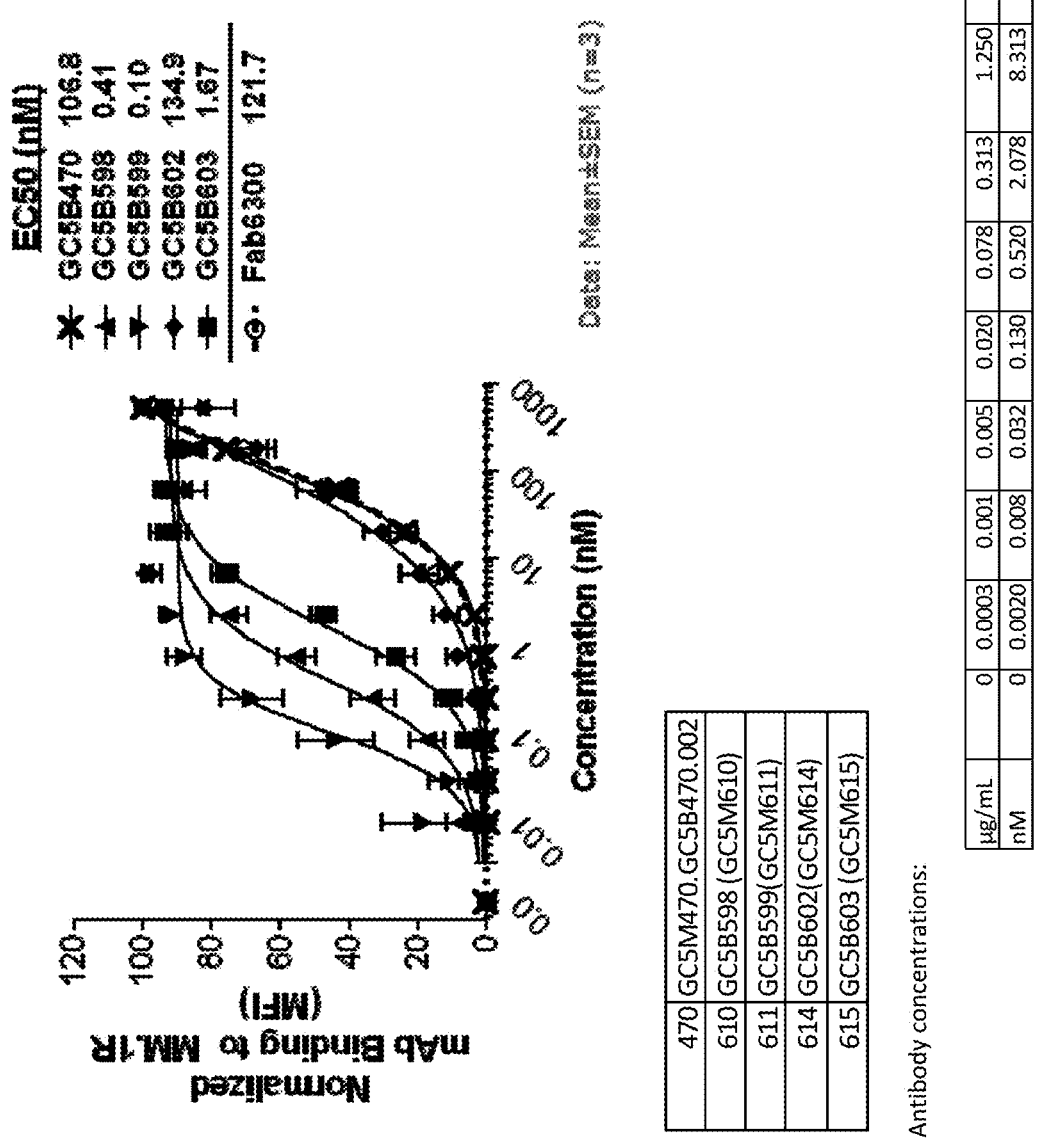
FIG. 13: GPRC5D$^+$ MM1.R cell lines were stained for 60 minutes with various concentrations of lead antibodies to measure the surface binding profiles (n=3). Phycoerythrin labelled human IgG4Fc was used as a secondary antibody to capture the signal (Southern Biotech, clone HP6025). Binding is expressed as normalized geometrical mean fluorescence intensity as determined by FACS. Graphing and fitting of data were done in GraphPad Prism 6 using nonlinear regression with variable slope (four parameters) and least square fit method.

The binding affinities of the GPRC5D antibodies on GPRC5D+ human MM cell line (MM1.R, purchased from ATCC (American Type Culture Collection)) were measured using FACS. FIG. 13 shows that all the lead antibodies bound to GPRC5D expressing MM.1R cells in a dose dependent manner with $EC_{50}$ values ranging from 0.10 nM to 135 nm all of which except GC5B602 are significantly lower than the values of commercial antibody FAB6300 (R& D Systems Cat No. FAB6300A, Clone No. 571961) which yielded an $EC_{50}$ value of 121.7 nM. GPRC5D+ MM1.R cell lines were stained for 60 minutes with various concentrations of lead antibodies to measure the surface binding profiles (n=3). Phycoerythrin labelled human IgG4Fc was used as a secondary antibody to capture the signal (Southern Biotech, clone HP6025, Cat #9200-09). Binding is expressed as normalized geometrical mean fluorescence intensity as determined by FACS. Graphing and fitting of data were done in GraphPad Prism 6 using non-linear regression with variable slope (four parameters) and least square fit method.

Figure 14A:
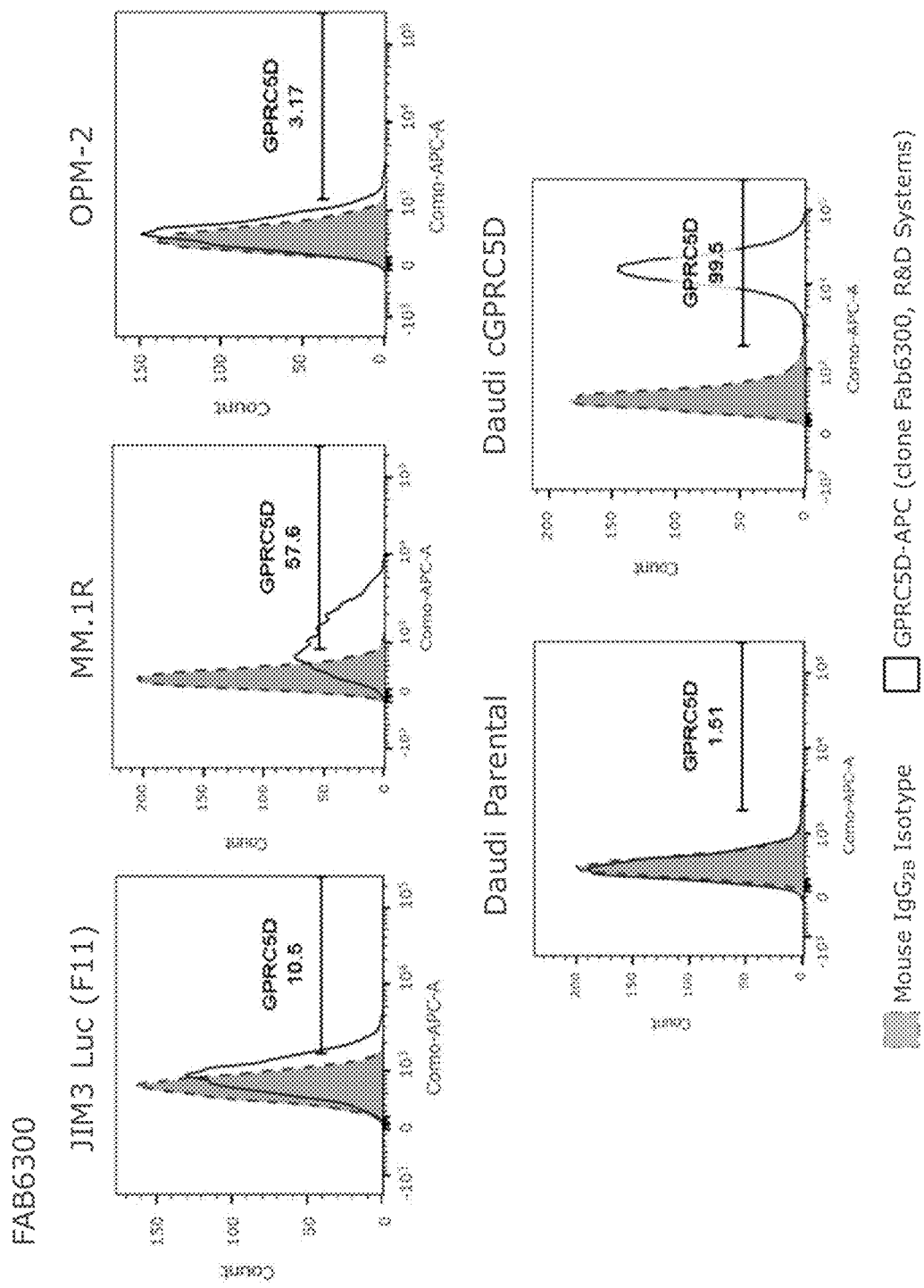
FIGS. 14A and 14B. GPRC5D$^+$ cell lines were stained for 60 minutes with various concentrations of FAB6300 and GC5M481 antibodies to measure the surface binding profiles. Phycoerythrin labelled human IgG4Fc was used as a secondary antibody to capture the signal (Southern Biotech, clone HP6025). Binding is expressed as histograms (black line for the isotype and the red line denotes for the specific GPRC5D antibody (FIG. 14A).
Figure 14B:
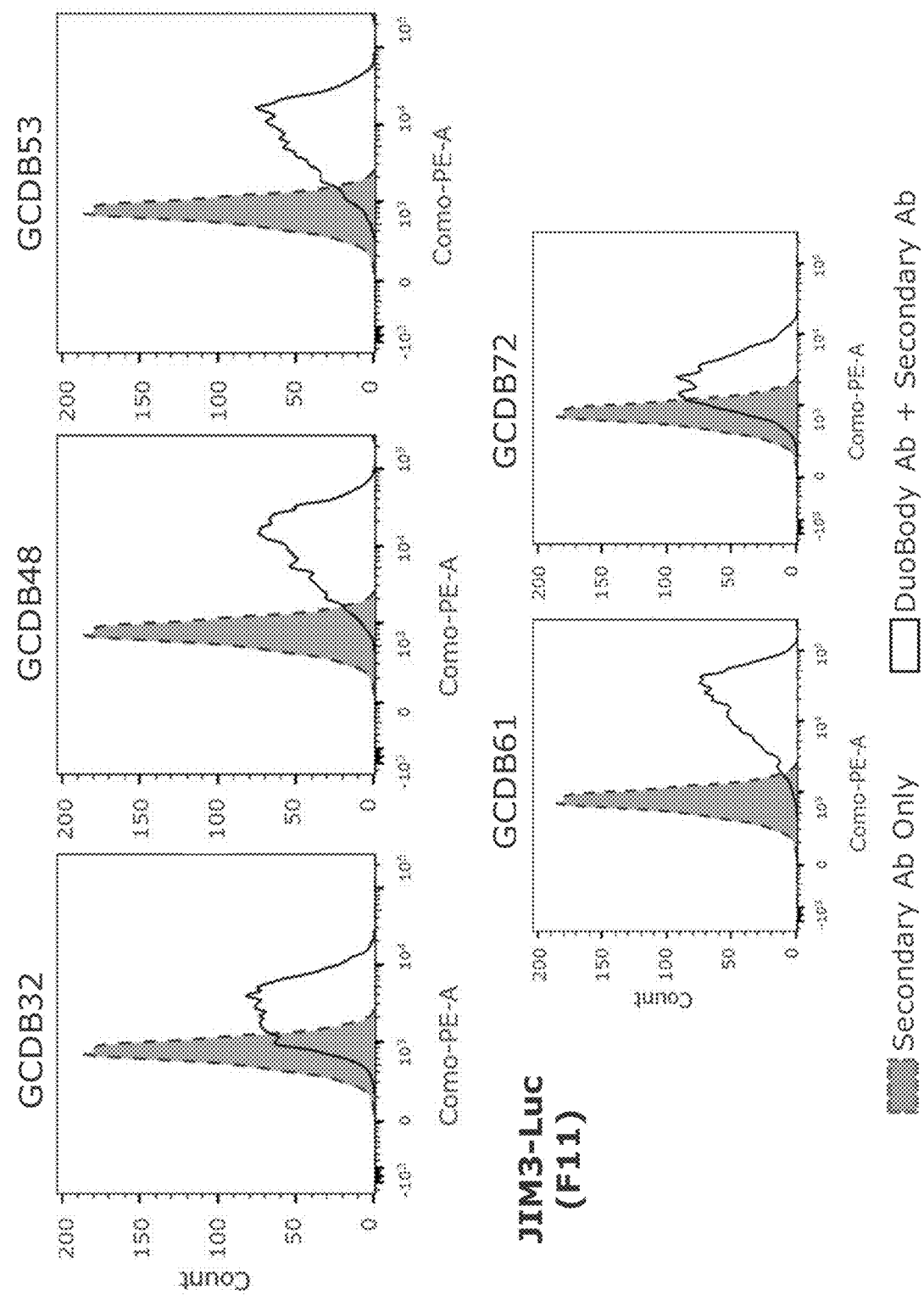

In addition, the GPRC5D mAb GC5M481 binding profile was assessed in comparison with the commercial antibody using three GPRC5D+(JIM3,OPM-2, and MM.1R; Cell lines purchased from ATCC) multiple myeloma cell lines (FIG. 14A). Further, the GPRC5D mAb (GC5M481) was profiled for cyno cross-reactivity using a cyno-GPRC5D expressing Daudi cells which showed strong binding compared to the parental cells (FIG. 14A). Also, five GPRC5D x CD3 bispecific antibodies (GCDB32, GCDB48, GCDB53, GCDB61 and GCDB72) when evaluated for the binding potential using GPRC5D+(JIM3, OPM-2 and MM1.R) cell lines (FIG. 14B) showed a significant binding as evident by the shift in the histogram (black solid trace) compared to the isotype control (dotted, gray filled trace).

Figure 16:
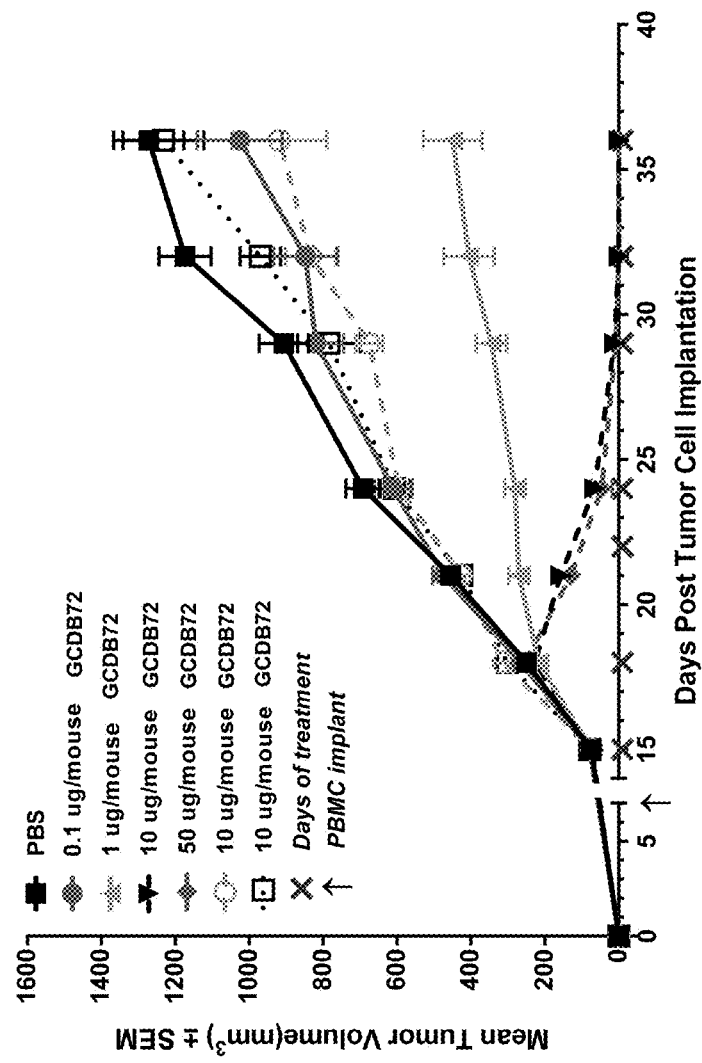
FIG. 16. NSG mice were subcutaneously implanted with MM.1S human Multiple Myeloma cells on Day 0. Human PBMC were intravenously inoculated on study day 7. PBS, GCDB72 (0.1 µg, 1 µg, 10 µg and 50 µg/animal (equivalent to 0.005, 0.05, 0.5 and 2.5 mg/kg, respectively)) and Null control antibodies were intravenously dosed on Days 15, 18, 22, 24, 29, 32 and 36. Subcutaneous tumors were measured twice weekly and the results were presented as the mean tumor volume, expressed mm$^3$±SEM of each group. GCDB72 antibody treatment when dosed at 1 (0.05 mg/kg) significantly inhibited sc tumor growth compared to PBS (TGI=64%, p≤0.0001). GCDB72 doses of 10 µg/animal (0.5 mg/kg) and 50 µg/animal (2.5 mg/kg) completely regressed tumor growth (p≤0.0001). The Null control antibodies had negligible or no effect. Statistical significance was evaluated using a 2-way ANOVA with multiple comparisons using Tukey's multiple comparisons test using Graph Pad Prism software (version 6). Differences between groups were considered significant when the probability value (p) was ≤0.05.
Figure 17:
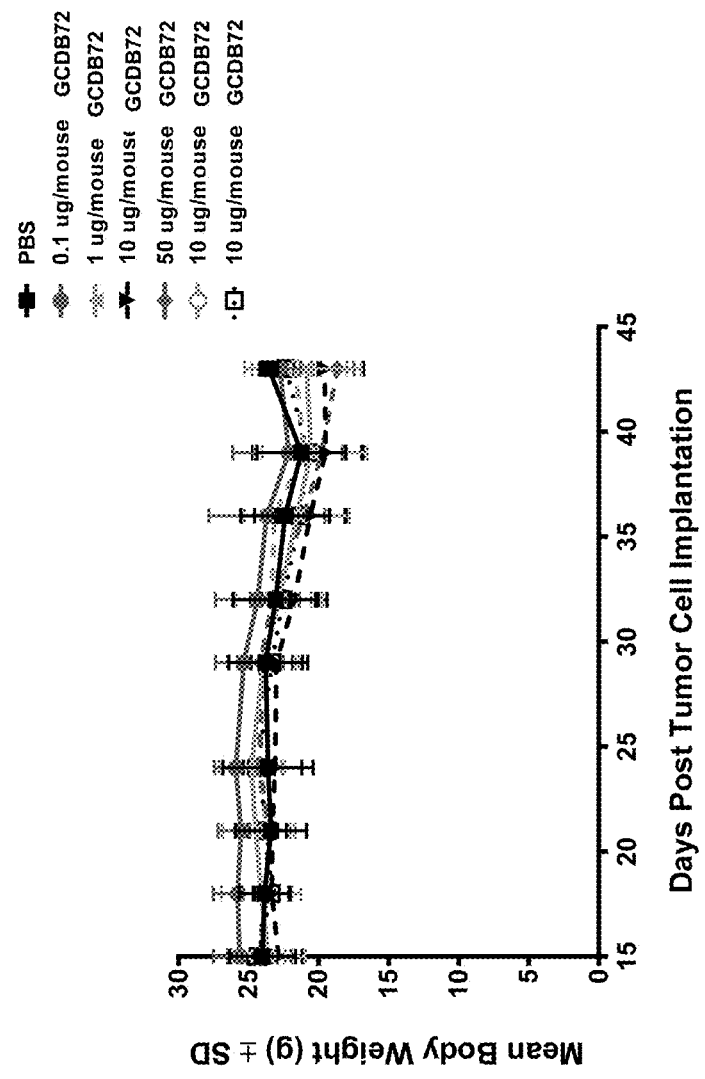
FIG. 17. NSG were subcutaneously implanted with MM.1S human Multiple Myeloma cells on Day 0. Human PBMC were intravenously inoculated on study day 7. PBS, GCDB72 (0.1 µg, 1 µg, 10 µg and 50 µg/animal (equivalent to 0.005, 0.05, 0.5 and 2.5 mg/kg, respectively)) and Null control antibodies were intravenously dosed on Days 15, 18, 22, 24, 29, 32 and 36. Body weight is presented as absolute body weight from start of treatment to the end of study

Example 10: Anti-Tumor Efficacy of GCDB72 Against Subcutaneous MM.1S Human Multiple Myeloma Xenografts in PBMC-Humanized NSG Mice This in vivo study was performed to determine the efficacy of GCDB72 against established MM.1S human multiple myeloma (MM) xenografts in PBMC humanized NSG mice. Female NSG mice of similar weight and age were subcutaneously (sc) implanted with MM.1S human MINI cells ($1 \times 10^7$ cells in 200 μL PBS per mouse) on the right dorsal hind flank on study day 0. On day 7 post tumor cell implantation, $1 \times 10^7$ human PBMC (in 200 μL PBS) were injected intravenously via the lateral tail vein. Treatments were initiated on day 15 when mean tumor volume was approximately 72-78 mm$^3$, each mouse received intravenous (iv) administration of PBS or GCDB72 DuoBody antibody at 0.1 μg (0.005 mg/kg), 1 (0.05 mg/kg), 10 μg (0.5 mg/kg) and 50 μg (2.5 mg/kg). Null DuoBody controls, CD3 x Null and Null x GPRC5D, were each dosed at 10 μg per mouse. Treatments were administered approximately every three days (q3d) for a total of seven doses. Robust anti-tumor efficacy was observed with the two high doses (10 μg and 50 μg) of GCDB72 where MM.1S sc tumors completely regressed in 100% (10 of 10 per group) of the animals by the end of the study (FIG. 16). Moreover, the 1 μg per mouse dose significantly inhibited tumor growth by 65% (p≤0.0001) compared to PBS treated tumors, while the 0.1 μg dose had little effect (TGI=19.3%, p=0.0023). The effect of CD3 x Null was not considered efficacious (TGI=28%, p≤0.0001) and Null x GPRC5D had negligible effect of 3.1% TGI, p=0.9971. TGI was determined on day 36 when there at least 80% viable animals per group. Significant body weight loss and/or mortality began to manifest post day 36 due to GVHD (FIG. 17). The study was terminated on day 43 when there were 60% or less animals remaining in the groups.

Example 11: Antibody-Dependent Cell-Mediated Cytotoxicity (ADCC) of GPRC5D Antibodies A panel of anti-human GPRC5D mAbs were generated as IgG1 mAbs. In addition, a new panel of anti-human GPRC5D mAbs were generated as described in Example 2. Depicted below in Tables 28 and 29 are the CDR and heavy and light chain variable region sequences of the new GPRC5D mAbs. These new antibodies were used for the generation of bispecific CD3 molecules as described in Example 7 and also incorporated as IgG1 mAbs for ADCC activity assessment.

TABLE 28

CDR sequences of new panel of GPRC5D antibodies

| ID | HC-CDR1 | HC-CDR2 | HC-CDR3 | LC-CDR1 | LC-CDR2 | LC-CDR3 |
|---|---|---|---|---|---|---|
| GC5B382 | DYGMH (SEQ ID NO 61) | AIKYSGGSTYYADSVKG (SEQ ID NO 67) | RAESGPGLDY (SEQ ID NO 72) | KSSQSVLYSSNNKNYLA (SEQ ID NO 98) | WASTRES (SEQ ID NO 78) | QQYYSTPLT (SEQ ID NO 80) |
| GC5B379 | NYWMS (SEQ ID NO 2) | GISYSGGSKYYADSVKG (SEQ ID NO 28) | AAWDFGRRAVRLDY (SEQ ID NO 30) | RASQSISSYLN (SEQ ID NO 13) | AASSLQS (SEQ ID NO 16) | QQSYSTPLT (SEQ ID NO 19) |
| GC5B373 | SYWIG (SEQ ID NO 27) | IIYPGDSDTRYSPSFQG (SEQ ID NO 29) | IGFYGRSFRIFDY (SEQ ID NO 73) | RASQSVSSYLA (SEQ ID NO 14) | DASNRAT (SEQ ID NO 17) | QQRSNWPLT (SEQ ID NO 20) |
| GC5B376 | SYWIG (SEQ ID NO 27) | IIYPGDSDTRYSPSFQG (SEQ ID NO 29) | VYSFGGRHKALFDY (SEQ ID NO 11) | RASQSVSSYLA (SEQ ID NO 14) | DASNRAT (SEQ ID NO 17) | QQRSNWPLT (SEQ ID NO 20) |
| GC5B385 | GYAMS (SEQ ID NO 62) | AISGSGGSTYYADSVKG (SEQ ID NO 68) | VDRSFGRSRYTLDY (SEQ ID NO 74) | RASQSVSSYLA (SEQ ID NO 14) | DASNRAT (SEQ ID NO 17) | QQRSNWPLT (SEQ ID NO 20) |
| GC5B370 GC5B597 | SYGIS (SEQ ID NO 63) | GIIPIFGNINYAQKFQG (SEQ ID NO 69) | VSRRFKRFAYYFDY (SEQ ID NO 75) | KSSQSVLYSSNNKNYLA (SEQ ID NO 98) | WASTRES (SEQ ID NO 78) | QQYYSTPLT (SEQ ID NO 80) |
| GC5B602 | GYSFTGYTMN (SEQ ID NO 64) | LINPYNGDTN (SEQ ID NO 70) | VALRVALDY (SEQ ID NO 12) | KASQNVATHVG (SEQ ID NO 15) | SASYRYS (SEQ ID NO 18) | QQYNRYPYT (SEQ ID NO 21) |
| GC5B603 | SYAMS (SEQ ID NO 65) | AISGSGGSTYYADSVKG (SEQ ID NO 68) | SNFLPVVFDY (SEQ ID NO 76) | RASQSVRKSLA (SEQ ID NO 95) | TASNRAT (SEQ ID NO 79) | QQYFRAPIT (SEQ ID NO 81) |
| GC5B601 | GFSLTSYNVH (SEQ ID NO 66) | VIWAGGSTNYNSALMS (SEQ ID NO 71) | DGIRLRFAY (SEQ ID NO 77) | KASQNVATHVG (SEQ ID NO 15) | SASYRYS (SEQ ID NO 18) | QQYNRYPYT (SEQ ID NO 21) |

TABLE 29

Heavy and Light chain variable region sequences of new panel of GPRC5D antibodies

| mAb AA ID | VH Amino Acid Sequence | SEQ ID NO: | VL Amino Acid Sequence | SEQ ID NO |
|---|---|---|---|---|
| GC5B 382 | EVQLLESGGGLVQPGGSLRLSCAASGFTFSDYGMHWVRQAPGKGLEWVSAIKYSGGSTYYADSVKGRFTISRDNSKNTLYLQMNSLRAEDTAVYYCAKRAESGPGLDYWGQGTLVTVSS | 82 | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPLTFGQGTKVEIK | 92 |
| GC5B 379 | EVQLLESGGGLVQPGGSLRLSCAASGFTFSNYWMSWVRQAPGKGLEWVSGISYSGGSKYYADSVKGRFTISRDNSKNTLYLQMNSLRAEDTAVYYCAKAAWDFGRRAVRLDYWGQGTLVTVSS | 83 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 56 |
| GC5B 373 | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARIGFYGRSFRIFDYWGQGTLVTVSS | 84 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIK | 57 |
| GC5B 376 | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARVYSFGGRHKALFDYWGQGTLVTVSS | 85 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIK | 57 |
| GC5B 385 | EVQLLESGGGLVQPGGSLRLSCAASGFTFSGYAMSWVRQAPGKGLEWVSAISGSGGSTYYADSVKGRFTISRDNSKNTLYLQMNSLRAEDTAVYYCAKVDRSFGRSRYTLDYWGQGTLVTVSS | 86 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIK | 57 |
| GC5B 370 GC5B 597 | QVQLVQSGAEVKKPGSSVKVSCKASGGTFSSYGISWVRQAPGQGLEWMGGIIPIFGNINYAQKFQGRVTITADESTSTAYMELSSLRSEDTAVYYCARVSRRFKRFAYYFDYWGQGTLVTVSS | 87 | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPLTFGQGTKVEIK | 92 |
| GC5B 602 | QVQLVQSGAEVKKPGASVKVSCKASGYSFTGYTMNWVRQAPGQGLEWMGLINPYNGDTNYAQKLQGRVTMTTDTSTSTAYMELRSLRSDDTAVYYCARVALRVALDYWGQGTLVTVSS | 88 | DIQMTQSPSSLSASVGDRVTITCKASQNVATHVGWYQQKPGKAPKRLIYSASYRYSGVPSRFSGSGSGTEFTLTISNLQPEDFATYYCQQYNRYPYTFGQGTKLEIK | 58 |
| GC5B 603 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKSNFLPVVFDYWGQGTLVTVSS | 89 | EIVLTQSPATLSLSPGERATLSCRASQSVRKSLAWYQQKPGQAPRLLIYTASNRATGIPARFSGSGSGTDFTLTISSLEPEDFAVYYCQQYFRAPITFGQGTKVEIKK | 93 |

TABLE 29-continued

Heavy and Light chain variable region sequences of new panel of GPRC5D antibodies

| mAb AA ID | VH Amino Acid Sequence | SEQ ID NO: | VL Amino Acid Sequence | SEQ ID NO |
|---|---|---|---|---|
| GC5B 601 | QVTLKESGPVLVKP TETLTLTCTVSGFS LTSYNVHWIRQPPG KALEWLAVIWAGG STNYNSALMSRLTI SKDTSKSQVVLTM TNMRAEDTATYYC ARDGIRLRFAYWG QGTLVTVSS | 91 | EIVMTQSPATLSVSP GERATLSCKASQNV ATHVGWYQQKPGQ APRLLIYSASYRYSG IPARFSGSGSGTEFTL TISSLQSEDFAVYYC QQYNRYPYTFGQG TKLEIK | 94 |

ADCC activity against H929 cells (Tables 30 and 31). Briefly, multiple myeloma cells were labeled with Calcein-AM for 30 minutes at room temperature and re-suspend at 0.2×10⁶/ml in RPMI+10% HI FBS after two PBS washes. PBMC's were thawed and resuspended after PBS wash at 3×10⁶ cells per ml in RPMI growth media. 10000 or 50000 target cells were mixed with 100000 or 2500000 PBMC'S in presence of the antibody and incubated for 3 hours in CO₂ incubator at 37° C. After the incubation plate was centrifuges at 200 g for 4 minutes and 100 ul of supernatant was transferred into a new 96 well plate and the fluorescence intensity was measured at 485/535 nM. RFU values were plotted to calculate the percent lysis

TABLE 30

Antibody dependent cytotoxicity of H929 cells by anti-GPRC5D mAbs with IgG1 Fc.

| GPRC5D IgG4 Protein ID | GPRC5D IgG1 Protein ID | H929 Cytotoxicity EC₅₀ (pM) | % Lysis |
|---|---|---|---|
| GC5B243 | GC5B382 | 1346.5 | 29.14 |
| GC5B285 | GC5B379 | 87.4 | 17.3 |
| GC5B332 | GC5B373 | 244.2 | 32.94 |
| GC5B164 | GC5B376 | 22.0 | 32.21 |
| GC5B320 | GC5B385 | 944.0 | 29.73 |
| GC5B251 | GC5B370 | 24.2 | 8 |
| GC5B515 | GC5B602 | 27721.7 | 20 |
| GC5B420 | GC5B603 | 3.4 | 16 |
| GC5B483 | GC5B599 | 7.4 | 14 |
| GC5B540 | GC5B601 | 169.6 | 14 |
| GC5B465 | GC5B598 | 2.0 | 12 |
| GC5B251 | GC5B597 | 705.1 | 10 |

TABLE 31

Comparison of Antibody dependent cytotoxicity and T-cell mediated cytotoxicity of H929 cells.

| GPRC5D IgG1 Protein ID | GPRC5D × CD3 DuoBody ID | ADCC H929 Cytotoxicity EC50 (pM) | CD3 Redirection T-cell Mediated H929 Cytotoxicity EC50 (nM) |
|---|---|---|---|
| GC5B382 | GCDB40 | 1346.5 | 1.2 ± 0.83 |
| GC5B379 | GCDB43 | 87.4 | 0.39 ± 0.07 |
| GC5B373 | GCDB45 | 244.2 | 2.36 ± 0.84 |
| GC5B376 | GCDB35 | 22.0 | 1.39 ± 0.75 |
| GC5B385 | GCDB44 | 944.0 | >10 |
| GC5B370 | GCDB41 | 24.2 | >10 |
| GC5B602 | GCDB72 | 27721.7 | 0.15 |
| GC5B603 | GCDB48 | 3.4 | 0.17 |
| GC5B599 | GCDB61 | 7.4 | 1.51 |
| GC5B601 | GCDB69 | 169.6 | 0.58 |
| GC5B598 | GCDB53 | 2.0 | 0.24 |

A range of potency was observed ranging from 2 pM to 27.7 nM. Binding affinity was not necessarily predictive of efficacy in the ADCC assay. For example, GC5B382 and GC5B379 had similar binding affinity to human GPRC5D cells but a 15x difference in cytotoxicity against H929 cells in the ADCC assay. Similarly, cytotoxic inducement as a GPRC5D x CD3 bispecific was not predictive of potency in the ADCC assay as exemplified by GC5B370 and GC5B602. When formatted as a CD3 bispecific GC5B602 (GCDB63) had sub-nanomolar potency against H929 cells while GC5B370 as a CD3 bispecific (GCDB41) was essentially inactive. The same v-regions, when formatted as IgG1 mAbs resulted in the opposite observation in the ADCC assay, with GC5B370 observed as more potent (by ~1100x fold) over GC5B602.

Brief Description of the Sequence Listing

| SEQ ID NO: | Type | Species | Description | Sequence |
|---|---|---|---|---|
| 1 | PRT | human | GC5B81, GC5B427, GC5B428, GC5B430, GC5B431, AND GC5B429-HCDR1 | SYAIS |
| 2 | PRT | human | GC5B379, GC5B598, GC5B465, GC5B285, GC5B463, GC5B432, GC5B433, GC5B434, GC5B435, GC5B436, GC5B461, GC5B462, GC5B437, GC5B438, GC5B439, GC5B440, GC5B441, GC5B442, GC5B443, GC5B444, GC5B464, GC5B445, GC5B446, GC5B447, GC5B448, GC5B449, and GC5B450-HCDR1 | NYWMS |
| 3 | PRT | human | GC5B483, GC5B473, GC5B478, GC5B488, | SYFIG |

Brief Description of the Sequence Listing

| SEQ ID NO: | Type | Species | Description | Sequence |
|---|---|---|---|---|
| 4 | PRT | human | GC5B493, and GC5B498-HCDR1 GC5B596-HCDR1 | GYTMN |
| 5 | PRT | human | GC5B81, GC5B427, GC5B428, GC5B430, GC5B431, and GC5B429-HCDR2 | GIIPIFGTANYAQKFQG |
| 6 | PRT | human | GC5B598, GC5B465, GC5B432, AND GC5B447-HCDR2 | GISYSGGSKYYASSVKG |
| 7 | PRT | human | GC5B599, GC5B483, GC5B481, GC5B482, GC5B484, GC5B485, AND GC5B503-HCDR2 | IIYPGKSDTRYSPSFQG |
| 8 | PRT | human | GC5B596-HCDR2 | LINPYNSDTNYAQKLQG |
| 9 | PRT | human | GCB581-HCDR3 | ESRWRGYKLD |
| 10 | PRT | human | GC5B598, GCB5465-HCDR3 | AAFDFGRRAVRLD |
| 11 | PRT | human | GC5B376, GC5B599, GC5B483, GC5B164, GC5B471, GC5B472, GC5B473, GC5B474, GC5B475, GC5B476, GC5B477, GC5B478, GC5B479, GC5B480, GC5B481, GC5B482, GC5B484, GC5B485, GC5B486, GC5B487, GC5B488, GC5B489, GC5B490, GC5B491, GC5B492, GC5B493, GC5B494, GC5B495, GC5B496, GC5B497, GC5B498, GC5B499, GC5B500, GC5B501, GC5B502, GC5B503, GC5B504, AND GC5B505-HCDR3 | VYSFGGRHKALFDY |
| 12 | PRT | human | GC5B602, GCB596-HCDR3 | VALRVALDY |
| 13 | PRT | human | GC5B382, GC5B379, GC5B370, GC5B598, GC5B597, GC5B81, GC5B465-LCDR1 | RASQSISSYLN |
| 14 | PRT | human | GC5B373, GC5B376, GC5B385, GC5B599, GC5B483-LCDR1 | RASQSVSSYLA |
| 15 | PRT | human | GC5B605, GC5B601, GC5B596-LCDR1 | KASQNVATHVG |
| 16 | PRT | human | GC5B81, GC5B465, GC5B379, GC5B598-LCDR2 | AASSLQS |
| 17 | PRT | human | GC5B373, GC5B376, GC5B385, GC5B599, GC5B483-LCDR2 | DASNRAT |
| 18 | PRT | human | GC5B602, GC5B601, GC5B596-LCDR2 | SASYRYS |
| 19 | PRT | human | GC5B379, GC5B598, GC5B81, GC5B465-LCDR3 | QQSYSTPLT |
| 20 | PRT | human | GC5B373, GC5B376, GC5B385, GC5B599, GC5B483-LCDR3 | QQRSNWPLT |
| 21 | PRT | human | GC5B602, GC5B601, GC5B596-LCDR3 | QQYNRYPYT |
| 22 | PRT | human | GPRC5D | MYKDCIESTGDYFLLCDAE GPWGIILESLAILGIVVTILL LLAFLFLMRKIQDCSQWNV LPTQLLFLLSVLGLFGLAFA FIIELNQQTAPVRYFLFGVL FALCFSCLLAHASNLVKLV RGCVSFSWTTILCIAIGCSLL QIIIATEYVTLIMTRGMMFV NMTPCQLNVDFVVLLVYV LFLMALTFFVSKATFCGPC ENWKQHGRLIFITVLFSIIIW VVWISMLLRGNPQFQRQP QWDDPVVCIALVTNAWVF LLLYIVPELCILYRSCRQEC PLQGNACPVTAYQHSFQV ENQELSRARDSDGAEEDV ALTSYGTPIQPQTVDPTQE CFIPQAKLSPQQDAGGV |

Brief Description of the Sequence Listing

| SEQ ID NO: | Type | Species | Description | Sequence |
|---|---|---|---|---|
| 23 | PRT | cyno | GPRC5D | MYKDCIESTGDYFLPCDSEGPWGIVLESLAILGIVVTILLLLAFLFLMRKIQDCSQWNVLPTQLLFLLSVLGLFGLAFAFIIQLNQQTAPVRYFLFGVLFALCFSCLLAHASNLVKLVRGRVSFSWTTILCIAIGCSLLQVIIAIEYVTLIMTRGMMFVHMTPYQLNVDFVVLLVYVLFLMALTFFVSKATFCGPCENWKQHGRLIFITVLFSIIIWVVWISMLLRGNPQFQRQPQWDDPVVCIALVTNAWVFLLLYIVPELCILYRSCRQECPSQGHACPVTAYQRSFQVENQELSRARDSDGAEEDVALTSFGTPIQPQTVDPTQECFIPRAKLSPQQDAGV |
| 24 | PRT | mouse | GPRC5D | MYEDCVKSTEDYYLFCDNEGPWAIVLESLAVIGIVVTILLLAFLFLMRKVQDCSQWNVLPTQFLFLLAVLGLFGLTFAFIIQLNHQTAPVRYFLFGVLFAICFSCLLAHASNLVKLVRGRVSFCWTTILFIAIGVSLLQTIIAIEYVTLIMTRGLMFEHMTPYQLNVDFVCLLIYVLFLMALTFFVSKATFCGPCENWKQHGRLIFATVLVSIIIWVVWISMLLRGNPQLRQPHWDDAVICIGLVTNAWVFLLIYIIPELSILYRSCRQECPTQGNVCQVPVYQRSFRMDTQEPTRARDSDGAQEDVALTAYGTPIQLQSADPSREYLIPSATLSPQQDAGL |
| 25 | PRT | human | CD3B219-HEAVY CHAIN | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS |
| 26 | PRT | human | CD3B219-LIGHT CHAIN | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL |
| 27 | PRT | human | GC5B373, GC5B376, GC5B164, GC5B501, GC5B502, GC5B503, GC5B504, AND GC5B505-HCDR1 | SYWIG |
| 28 | PRT | human | GC5B379, GC5B285, GC5B442, GC5B443, GC5B444, GC5B464, AND GC5B445-HCDR2 | GISYSGGSKYYADSVKG |
| 29 | PRT | human | GC5B373, GC5B376, GC5B164, GC5B496, GC5B497, GC5B498, GC5B499, AND GC5B500-HCDR2 | IIYPGDSDTRYSPSFQG |
| 30 | PRT | human | GC5B379, GC5B285, GC5B446, GC5B447, GC5B448, GC5B449, AND GC5B450-HCDR3 | AA<u>W</u>DFGRRAVRLDY |
| 31 | PRT | human | GC5B427-HCDR3 | ESR<u>Y</u>RGYKLDY |
| 32 | PRT | human | GC5B428-HCDR3 | ESR<u>V</u>RGYKLDY |
| 33 | PRT | human | GC5B430-HCDR3 | ESR<u>G</u>RGYKLDY |
| 34 | PRT | human | GC5B431-HCDR3 | ESR<u>A</u>RGYKLDY |
| 35 | PRT | human | GC5B429 HCDR3-VH | ESR<u>F</u>RGYKLDY |
| 36 | PRT | human | GC5B471, GC5B476, GC5B486, GC5B481, GC5B491, and GC5B496,-HCDR1 | SY<u>Y</u>IG |
| 37 | PRT | human | GC5B497, GC5B472, GC5B477, GC5B482, GC5B487, AND GC5B492-HCDR1 | SY<u>V</u>IG |
| 38 | PRT | human | GC5B474, GC5B479, GC5B484, GC5B489, GC5B494, AND GC5B499-HCDR1 | SY<u>G</u>IG |
| 39 | PRT | human | GC5B475, GC5B480, GC5B485, GC5B490, GC5B495, AND GC5B500-HCDR1 | SY<u>A</u>IG |
| 40 | PRT | human | GC5B471, GC5B472, GC5B473, GC5B474, GC5B475, AND GC5B501-HCDR2 | IIYPG<u>A</u>SDTRYSPSFQG |
| 41 | PRT | human | GC5B476, GC5B477, GC5B478, GC5B479, GC5B480, AND GC5B502-HCDR2 | IIYPG<u>S</u>SDTRYSPSFQG |

Brief Description of the Sequence Listing

| SEQ ID NO: | Type | Species | Description | Sequence |
|---|---|---|---|---|
| 42 | PRT | human | GC5B486, GC5B487, GC5B488, GC5B489, GC5B490, AND GC5B504-HCDR2 | IIYPGESDTRYSPSFQG |
| 43 | PRT | human | GC5B491, GC5B492, GC5B493, GC5B494, GC5B495, AND GC5B505-HCDR2 | IIYPGYSDTRYSPSFQG |
| 44 | PRT | human | GC5B463 AND GC5B446-HCDR2 | GISYSGGSKYYAASVKG |
| 45 | PRT | human | GC5B433, GC5B434, AND GC5B448-HCDR2 | GISYSGGSKYYAKSVKG |
| 46 | PRT | human | GC5B435, GC5B436, GC5B461, GC5B462, AND GC5B449-HCDR2 | GISYSGGSKYYAESVKG |
| 47 | PRT | human | GC5B437, GC5B438, GC5B439, GC5B440, GC5B441, AND GC5B450-HCDR2 | GISYSGGSKYYAYSVKG |
| 48 | PRT | human | GC5B463, GC5B435, GC5B437, AND GC5B442-HCDR3 | AAYDFGRRAVRLDY |
| 49 | PRT | human | GC5B432, GC5B433, GC5B438, AND GC5B443-HCDR3 | AAVDFGRRAVRLDY |
| 50 | PRT | human | GC5B461, GC5B440, AND GC5B464-HCDR3 | AAGDFGRRAVRLDY |
| 51 | PRT | human | GC5B462, GC5B441, AND GC5B445-HCDR3 | AAADFGRRAVRLDY |
| 52 | PRT | human | GC5B81-VH | QVQLVQSGAEVKKPGSSVK VSCKASGGTFSSYAISWVRQ APGQGLEWMGGIIPIFGTAN YAQKFQGRVTITADESTSTA YMELSSLRSEDTAVYYCAR ESRWRGYKLDYWGQGTLV TVSS |
| 53 | PRT | human | GC5B598, GC5B465-VH | EVQLLESGGGLVQPGGSLRL SCAASGFTFSNYWMSWVRQ APGKGLEWVSGISYSGGSK YYASSVKGRFTISRDNSKNT LYLQMNSLRAEDTAVYYCA KAAFDFGRRAVRLDYWGQ GTLVTVSS |
| 54 | PRT | human | GC5B599, GC5B483-VH | EVQLVQSGAEVKKPGESLKI SCKGSGYSFTSYFIGWVRQM PGKGLEWMGIIYPGKSDTR YSPSFQGQVTISADKSISTAY LQWSSLKASDTAMYYCAR VYSFGGRHKALFDYWGQG TLVTVSS |
| 55 | PRT | human | GC5B596-VH | QVQLVQSGAEVKKPGASVK VSCKASGYSFTGYTMNWVR QAPGQGLEWMGLINPYNSD TNYAQKLQGRVTMTTDTST STAYMELRSLRSDDTAVYY CARVALRVALDYWGQGTL VTVSS |
| 56 | PRT | human | GC5B379, GC5B598, GC5B81 and GC5465-VL | DIQMTQSPSSLSASVGDRVT ITCRASQSISSYLNWYQQKP GKAPKLLIYAASSLQSGVPS RFSGSGSGTDFTLTISSLQPE DFATYYCQQSYSTPLTFGQ GTKVEIK |
| 57 | PRT | human | GC5B373, GC5B376, GC5B385, GC5B599, GC5B483-VL | EIVLTQSPATLSLSPGERATL SCRASQSVSSYLAWYQQKP GQAPRLLIYDASNRATGIPA RFSGSGSGTDFTLTISSLEPE DFAVYYCQQRSNWPLTFG QGTKVEIK |
| 58 | PRT | human | GC5B596, GC5B602-VL | DIQMTQSPSSLSASVGDRVT ITCKASQNVATHVGWYQQK PGKAPKRLIYSASYRYSGVP SRFSGSGSGTEFTLTISNLQP EDFATYYCQQYNRYPYTFG QGTKLEIK |
| 59 | PRT | human | IgG4PAA | ASTKGPSVFPLAPCSRSTSES TAALGCLVKDYFPEPVTVS WNSGALTSGVHTFPAVLQS SGLYSLSSVVTVPSSSLGTKT YTCNVDHKPSNTKVDKRVE SKYGPPCPPCPAPEAAGGPS VFLEPPKPKDTLMISRTPEVT CVVVDVSQEDPEVQFNWYV DGVEVHNAKTKPREEQFNS TYRVVSVLTVLHQDWLNGK EYKCKVSNKGLPSSIEKTISK AKGQPREPQVYTLPPSQEEM TKNQVSLTCLVKGFYPSDIA VEWESNGQPENNYKTTPPVL DSDGSFFLYSRLTVDKSRWQ EGNVFSCSVMHEALHNHYT QKSLSLSLGK |
| 60 | PRT | human | IgG1 | ASTKGPSVFPLAPSSKSTSGG TAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLEPPKPKDTLMISRTPE VTCVVVDVSHEDPEVKFNW YVDGVEVHNAKTKPREEQY NSTYRVVSVLTVLHQDWLN GKEYKCKVSNKALPAPIEKT ISKAKGQPREPQVYTLPPSRE EMTKNQVSLTCLVKGFYPSD IAVEWESNGQPENNYKTTPP VLDSDGSFFLYSKLTVDKSR WQQGNVFSCSVMHEALHN HYTQKSLSLSPGK |
| 61 | PRT | human | GC5B382-HCDR1 | DYGMH |
| 62 | PRT | human | GC5B385-HCDR1 | GYAMS |

| SEQ ID NO: | Type | Species | Description | Sequence |
|---|---|---|---|---|
| 63 | PRT | human | GC5B370, GC5B597-HCDR1 | SYGIS |
| 64 | PRT | human | GC5B602-HCDR1 | GYSFTGYTMN |
| 65 | PRT | human | GC5B603-HCDR1 | SYAMS |
| 66 | PRT | human | GC5B601-HCDR1 | GFSLTSYNVH |
| 67 | PRT | human | GC5B382-HCDR2 | AIKYSGGSTYYADSVKG |
| 68 | PRT | human | GC5B603, GC5B385-HCDR2 | AISGSGGSTYYADSVKG |
| 69 | PRT | human | GC5B370, GC5B597-HCDR2 | GIIPIFGNINYAQKFQG |
| 70 | PRT | human | GC5B602-HCDR2 | LINPYNGDTN |
| 71 | PRT | human | GC5B601-HCDR2 | VIWAGGSTNYNSALMS |
| 72 | PRT | human | GC5B382-HCDR3 | RAESGPGLDY |
| 73 | PRT | human | GC5B373-HCDR3 | IGFYGRSFRIFDY |
| 74 | PRT | human | GC5B385-HCDR3 | VDRSFGRSRYTLDY |
| 75 | PRT | human | GC5B370, GC5B597-HCDR3 | VSRRFKRFAYYFDY |
| 76 | PRT | human | GC5B603-HCDR3 | SNFLPVVFDY |
| 77 | PRT | human | GC5B601-HCDR3 | DGIRLRFAY |
| 78 | PRT | human | GC5B382, GC5B370, GC5B597-LCDR2 | WASTRES |
| 79 | PRT | human | GC5B603-LCDR2 | TASNRAT |
| 80 | PRT | human | GC5B382, GC5B370, GC5B597-LCDR3 | QQYYSTPLT |
| 81 | PRT | human | GC5B603-LCDR3 | QQYFRAPIT |
| 82 | PRT | human | GC5B382-VH | EVQLLESGGGLVQPGGSLRLSCAASGFTFSDYGMHWVRQAPGKGLEWVSAIKYSGGSTYYADSVKGRFTISRDNSKNTLYLQMNSLRAEDTAVYYCAKRAESGPGLDYWGQGTLVTVSS |
| 83 | PRT | human | GC5B379-VH | EVQLLESGGGLVQPGGSLRLSCAASGFTFSNYWMSWVRQAPGKGLEWVSGISYSGSKYYADSVKGRFTISRDNSKNTLYLQMNSLRAEDTAVYYCAKAAWDFGRRAVRLDYWGQGTLVTVSS |
| 84 | PRT | human | GC5B376-VH | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARIGFYGRSFRIFDYWGQGTLVTVSS |
| 85 | PRT | human | GC5B376-VH | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARVYSFGGRHKALFDYWGQGTLVTVSS |
| 86 | PRT | human | GC5B385-VH | EVQLLESGGGLVQPGGSLRLSCAASGFTFSGYAMSWVRQAPGKGLEWVSAISGSGGSTYYADSVKGRFTISRDNSKNTLYLQMNSLRAEDTAVYYCAKVDRSFGRSRYTLDYWGQGTLVTVSS |
| 87 | PRT | human | GC5B370, GC5B597-VH | QVQLVQSGAEVKKPGSSVKVSCKASGGTFSSYGISWVRQAPGQGLEWMGGIIPFGNINYAQKFQGRVTITADESTSTAYMELSSLRSEDTAVYYCARVSRRFKRFAYYFDYWGQGTLVTVSS |
| 88 | PRT | human | GC5B602-VH | QVQLVQSGAEVKKPGASVKVSCKASGYSFTGYTMNWVRQAPGQGLEWMGLINPYNGDTNYAQKLQGRVTMTTDTSTSTAYMELRSLRSDDTAVYYCARVALRVALDYWGQGTLVTVSS |
| 89 | PRT | human | GC5B603-VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKSNFLPVVFDYWGQGTLVTVSS |
| 90 | DNA | human | GC5B596-light chain | Atgcgggtgctggcccagctgctgggactgctgctgctgtgcttccctggcgccagatgcgacatccagatgacccagagccccagcagcctgagcgccagcgtgggcgaccgggtgaccatcacctgcaaggccagccagaacgtggccacccacgtgggctggtaccagcagaagcccggcaaggcccccaagcggctgatctacagcgccagctaccggtacagcggcgtgcccagccggttcagcggcagcggcagcggcaccgagttcaccctgaccatcagcaacctgcagcccgaggacttcgccacctactactgccagcagtacaaccggtacccctacaccttcggccagggcaccaagctggagatcaagcgtacggtggctgcaccatctgtcttcatcttcccgccatctgatgagcagttgaaatctggaactgcctctgttgtgtgcctgctgaataacttctatcccagagaggccaaagtacagtggaaggtggataacgcctccaatcgggtaactcccaggagagtgtcacagagcaggacagcaaggacagcacctacagcctcagcagcaccctgacgctgagcaaagcagactacgagaaacacaaagtctacgcctgcgaagtcacccatcagggcctgagctcgcccgtcacaaagagcttcaacaggggagagtgttga |
| 91 | PRT | human | GC5B601-VH | QVTLKESGPVLVKPTETLTLTCTVSGFSLTSYNVHWIRQPPGKALEWLAVIWAGGSTNYNSALMSRLTISKDTSKSQVVLTMTNMRAEDTATYYCARDGIRLRFAYWGQGTLVTVSS |
| 92 | PRT | human | GC5B382, GC5B597, GC5B370-VL | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPLTFGQGTKVEIK |

Brief Description of the Sequence Listing

| SEQ ID NO: | Type | Species | Description | Sequence |
|---|---|---|---|---|
| 93 | PRT | human | GC5B603-VL | EIVLTQSPATLSLSPGERATLSCRASQSVRKSLAWYQQKPGQAPRLLIYTASNRATGIPARFSGSGSGTDFTLTISSLEPEDFAVYYCQQYFRAPITFGQGTKVEIK |
| 94 | PRT | human | GC5B601-VL | EIVMTQSPATLSVSPGERATLSCKASQNVATHVGWYQQKPGQAPRLLIYSASYRYSGIPARFSGSGSGTEFTLTISSLQSEDFAVYYCQQYNRYPYTFGQGTKLEIK |
| 95 | PRT | human | GC5B603-LCDR1 | RASQSVRKSLA |
| 96 | DNA | human | GC5B596-heavy chain | atggcctgggtctggaccctgctgttcctgatggccgctgcccagagcatccaggcccagttgcagctggtgcagagcggcgccgaggtgaagaagcccggcgccagcgtgaaggtgagctgcaaggccagcggctacagcttcaccggctacaccatgaactgggtgcggcaggcccccggccagggccctggagtggatgggcctgatcaaccctacaacagcgacaccaactacgcccagaagctgcagggccggggtgaccgatgaccaccgacaccagcaccagcaccgcctacatggagctgcggagcctgcggagcgacgacaccgccgtgtactactgcgcccgggtggccctgccgggtggccctggactactggggccagggcaccctggtgaccgtgagcagcgcctccaccaagggcccatccgtcttccccctggcgccctgctccaggagcacctccgagagcacagccgcctgggctgcctggtcaaggactacttccccgaaccggtgacggtgtcgtggaactcaggcgccctgaccagcggcgtgcacaccttcccggctgtcctacagtcctcaggactctactccctcagcagcgtggtgaccgtgccctccagcagcttgggcacgaaacctacacctgcaacgtagatcacaagcccagcaacaccaaggtggacaagagagttgagtccaaatatggtcccccatgcccaccatgcccagcacctgaggccgccgggggaccatcagtcttcctgttcccccaaaacccaaggacactctcatgatctcccggacccctgaggtcacgtgcgtggtggtggacgtgagccaggaagaccccgaggtccagttcaactggtacgtggatggcgtggaggtgcataatgccaagacaaagccgcgggaggagcagttcaacagcacgtaccgtgtggtcagcgtcctcaccgtcctgcaccaggactggctgaacggcaaggagtacaagtgcaaggtctccaacaaaggcctcccgtcctccatcgagaaaaccatctccaaagccaaagggcagccccgagaaccacaggtgtacaccctgcccccatcccaggaggagatgaccaagaaccaggtcagcctgacctgcctggtcaaaggcttctaccccagcgacatcgccgtggagtgggagagcaatgggcagccggagaacaactacaagaccacgcctcccgtgctggactccgacggctccttcttcctctacagcaggctaaccgtggacaagagcaggtggcaggaggggaatgtcttctcatgctccgtgatgcatgaggctctgcacaaccactacacacagaagagcctctccctgtctctgggtaatga |

We claim:

1. An isolated GPRC5D x CD3 bispecific antibody comprising:
   a) a first heavy chain (HC1);
   b) a second heavy chain (HC2);
   c) a first light chain (LC 1); and
   d) a second light chain (LC2),
   wherein the HC1 and the LC1 pair to form a first antigen-binding site that specifically binds CD3, and the HC2 and the LC2 pair to form a second antigen-binding site that specifically binds GPRC5D;
   wherein the HC1 comprises the amino acid sequence of SEQ ID NO: 25 and the LC1 comprises the amino acid sequence of SEQ ID NO: 26, and
   wherein the HC2 comprises the amino acid sequence of SEQ ID NO: 55 and the LC2 comprises the amino acid sequence of SEQ ID NO: 58.

2. The GPRC5D x CD3 bispecific antibody of claim 1, wherein the bispecific antibody is of IgG1, IgG2, IgG3, or IgG4 isotype.

3. The GPRC5D x CD3 bispecific antibody claim 2, wherein the bispecific antibody is IgG4 isotype.

4. The GPRC5D x CD3 bispecific antibody of claim 1, wherein the antibody binds GPRC5D on the surface of human multiple myeloma cells.

5. An isolated cell expressing the antibody of claim 1.

6. The cell of claim 5 wherein the cell is a hybridoma.

7. A pharmaceutical composition comprising the GPRC5D x CD3 bispecific antibody of claim 1 and a pharmaceutically acceptable carrier.

8. A method for generating the GPRC5D x CD3 bispecific antibody of claim 1 by culturing the cell of claim 5.

9. An isolated synthetic polynucleotide encoding the HC1, the HC2, the LC1 or the LC2 of the GPRC5D x CD3 bispecific antibody of claim 1.

* * * * *